United States Patent
Gerlach et al.

(10) Patent No.: US 6,335,363 B1
(45) Date of Patent: Jan. 1, 2002

(54) USE OF INHIBITORS OF THE KQTI CHANNEL AND METHODS OF CONTROLLING AND TREATING DISEASES CAUSED BY HELMINTHS AND ECTOPARASITES

(75) Inventors: Uwe Gerlach, Hattersheim; Joachim Hofmann, Bad Camberg; Hans Jochen Lang, Hofheim, all of (DE); Aguan Wei, Saint Louis, MO (US)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/461,806

(22) Filed: Dec. 16, 1999

(30) Foreign Application Priority Data

Dec. 17, 1998 (DE) .......................... 198 58 253

(51) Int. Cl.$^7$ .............................. A61K 31/35
(52) U.S. Cl. ...................... 514/456; 514/457
(58) Field of Search ................. 514/456, 457

(56) References Cited

U.S. PATENT DOCUMENTS

| | | | | |
|---|---|---|---|---|
| 5,607,976 A | * | 3/1997 | Englert et al. | 514/584 |
| 5,684,017 A | * | 11/1997 | Harrison et al. | 514/313 |
| 5,955,607 A | * | 9/1999 | Brendel et al. | 544/151 |
| 6,008,245 A | * | 12/1999 | Brendel et al. | 514/456 |
| 6,071,953 A | * | 6/2000 | Lang et al. | 514/457 |

FOREIGN PATENT DOCUMENTS

| | | | |
|---|---|---|---|
| CA | 2205477 | 5/1997 | C07D/311/68 |
| CA | 2229947 | 2/1998 | C07D/311/70 |
| CA | 2230349 | 2/1998 | C07D/313/08 |
| CA | 2248300 | 9/1998 | C07D/311/70 |
| CA | 2249074 | 9/1998 | C07D/311/70 |
| EP | 0807629 A1 | 11/1997 | C07D/311/68 |
| EP | 0860440 A1 | 8/1998 | C07D/311/68 |
| EP | 0861836 A1 | 9/1998 | C07D/313/08 |
| EP | 0905131 A1 | 3/1999 | C07D/311/68 |
| EP | 0906911 A1 | 4/1999 | C07D/311/68 |
| EP | 0913396 A2 | 5/1999 | C07D/311/68 |
| WO | WO 96/13520 | 5/1996 | C07K/41/705 |

OTHER PUBLICATIONS

European Search Report, mailed May 23, 2000.
Functional Properties and Tissue Distribution of Elegans Potassium Channel Homologs of Human KvLQT1, Aguan D. Wei, Alice Butler, and Lawrence Salkoff, Department of Anatomy and Neurobiology, Washington University School of Medicine, Saint Louis, MO 63110, p. A206, XP–000905423.
The Role of I$_{sK}$ Protein in the Specific Pharmacological Properties of the I$_{Ks}$ Channel Complex, A. E. Busch, G. L. Busch, E. Ford, H. Suessbrich, H.–J. Lang, R. Greger, K. Kunzelmann, B. Attali & W. Stühmer, British Journal of Pharmacology (1997) 122, p. 187–189, XP–000905465.
KvLQT1 Potassium Channel but Not IsK is the Molecular Target for trans–6–Cyano–4–(N–ethylsulfonyl–N–methylamino)–3–hydroxy–2,2–dimethyl–chromane, Gildas Loussouarn, Flavien Charpentier, Raha Mohammad– Panah, Karl Kunzelmann, Isabelle Baro, and Denis Escande, The American Society for Pharmacology and Experimental Therapeutics, p. 1131–1136, XP–000905467.

* cited by examiner

Primary Examiner—Kevin E. Weddington
(74) Attorney, Agent, or Firm—Finnegan, Henderson, Farabow, Garrett, and Dunner, L.L.P.

(57) ABSTRACT

Use of inhibitors of the KQT1 channel for preparing a medicament for treating diseases caused by helminths and ectoparasites Inhibitors of the KQT1 channel are a novel way of destroying helminths and ectoparasites. For this reason, blockers of the cellular KQT1 channel, which is present in helminths and ectoparasites, are used for preparing a medicament for the treatment of vertebrates and humans infested by helminths or ectoparasites. These KQT1 blockers are used as medicaments on their own or in combination with other medicaments and therapeutic measures.

Inhibitors of the KQT1 channel are likewise a novel mechanism of action for phytoparasites such as insects, arachnids, molluscs and nematodes, and consequently, they are used for preparing a crop protection composition.

6 Claims, No Drawings

USE OF INHIBITORS OF THE KQT1 CHANNEL AND METHODS OF CONTROLLING AND TREATING DISEASES CAUSED BY HELMINTHS AND ECTOPARASITES

The invention relates to the use of inhibitors of the KQT1 channel for treating diseases caused by helminths and ectoparasites and for controlling such phytopathogenic pests.

Parasitoses are widespread, and they cause a wide spectrum of pathological effects in man and animals, from slight physiological disturbances to severe, even deadly diseases. Today, many intensively researched diseases caused by parasites are known, threatening the health and the life of man and its domestic and useful animals.

Worldwide, with an increasing tendency, millions of people are diagnosed with an impaired immune system. This group of people is massively attacked by opportunistic parasites such that every year, there are millions of casualties. In the age of long-distance travel, exotic parasites can be encountered even in non-Third-World countries which usually have a high standard of hygiene. The reason for this is an ever-increasing trend for walking and adventure holidays under local hygiene conditions and that the feeling of safety when at home has resulted in a loss of the awareness/knowledge of hygiene risks.

Not only the protection of human health but also animal welfare demands the cure for, and, if possible, the prevention of, suffering and pain caused by parasitoses. Economics are important in particular in husbandry of useful animals, where, owing to unfavorable housing and feeding conditions for animals (for example in the case of certain forms of large-scale livestock farming), parasitic diseases contributing to a reduced performance of a quantitative (quantity of meat, number of eggs, racing ability) or qualitative (quality of meat and wool) kind predominantly occur. The huge damage caused by parasitoses in man and animals make their control desirable, if not essential, in the interests of health and economy.

The use of chemical substances which are toxicologically acceptable in the host (man, animal) and known for their effectiveness against individual parasites or relatively large groups of parasites are still of paramount importance in the control of parasites.

According to their activity spectrum, these substances are differentiated into anthelmintics, which act against helminths, antiprotozoic agents, which act against protozoa, insecticides, which act against insects, acaricides, which act against mites (acaria); the last two groups are also summarized under the name ectoparasiticides.

The increase in resistance to drugs, promoted by the long-term and intensive use in particular in modern large-scale livestock farming, or the occurrence of sometimes strong side-effects, in particular in the case of lengthy medication of people which, in the context of increasing globalization, have to work in tropic and subtropic regions for a relatively long time, and the high costs associated with the prophylaxis/therapy involving certain chemotherapeutics means that the search for other cost-efficient substance classes which have a different mechanism of action and are better tolerated is a must.

In the context of the invention, it was realized that inhibitors of the KQT1 channel represent a novel way of destroying helminths and ectoparasites. The present invention thus relates to the use of blockers of the cellular KQT1 channel, which is present in helminths and ectoparasites, for preparing a medicament for the treatment of vertebrates and humans infested by helminths or ectoparasites. These KQT1 blockers are used as medicaments on their own or in combination with other medicaments and therapeutic measures.

The treatment of a subject for infestation of helminths or ectoparasites may include treatment for the prevention of such infestation. For example, a subject initially suffering from infestation will presumably return to being a "healthy host" upon successful treatment. Additional treatment would thereafter be preventative in nature, and any period of time without such an infestation would be therapeutically useful. The ideal would be a treatment leading to permanent prevention, but the continued treatment of an individual no longer showing symptoms would be prevention.

Surprisingly, it has been found that inhibitors of the $I_{KS}$ channel are able to block the KQT1 channel in a potent manner. Thus, inhibitors of the $I_{KS}$ channel, with their blocking action on the KQT1 channel, are suitable for preparing a medicament for the treatment of diseases caused by helminths and ectoparasites.

The inhibitors of the $I_{KS}$ channel are active compounds which have become the focus of attention only during the last 10 years. In the meantime, numerous applications for this class of active compounds have been described, such as their use as medicaments for the treatment of cardiac arrhythmias, the therapy of ulcers by inhibiting secretion of gastric acid, the therapy of diarrhea, the treatment of Menière's disease, etc. Of particular importance for the therapeutic use of $I_{KS}$ blockers is their antiarrhythmic action.

The antiarrhythmic action of the $I_{KS}$ channel blockers is based on a prolongation of the plateau phase of heart cells, in particular under conditions of sympathicus stimulation. Delay of repolarization is recognized as an antiarrhythmic principle of the so-called class III antiarrhythmics for terminating malignant cardiac arrhythmias.

According to the surprising realization that the action of $I_{KS}$ inhibitors as KQT1 blockers adversely affects the viability of the helminths and ectoparasites, the invention relates to the use of the $I_{KS}$ channel blockers included in the claims of the patents below as useful therapeutics for treating infestations of man and vertebrates by helminths and ectoparasites and the resulting diseases; and also to the preparation of a crop protection composition for controlling phytopathogenic arthropods, molluscs and nematodes.

Compounds suitable for the use according to the invention include the following:

1) a chromane of the formula I, or an isomer thereof, or a physiologically acceptable salt of any of the foregoing:

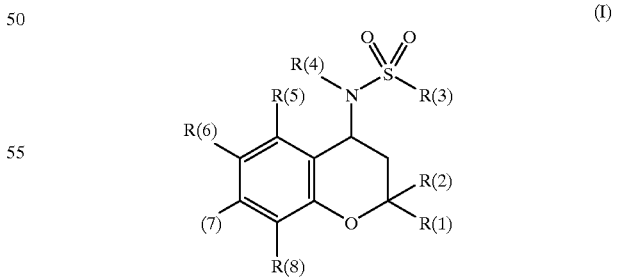

(I)

where
(1) and R(2) are the same or different, and each is hydrogen, $C_pF_{2p+1}$, alkyl having 1, 2, 3, 4, 5, or 6 C atoms, or phenyl,
where any of the foregoing is unsubstituted or substituted by 1 or 2 substituents selected from F, Cl, Br, I, CF$_3$, methyl, methoxy, sulfamoyl, methylsulfonylamino, and methylsulfonyl, and
p is 1, 2, or 3,
or
R(1) and R(2) together form an alkylene chain having 2, 3, 4, 5, 6, 7, 8, 9 or 10 C atoms,
R(3) is R(9)—C$_n$H$_{2n}$[NR(11)]$_m$—, where
R(9) is hydrogen or cycloalkyl having 3, 4, 5, 6, 7, or 8 C atoms,
n is zero, 1, 2, 3, 4, 5, 6, 7, 8, 9, or 10,
m is zero or 1,
R(11) is hydrogen or alkyl having 1, 2, 3, 4, 5, or 6 C atoms, or
R(11) together with R(9) form an alkylene group having 1, 2, 3, 4, 5, 6, 7, or 8 C atoms,
where a CH$_2$ group of the group C$_n$H$_{2n}$ is optionally replaced by —O—, —SO$_q$— or —NR(10)—,
q is zero, 1 or 2,
R(10) is hydrogen, methyl, or ethyl,
R(4) is R(12)—C$_r$H$_{2r}$, where
R(12) is hydrogen, cycloalkyl having 3, 4, 5, 6, 7, or 8 C atoms, piperidyl, 1-pyrrolidinyl, N-morpholino, N-methylpiperazino, C$_p$F$_{2p+1}$, pyridyl, thienyl, imidazolyl or phenyl,
any of the foregoing being unsubstituted or substituted by 1 or 2 substituents selected from F, Cl, Br, I, CF$_3$, methyl, methoxy, sulfamoyl, methylsulfonyl, or methylsulfonylamino;
r is 1, 2, 3, 4, 5, 6, 7, 8, 9, 10, 11, 12, 13, 14, 15, 16, 17, 18, 19, or 20,
where a CH$_2$ group of the group C$_r$H$_{2r}$ is optionally replaced by —O—, —HC=CH—, —C≡C—, —CO—, —CO—O—, —SO$_q$— or —NR(10)—,
q is zero, 1, or 2,
R(10) is hydrogen, methyl or ethyl,
R(5), R(6), R(7) and R(8) are the same or different and each is hydrogen, F, Cl, Br, I, alkyl having 1, 2, 3, or 4 C atoms, cycloalkyl having 3, 4, 5, 6, 7 or 8 C atoms, —CN, —CF$_3$, —C$_2$F$_5$, —C$_3$F$_7$, —N$_3$, —NO$_2$, —CONR(13)R(14), —COOR(15), R(16)—C$_s$H$_{2s}$—Y— or phenyl,
where any of the foregoing is unsubstituted or substituted by 1 or 2 substituents selected from F, Cl, Br, I, CF$_3$, methyl, methoxy, sulfamoyl, and methylsulfonyl,
R(13) and R(14) are the same or different and each is hydrogen or alkyl having 1, 2, or 3 C atoms,
R(15) is hydrogen, methyl, ethyl, phenyl, or —C$_u$H$_{2u}$—NR(13)R(14)
u is 2 or 3,
R(16) is hydrogen, cycloalkyl having 3, 4, 5, 6, 7, or 8 C atoms, —COOR(15), thienyl, imidazolyl, pyridyl, quinolyl, isoquinolyl, piperidyl, 1-pyrrolidinyl, N-morpholino, N-methylpiperazino, C$_t$F$_{2t+1}$, or phenyl,
where any of the foregoing is unsubstituted or substituted by 1 or 2 substituents selected from F, Cl, Br, I, CF$_3$, methyl, methoxy, sulfamoyl, and methylsulfonyl,
s is zero, 1, 2, 3, 4, 5, or 6,
t is 1, 2, or 3,
Y is SO$_q$, —CO—, —SO$_2$—NR(10)—, —O—, —NR(10)— or —CO—NR(10),
with the proviso that R(6) is other than —OCF$_3$ or —OC$_2$F$_5$;
and
2) a compound of the formula II, an isomer thereof, or a physiologically acceptable salt of any of the foregoing,

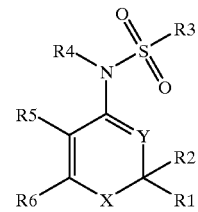

(II)

where
X is —O—, —S—, —SO—, —SO$_2$—, —NR(7)—, —CR(8a)R(8b)—, or —CO—,
R(7) is hydrogen or —(C$_a$H$_{2a}$)—R(9),
where a CH$_2$ group of the group C$_a$H$_{2a}$ is optionally replaced by —O—, —CH=CH—, —C≡C—, —CO—, —CO—O—, —O—CO—, —S—, —SO—, —SO$_2$—, NR(10)— or —CONR(10)—,
where R(10) is hydrogen or alkyl having 1, 2, or 3 C atoms,
a is zero, 1, 2, 3, 4, 5, 6, 7, or 8;
R(9) is hydrogen, CF$_3$, C$_2$F$_5$, C$_3$F$_7$, cycloalkyl having 3, 4, 5, 6, 7 or 8 C atoms, dimethylamino, diethylamino, 1-piperidyl, 1-pyrrolidinyl, 4-morpholinyl, 4-methylpiperazin-1-yl, pyridyl, thienyl, imidazolyl, or phenyl,
where pyridyl, thienyl, imidazolyl, and phenyl are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino,
or
R(7) and R(1) together form a bond,
R(8a) is hydrogen, CF$_3$, C$_2$F$_5$, C$_3$F$_7$, alkyl having 1, 2, 3, 4, 5, or 6 C atoms, or phenyl,
which is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino,
R(8b) is hydrogen, alkyl having 1, 2, or 3 C atoms, —OR(10), —COOR(10), CO—R(10),
where R(10) is hydrogen or alkyl having 1, 2, or 3 C atoms, or
one of the radicals (8a) or R(8b) together with R(1) form a bond,
Y is N or CR(11), where
R(11) is hydrogen or alkyl having 1, 2, or 3 C atoms,
R(1) and R(2) are the same or different and each is hydrogen, CF$_3$, C$_2$F$_5$, C$_3$F$_7$, F, Cl, methoxy, alkyl having 1, 2, 3, 4, 5 or 6 C atoms, or phenyl, where any of the foregoing is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, or
R(1) and R(2) together form an alkylene chain having 2, 3, 4, 5, 6, 7, 8, 9, or 10 C atoms,
R(3) is R(12)—C$_n$H$_{2n}$—NR(13)— or R(12)—C$_n$H$_{2n}$—, where one CH$_2$ group in the groups C$_n$H$_{2n}$ is optionally replaced by —O—, —CO—, —S—, —SO—, —SO$_2$—, or —NR(10a)—,
R(10a) is hydrogen, methyl, or ethyl,
R(12) is hydrogen, methyl, cycloalkyl having 3, 4, 5, 6, 7, or 8 C atoms, CF$_3$, C$_2$F$_5$, or C$_3$F$_7$, n is zero, 1, 2, 3, 4, 5, 6, 7, 8, 9, or 10,
R(13) is hydrogen or alkyl having 1, 2, 3, 4, 5, or 6 C atoms, or
R(12) and R(13) together form a bond if n is 3 or greater,
or
R(3) and R(4) together form an alkylene chain having 3, 4, 5, 6, 7, or 8 C atoms, where one CH$_2$ group of the alkylene chain is optionally replaced by —O—, —CO—, —S—, —SO—, —SO$_2$— or —NR(10a)—,
R(10a) is hydrogen, methyl, or ethyl,
R(4) is R(14)—C$_r$H$_{2r}$,
  where one CH$_2$ group of the group C$_r$H$_{2r}$ is optionally replaced by —O—, —CH=CH—, —C≡C—, —CO—, —CO—O—, —O—CO—, —S—, —SO—, —SO$_2$—, —NR(10b)—, or —CONR(10b)—,
  where R(10b) is hydrogen or alkyl having 1, 2, or 3 C atoms;
  R(14) is methyl, CF$_3$, C$_2$F$_5$, C$_3$F$_7$, cycloalkyl having 3, 4, 5, 6, 7, or 8 C atoms, —OH, —COOH, —NR(23)R(24), 1-piperidyl, 1-pyrrolidinyl, 4-morpholinyl, 4-methylpiperazin-1-yl, pyridyl, thienyl, imidazolyl, or phenyl,
    where pyridyl, thienyl, imidazolyl and phenyl are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino,
  R(23) and R(24) is the same or different and each is hydrogen or alkyl having 1, 2, or 3 C atoms,
  or
  R(23) and R(24) together form a chain of 4 or 5 methylene groups, one CH$_2$ group of which is optionally replaced by —O—, —S—, —NH—, —N(CH$_3$)—, or —N(benzyl)—,
r is zero, 1, 2, 3, 4, 5, 6, 7, 8, 9, 10, 11, 12, 13, 14, 15, 16, 17, 18, 19, or 20,
R(5) and R(6) together form a group selected from
  —CR(15)=CR(16)—CR(17)=CR(18)—,
  —CR(15)=CR(16)—CR(17)=N—,
  —CR(15)=CR(16)—N=CR(18)—,
  —CR(15)=N—CR(17)=N—,
  —CR(15)=N—N=CR(18)—,
  —N=CR(16)—CR(17)=N—, and
  —CR(15)=CR(16)—, where either end of said group is attached to the ring at the R(5) position,
R(15), R(16), R(17) and R(18) are the same or different and each is hydrogen, F, Cl, Br, I, alkyl having 1, 2, 3, 4, or 5 C atoms, cycloalkyl having 3, 4, 5, 6, 7, or 8 C atoms, —CN, —CF$_3$, —C$_2$F$_5$, —C$_3$F$_7$, —N$_3$, —NO$_2$, —Z—C$_s$H$_{2s}$—R(22), thienyl or phenyl,
  which is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino,
Z is —O—, —CO—, —CO—O—, —O—CO—, —S—, —SO—, —SO$_2$—, —SO$_2$—O—, —SO$_2$NR(10c), —NR(10c)—, or —CONR(10c)—, R(10c) is hydrogen or alkyl having 1, 2, or 3 C atoms,
s is zero, 1, 2, 3, 4, 5, or 6;
R(22) is hydrogen, CF$_3$, C$_2$F$_5$, C$_3$F$_7$, cycloalkyl having 3, 4, 5, 6, 7, or 8 C atoms, —NR(19)R(20), —COOR(21), 1-piperidyl, 1-pyrrolidinyl, 4-morpholinyl, 4-methylpiperazin-1-yl, pyridyl, thienyl, imidazolyl, quinolyl, isoquinolyl or phenyl,
  where pyridyl, thienyl, imidazolyl, quinolyl, isoquinolyl and phenyl are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl and methylsulfonylamino,
R(19) and R(20) are the same or different and each is hydrogen or alkyl having 1, 2, or 3 C atoms,
or
R(19) and R(20) together form a chain of 4 or 5 methylene groups, one CH$_2$ group of which is optionally replaced by —O—, —S—, —NH—, —N(CH$_3$)—, or —N(benzyl)—,
R(21) is hydrogen or alkyl having 1, 2, or 3 C atoms,
with the proviso that Y is other than CR(11) at the same time as X is O;
and
3) a compound of the formula III, an isomer thereof, or a physiologically acceptable salt of any of the foregoing:

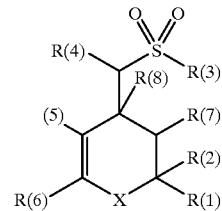

(III)

where
X is —[S(O)$_{zero, 1\ or\ 2}$]—, —NR(9)—, —[CR(9)R(23)]—, or —CO—,
R(9) is hydrogen or —(C$_n$H$_{2n}$)—R(10),
  n is zero, 1, 2, 3, 4, 5, 6, 7, or 8,
  R(10) is hydrogen, cycloalkyl having 3, 4, 5, 6, 7, or 8 C atoms, piperidyl, 1-pyrrolidinyl, N-morpholino, N-methylpiperazino, CF$_3$, C$_2$F$_5$, or C$_3$F$_7$,
    where one CH$_2$ group of the group C$_n$H$_{2n}$ is optionally replaced by —O—, —CH=CH—, —C≡C—, —CO—, —CO—O—, —[SO$_{zero, 1\ or\ 2}$]—, or —NR(11)—,
  R(11) is hydrogen, methyl, or ethyl,
  or
  R(10) is pyridyl, thienyl, imidazolyl, or phenyl, which are unsubstituted or substituted by 1 or 2 substituents selected from F, Cl, Br, I, CF$_3$, methyl, methoxy, sulfamoyl, methylsulfonyl, and methylsulfonylamino,
or
R(9) together with R(1) form a bond,
  R(23) is hydrogen, alkyl having 1, 2, or 3 C atoms, OH, O-alkyl having 1, 2, or 3 C atoms, COOH, COO-alkyl having 1, 2, or 3 C atoms or —CO—R(24), R(24) is hydrogen, methyl, or ethyl,
R(1) and R(2) are the same or different and each is hydrogen, CF$_3$, C$_2$F$_5$, C$_3$F$_7$, alkyl having 1, 2, 3, 4, 5, or 6 C atoms, or phenyl,
  where any of the foregoing is unsubstituted or substituted by 1 or 2 substituents selected from F, Cl, Br, I, CF₃, methyl, methoxy, sulfamoyl, and methylsulfonyl, or R(1) and R(2) together form an alkylene chain having 2, 3, 4, 5, 6, 7, 8, 9 or 10 C atoms, R(3) is R(12)—C$_a$H$_{2a}$[NR(13)]$_m$—, R(12) is hydrogen or cycloalkyl having 3, 4, 5, 6, 7, or 8 C atoms, CF₃, C₂F₅ or C₃F₇, a is zero, 1, 2, 3, 4, 5, 6, 7, 8, 9, or 10, m is zero or 1, R(13) is hydrogen or alkyl having 1, 2, 3, 4, 5, or 6 C atoms, or R(12) and R(13) together are an alkylene group having 4, 5, 6, 7, or 8 C atoms, where one CH₂ group of the alkylene group is optionally replaced by —O—, —[SO$_{zero, 1 or 2}$]—, —CO—, or —NR(11)—, where R(11) is hydrogen, methyl, or ethyl, R(4) is R(14)—C$_r$H$_{2r}$, r is 1, 2, 3, 4, 5, 6, 7, 8, 9, 10, 11, 12, 13, 14, 15, 16, 17, 18, 19, or 20, R(14) is hydrogen, cycloalkyl having 3, 4, 5, 6, 7, or 8 C atoms, piperidyl, 1-pyrrolidinyl, N-morpholino, N-methylpiperazino, CF₃, C₂F₅, C₃F₇, pyridyl, thienyl, imidazolyl or phenyl, where any of the foregoing is unsubstituted or substituted by 1 or 2 substituents selected from F, Cl, Br, I, CF₃, methyl, methoxy, sulfamoyl, methylsulfonyl, and methylsulfonylamino, where one CH₂ group of the group C$_r$H$_{2r}$ is optionally replaced by —O—, —CH=CH—, —C C—, —CO—, —CO—O—, —CO—NR(11)—, —[SO$_{zero, 1 or 2}$]—, or —NR(11)—, or R(3) and R(4) together form an alkylene chain having 3, 4, 5, 6, 7, or 8 C atoms, where one CH₂ group of the alkylene chain is optionally replaced by —O—, —[SO$_{zero, 1 or 2}$]—, —CO— or —NR(11)—, R(5) and R(6) together are —CR(15)=CR(16)—CR(17)=CR(18)—, —CR(15)=CR(16)—CR(17)=N—, —CR(15)=CR(16)—N=CR(18)—, —CR(15)=N—CR(17)=N—, —CR(15)=N—N=CR(18)—, —N=CR(16)—CR(17)=N—, or —S—CR(15)=CR(16)—, where R(15), R(16), R(17) and R(18) are the same or different and each is hydrogen, F, Cl, Br, I, alkyl having 1, 2, 3, or 4 C atoms, cycloalkyl having 3, 4, 5, 6, 7, or 8 C atoms, CN, CF₃, C₂F₅, C₃F₇, N₃, NO₂, —CONR(19)R(20), —COOR(21), R(22)—C$_s$H$_{2s}$—Z—, or phenyl, where any of the foregoing is unsubstituted or substituted by 1 or 2 substituents selected from F, Cl, Br, I, CF₃, methyl, methoxy, sulfamoyl, and methylsulfonyl, R(19) and R(20) are the same or different and each is hydrogen or alkyl having 1, 2, or 3 C atoms, R(21) is hydrogen, methyl, ethyl, phenyl, or —C$_u$H$_{2u}$—NR(19)R(20), u is 2 or 3, where the phenyl is unsubstituted or substituted by 1 or 2 substituents selected from F, Cl, Br, I, CF₃, methyl, methoxy, sulfamoyl, and methylsulfonyl, R(22) is hydrogen, cycloalkyl having 3, 4, 5, 6, 7, or 8 C atoms, —COOR(21), thienyl, imidazolyl, pyridyl, quinolyl, isoquinolyl, piperidyl, 1-pyrrolidinyl, N-morpholino, N-methylpiperazino, CF₃, C₂F₅, C₃F₇, or phenyl, where any of the foregoing is unsubstituted or substituted by 1 or 2 substituents selected from F, Cl, Br, I, CF₃, methyl, methoxy, sulfamoyl or methylsulfonyl, s is zero, 1, 2, 3, 4, 5, or 6, Z is —[S(O)$_{zero, 1 or 2}$]—, —CO—, —SO₂—NR(11)—, —SO₂—O—, —O—, —NR(11)—, or —[CO—NR(11)]—, R(7) is hydrogen, hydroxyl, alkoxy having 1, 2, 3, or 4 C atoms, acyloxy having 1, 2, 3, or 4 C atoms, Cl, Br, F, alkyl having 1, 2, 3, or 4 C atoms, R(8) is hydrogen or alkyl having 1, 2, 3, 4, 5, or 6 C atoms, and 4) a chromane derivative of the formula IV, an isomer thereof, or a physiologically acceptable salt of any of the foregoing:

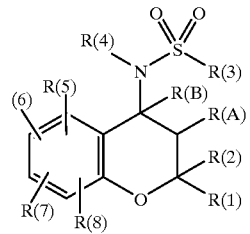

(IV)

where

R(1) and R(2) are the same or different and each is hydrogen, CF₃, C₂F₅, C₃F₇, alkyl having 1, 2, 3, 4, 5, or 6 C atoms, or phenyl, where any of the foregoing is unsubstituted or substituted by 1 or 2 substituents selected from F, Cl, Br, I, CF₃, methyl, methoxy, sulfamoyl, and methylsulfonyl, or R(1) and R(2) together form an alkylene chain having 2, 3, 4, 5, 6, 7, 8, 9, or 10 C atoms, R(A) is hydroxyl, alkanoyloxy having 1, 2, 3, 4, 5, or 6 C atoms or alkylsulfonyloxy having 1, 2, 3, 4, 5, or 6 C atoms, R(B) is hydrogen, or R(A) and R(B) together form a bond, R(3) is R(9)—C$_n$H$_{2n}$[NR(11)]$_m$—, R(9) is hydrogen or cycloalkyl having 3, 4, 5, 6, 7, or 8 C atoms, n is zero, 1, 2, 3, 4, 5, 6, 7, 8, 9, or 10, m is zero or 1, R(11) is hydrogen or alkyl having 1, 2, 3, 4, 5, or 6 C atoms, or R(11) and R(9) together form an alkylene group having 1, 2, 3, 4, 5, 6, 7, or 8 C atoms, where one CH₂ group of the group C$_n$H$_{2n}$ is optionally replaced by —O—, [SO$_{zero, 1 or 2}$—], or —NR(10), R(10) is hydrogen, methyl, or ethyl, R(4) is R(12)—C$_r$H$_{2r}$, R(12) is hydrogen, cycloalkyl having 3, 4, 5, 6, 7, or 8 C atoms, piperidyl, 1-pyrrolidinyl, N-morpholino, N-methylpiperazino, CF₃, C₂F₅, C₃F₇, pyridyl, thienyl, imidazolyl or phenyl, where pyridyl, thienyl, imidazolyl, or phenyl are unsubstituted or substituted by 1 or 2 substituents selected from F, Cl, Br, I, CF₃, methyl, methoxy, sulfamoyl, methylsulfonyl and methylsulfonylamino, r is zero, 1, 2, 3, 4, 5, 6, 7, 8, 9, 10, 11, 12, 13, 14, 15, 16, 17, 18, 19, or 20, where one CH₂ group of the group $C_rH_{2r}$ is optionally replaced by —O—, >CH=CH<, —C≡C—, —CO—, —CO—O—, SO$_{zero,\ 1\ or\ 2}$— or —NR(10)—, R(5), R(6), R(7) and R(8) are the same or different and each is hydrogen, F, Cl, Br, I, alkyl having 1, 2, 3, 4, 5, or 6 C atoms, cycloalkyl having 3, 4, 5, 6, 7 or 8 C atoms, —CN, —CF₃, —C₂F₅, —C₃F₇, —N₃, —NO₂, —CONR(13)R(14), —COOR(15), R(16)—$C_sH_{2s}$—Y— or phenyl, where any of the foregoing is unsubstituted or substituted by 1 or 2 substituents selected from F, Cl, Br, I, CF₃, methyl, methoxy, sulfamoyl and methylsulfonyl, R(13) and R(14) are the same or different and each is hydrogen or alkyl having 1, 2, or 3 C atoms, R(15) is hydrogen, methyl, ethyl, phenyl or —$C_uH_{2u}$—NR(13)R(14), u is 2 or 3, R(16) is hydrogen, cycloalkyl having 3, 4, 5, 6, 7, or 8 C atoms, —COOR(15), thienyl, imidazolyl, pyridyl, quinolyl, isoquinolyl, piperidyl, 1-pyrrolidinyl, N-morpholino, N-methylpiperazino, CF₃, C₂F₅, C₃F₇ or phenyl, where any of the foregoing is unsubstituted or substituted by 1 or 2 substituents selected from F, Cl, Br, I, CF₃, methyl, methoxy, sulfamoyl and methylsulfonyl, s is zero, 1, 2, 3, 4, 5, or 6, Y —S—, —SO—, —SO₂, —CO—, —SO₂—NR(10)—, —O—, —NR(10)—, or —CO—NR(10), with the proviso that two of the substituents R(5), R(6), R(7) and R(8) are other than hydrogen; and 5) a compound of the formula V, an isomer thereof, or a physiologically acceptable salt of any of the foregoing:

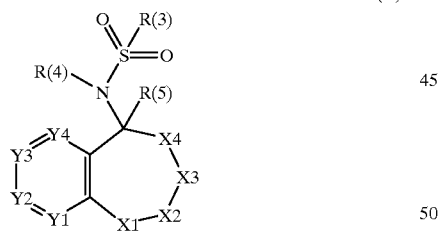

(V)

where

X1 is —O—, —S—, —SO—, —SO₂—, —CR(1)R(2)—, —NR(6)—, —CO—, or —CR(1)R(7)—,

R(1) and R(2) are the same or different and each is hydrogen, CF₃, C₂F₅, C₃F₇, alkyl having 1, 2, 3, 4, 5, or 6 C atoms, or phenyl, where any of the foregoing is unsubstituted or substituted by 1 or 2 substituents selected from F, Cl, Br, I, CF₃, NO₂, CN, NH₂, OH, methyl, ethyl, methoxy, dimethylamino, sulfamoyl, methylsulfonyl, and methylsulfonylamino, or R(1) and R(2) together form an alkylene chain having 2, 3, 4, 5, 6, 7, 8, 9 or 10 C atoms, R(6) is hydrogen or —$C_nH_{2n}$—R(8), where one CH₂ group of the group $C_nH_{2n}$ is optionally replaced by —O—, —CH=CH—, —C≡C—, —CO—, —CO—O—, —O—CO—, —S—, —SO—, —SO₂—, —NR(9)—, or —CONR(9)—, R(9) is hydrogen or alkyl having 1, 2, or 3 C atoms, n is zero, 1, 2, 3, 4, 5, 6, 7, or 8, R(8) is hydrogen, CF₃, C₂F₅, C₃F₇, cycloalkyl having 3, 4, 5, 6, 7, or 8 C atoms, dimethylamino, diethylamino, 1-piperidyl, 1-pyrrolidinyl, 4-morpholinyl, 4-methylpiperazin-1-yl, pyridyl, thienyl, imidazolyl or phenyl, where pyridyl, thienyl, imidazolyl and phenyl are unsubstituted or substituted by 1 or 2 substituents selected from F, Cl, Br, I, CF₃, NO₂, CN, NH₂, OH, methyl, ethyl, methoxy, dimethylamino, sulfamoyl, methylsulfonyl, and methylsulfonylamino, X2 is —CR(1)R(2)—, —CR(2)R(10)—, —O—, —S—, —SO—, —SO₂—, or —NR(6)—, where the radicals R(1), R(2), and R(6) are as defined under X1, and the radicals R(1), R(2), and R(6) in X2 are the same or different as X1, R(10) together with R(7) forms a bond, X3 is —CR(1)R(2)—, —O—, —S—, —SO—, —SO₂— or —NR(6)—, where the radicals R(1), R(2), and R(6) are as defined under X1, and the radicals R(1), R(2), and R(6) in X2 are the same or different as X1, X4 is —CR(1)R(2)—, —NR(6)—, —NR(11)—, —CH(OR(30))—, or —CR(2)R(11)—, where the radicals R(1), R(2), and R(6) are as defined under X1, and the radicals R(1), R(2), and R(6) in X2 are the same or different as X1, R(30) is hydrogen, alkyl having 1, 2, or 3 C atoms, or acyl having 1, 2, 3, or 4 C atoms, R(11) together with R(5) forms a bond, Y1, Y2, Y3, and Y4 are the same or different and each is —CR(12)— or N, where at most 2 of the groups Y1, Y2, Y3 and Y4 are simultaneously N, the radicals R(12) are the same or different and each is hydrogen, F, Cl, Br, I, alkyl having 1, 2, 3, 4, or 5 C atoms, cycloalkyl having 3, 4, 5, 6, 7, or 8 C atoms, CN, CF₃, C₂F₅, C₃F₇, N₃, NO₂, —Z—$C_mH_{2m}$—R(13), or phenyl, where any of the foregoing is unsubstituted or substituted by 1 or 2 substituents selected from F, Cl, Br, I, CF₃, NO₂, CN, NH₂, OH, methyl, ethyl, methoxy, dimethylamino, sulfamoyl, methylsulfonyl, and methylsulfonylamino, Z is —O—, —CO—, —CO—O—, —O—CO—, —S—, —SO—, —SO₂—, —SO₂NR(14)—, —NR(14)—, or —CONR(14)—, R(14) is hydrogen or alkyl having 1, 2, or 3 C atoms, m is zero, 1, 2, 3, 4, 5, or 6, R(13) is hydrogen, CF₃, C₂F₅, C₃F₇, cycloalkyl having 3, 4, 5, 6, 7, or 8 C atoms, —NR(15)R(16), —CONR(15)R(16), —OR(30a), phenyl, thienyl, or an N-containing heterocycle having 1, 2, 3, 4, 5, 6, 7, 8 or 9 C atoms, where phenyl, thienyl and the N-containing heterocycle are unsubstituted or substituted by 1 or 2 substituents selected from F, Cl, Br, I, CF₃, NO₂, CN, NH₂, OH, methyl, ethyl, methoxy, dimethylamino, sulfamoyl, methylsulfonyl, and methylsulfonylamino, R(15) and R(16) are the same or different and each is hydrogen or alkyl having 1, 2, or 3 C atoms, or R(15) and R(16) together are a chain of 4 or 5 methylene groups, one CH$_2$ group of which is optionally replaced by —O—, —S—, —NH—, —N(CH$_3$)— or —N(benzyl)—, R(30a) is hydrogen, alkyl having 1, 2, or 3 C atoms, or acyl having 1, 2, 3, or 4 C atoms, or Y1 and Y2 together are an S atom and Y3 and Y4 are each —CR(12)—, where the radicals R(12) are the same or different and each is as defined under Y1, Y2, Y3, and Y4, R(3) is R(17)—C$_x$H$_{2x}$—NR(18)— or R(17)—C$_x$H$_{2x}$—, where one CH$_2$ group in the groups C$_x$H$_{2x}$ is optionally replaced by —O—, —CO—, —S—, —SO—, —SO$_2$—, or —NR(19)—, where R(19) is hydrogen, methyl, or ethyl, R(17) is hydrogen, methyl, cycloalkyl having 3, 4, 5, 6, 7, or 8 C atoms, CF$_3$, C$_2$F$_5$, or C$_3$F$_7$, x is zero, 1, 2, 3, 4, 5, 6, 7, 8, 9, or 10, R(18) is hydrogen or alkyl having 1, 2, 3, 4, 5, 6, 7, or 8 C atoms, or R(18) and R(17) together form a bond if x is 3 or greater, or R(3) is phenyl, which is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, or R(3) together with R(4) are an alkylene chain having 3, 4, 5, 6, 7, or 8 C atoms, where one CH$_2$ group of the alkylene chain is optionally replaced by —O—, —CO—, —S—, —SO—, or SO$_2$, R(4) is —C$_r$H$_{2r}$—R(20), where one CH$_2$ group of the group C$_r$H$_{2r}$ is optionally replaced by —O—, —CH=CH—, —C≡C—, —CO—, —CO—O—, —O—CO—, —S—, —SO—, —SO$_2$—, —NR(21)—, or —CONR(21)—, R(21) is hydrogen or alkyl having 1, 2, or 3 C atoms, r is zero, 1, 2, 3, 4, 5, 6, 7, 8, 9, 10, 11, 12, 13, 14, 15, 16, 17, 18, 19, or 20, R(20) is drogen, methyl, CF$_3$, C$_2$F$_5$, C$_3$F$_7$, cycloalkyl having 3, 4, 5, 6, 7 or 8 C atoms, —NR(22)R(23), phenyl, thienyl, or an N-containing heterocycle having 1, 2, 3, 4, 5, 6, 7, 8, or 9 C atoms, where phenyl, thienyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, R(22) and R(23) are the same or different and each is hydrogen or alkyl having 1, 2, or 3 C atoms, or R(22) and R(23) together are a chain of 4 or 5 methylene groups one CH$_2$ group of which is optionally replaced by —O—, —S—, —NH—, —N(CH$_3$)— or —N(benzyl)—, R(5) is hydrogen or together with R(11) forms a bond; and 6) a compound of the formula VI, an isomer thereof, or a physiologically acceptable salt of any of the foregoing:

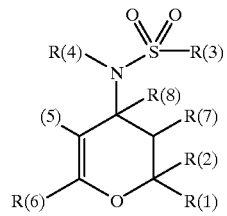

(VI)

in which:

R(1) and R(2) are the same or different and each is hydrogen, CF$_3$, C$_2$F$_5$, C$_3$F$_7$, alkyl having 1, 2, 3, 4, 5, or 6 C atoms, or phenyl, where any of the foregoing is unsubstituted or substituted by 1 or 2 substituents selected from F, Cl, Br, I, CF$_3$, methyl, methoxy, sulfamoyl, and methylsulfonyl, or R(1) and R(2) together form an alkylene chain having 2, 3, 4, 5, 6, 7, 8, 9, or 10 C atoms, where one CH$_2$ group of the alkylene chain is optionally replaced by —O—, —CO—, —S—, —SO—, —SO$_2$—, or —NR(10)—, R(10) is hydrogen or alkyl having 1, 2, or 3 C atoms, R(3) is R(12)—C$_a$H$_{2a}$[NR(13)]$_m$—, R(12) is hydrogen or cycloalkyl having 3, 4, 5, 6, 7, or 8 C atoms, CF$_3$, C$_2$F$_5$, or C$_3$F$_7$, a is zero, 1, 2, 3, 4, 5, 6, 7, 8, 9, or 10, m is zero or 1, R(13) is hydrogen or alkyl having 1, 2, 3, 4, 5, or 6 C atoms, or R(12) and R(13) together form an alkylene group having 4, 5, 6, 7 or 8 C atoms, where one CH$_2$ group of the alkylene group is optionally replaced by —O—, —[SO$_{zero, 1\ or\ 2}$]—, —CO— or —NR(10)—, R(10) is hydrogen or alkyl having 1, 2, or 3 C atoms, R(4) is R(14)—C$_r$H$_{2r}$ where r is zero, 1, 2, 3, 4, 5, 6, 7, 8, 9, 10, 11, 12, 13, 14, 15, 16, 17, 18, 19, or 20, R(14) is hydrogen, cycloalkyl having 3, 4, 5, 6, 7, or 8 C atoms, piperidyl, 1-pyrrolidinyl, N-morpholino, N-methylpiperazino, CF$_3$, C$_2$F$_5$, C$_3$F$_7$, pyridyl, thienyl, imidazolyl, or phenyl, where any of the foregoing is unsubstituted or substituted by 1 or 2 substituents selected from F, Cl, Br, I, CF$_3$, methyl, methoxy, sulfamoyl, methylsulfonyl, and methylsulfonylamino, where one CH$_2$ group of the group C$_r$H$_{2r}$ is optionally replaced by —O—, —CH=CH—, —C≡C—, —CO—, —CO—O—, —CO—NR(11)—, —[SO$_{zero, 1\ or\ 2}$]—, or —NR(11)—, R(11) is hydrogen or —(C$_a$H$_{2a}$)—R(10), where one CH$_2$ group of the group C$_a$H$_{2a}$ is optionally replaced by —O—, —CH=CH—, —C≡C—, —CO—, —CO—O—,
—O—CO—, —S—, —SO—, —SO$_2$—,
NR(10)—, or —CONR(10)—,
R(10) is hydrogen or alkyl having 1, 2, or 3 C
atoms, or R(3) and R(4) together form an alkylene chain having
3, 4, 5, 6, 7 or 8 C atoms,
where one CH$_2$ group of the alkylene chain is
optionally replaced by —O—, —[SO$_{zero, 1\ or\ 2}$]—,
—CO—, or —NR(11)—, where
R(11) is hydrogen or —(C$_a$H$_{2a}$)—R(10),
where one CH$_2$ group of the group C$_a$H$_{2a}$ is
optionally replaced by —O—, —CH=CH—,
—C≡C—, —CO—, —CO—O—,
—O—CO—, —S—, —SO—, —SO$_2$—,
NR(10)—, or —CONR(10)—,
R(10) is hydrogen or alkyl having 1, 2, or 3 C
atoms, R(5) and R(6) are
—CR(15)=CR(16)—CR(17)=N—,
—CR(15)=CR(16)—N=CR(17)—,
—CR(15)=N—CR(17)=N—,
—CR(15)=N—N=CR(17)—,
—N=CR(16)—CR(17)=N— or
—S—CR(15)=CR(16)—;
R(15), R(16), and R(17) are the same or different and
each is hydrogen, F, Cl, Br, I, alkyl having 1, 2, 3,
or 4 C atoms, cycloalkyl having 3, 4, 5, 6, 7, or 8
C atoms, CN, CF$_3$, C$_2$F$_5$, C$_3$F$_7$, N$_3$, NO$_2$,
—CONR(19)R(21), —COOR(21), R(22)—
C$_s$H$_{2s}$—Z—, or phenyl,
where any of the foregoing is unsubstituted or
substituted by 1 or 2 substituents selected from
F, Cl, Br, I, CF$_3$, methyl, methoxy, sulfamoyl
and methylsulfonyl,
R(19) is hydrogen or alkyl having 1, 2, or 3 C
atoms,
R(21) is hydrogen, methyl, ethyl, phenyl or
—C$_u$H$_{2u}$—NR(19)R(20),
where the phenyl is unsubstituted or substituted by 1 or 2 substituents selected from F, Cl,
Br, I, CF$_3$, methyl, methoxy, sulfamoyl, and
methylsulfonyl, where
R(20) is hydrogen or alkyl having 1, 2, or 3 C
atoms,
u is 2 or 3,
R(22) is hydrogen, cycloalkyl having 3, 4, 5, 6, 7
or 8 C atoms, —COOR(21), CONR(19)R(21),
thienyl, imidazolyl, pyridyl, quinolyl,
isoquinolyl, piperidyl, 1-pyrrolidinyl,
N-morpholino, N-methylpiperazino, CF$_3$,
C$_2$F$_5$, C$_3$F$_7$ or phenyl,
where any of the foregoing is unsubstituted or
substituted by 1 or 2 substituents selected from
F, Cl, Br, I, CF$_3$, methyl, methoxy, sulfamoyl
and methylsulfonyl,
s is zero, 1, 2, 3, 4, 5, or 6,
Z is —[S(O)$_{zero, 1\ or\ 2}$]—, —CO—, —SO$_{(0, 1\ or\ 2)}$—NR(11)—, —SO$_2$—O—, —O—, —NR(11)—, or —[CO—NR(11)]—,
R(7) is hydrogen, hydroxyl, alkoxy having 1, 2, 3, or 4
C atoms, acyloxy having 1, 2, 3, or 4 C atoms, Cl, Br,
F, alkyl having 1, 2, 3, or 4 C atoms,
R(8) is hydrogen or alkyl having 1, 2, 3, 4, 5, or 6 C
atoms; and 7) a compound of the formula VII, an isomer thereof, or
a physiologically acceptable salt of any of the foregoing:

(VII)

[Structure: chroman-type ring system with substituents R(1) through R(9), N-SO$_2$-R(3) group, with R(4), R(5) on nitrogen area, R(6), R(7), R(8) on aromatic ring, R(9), R(2) on saturated ring, R(1) adjacent to O, labeled B]

where

R(1) and R(2) are the same or different and each is
hydrogen, CF$_3$, C$_2$F$_5$, C$_3$F$_7$, alkyl having 1, 2, 3, 4,
5 or 6 C atoms or phenyl,
where any of the foregoing is unsubstituted or substituted by 1 or 2 substituents selected from F, Cl,
Br, I, CF$_3$, NO$_2$, CN, NH$_2$, OH, methyl, ethyl,
methoxy, dimethylamino, sulfamoyl,
methylsulfonyl, and methylsulfonylamino, or R(1) and R(2) together are an alkylene chain having 2,
3, 4, 5, 6, 7, 8, 9, or 10 C atoms,
R(3) is R(10)—C$_n$H$_{2n}$—NR(11)— or R(10)—
C$_n$H$_{2n}$—,
where one CH$_2$ group in the groups C$_n$H$_{2n}$ is optionally replaced by —O—, —CO—, —S—,
—SO—, —SO$_2$—, or —NR(12a)—;
R(12a) is hydrogen, methyl or ethyl,
R(10) is hydrogen, methyl, cycloalkyl having 3, 4, 5,
6, 7, or 8 C atoms, CF$_3$, C$_2$F$_5$, or C$_3$F$_7$,
n is zero, 1, 2, 3, 4, 5, 6, 7, 8, 9, or 10,
R(11) is hydrogen or alkyl having 1, 2, 3, 4, 5, or 6
C atoms, or R(10) and R(11) together form a bond if n is 3 or
greater,
R(4) is R(13)—C$_r$H$_{2r}$—Z—C$_q$H$_{2q}$—,
q is 0, 1, 2, 3, 4, 5, 6, 7, or 8,
r is 0, 1, 2, 3, 4, 5, 6, 7, or 8,
Z is —CO—NR(14)—,
—OCO—NR(14)—,
—O—C$_x$H$_{2x}$—O—,
—O—C$_x$H$_{2x}$—NR(14)—,
—O—C$_x$H$_{2x}$—CO—O,
—CO—O—C$_x$H$_{2x}$—O— or
—CO—O—C$_x$H$_{2x}$—NR(14)—,
where either end of the groups defined by Z is
attached to C$_r$H$_{2r}$,
x is 2, 3, or 4,
R(14) is hydrogen, alkyl having 1, 2, or 3 C
atoms, —C$_y$H$_{2y}$—OR(12b), —C$_y$H$_{2y}$—NR(12b)$_2$,
where R(12b) is hydrogen, methyl, or ethyl,
y is 2 or 3, R(13) is H, CF$_3$, C$_2$F$_5$, C$_3$F$_7$, cycloalkyl having 3, 4, 5, 6, 7 or 8 C atoms, —NR(15)R(16), —CONR(15)R(16), —C(=NR(17))NR(15)R(16), —OR(17), —COOR(17), phenyl or an N-containing heterocycle having 1, 2, 3, 4, 5, 6, 7, 8, or 9 C atoms,
  where phenyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, aminosulfonyl and methylsulfonylamino,
  R(15) and R(16) are the same or different and each is hydrogen, alkyl having 1, 2, 3, or 4 C atoms, or —C$_z$H$_{2z}$-phenyl,
  where phenyl is unsubstituted or substituted by 1 or 2 substituents selected from F, Cl, Br, CF$_3$, NO$_2$, CN, OH, methyl, ethyl, methoxy, dimethylamino, sulfamoyl, methylsulfonyl, aminosulfonyl and methylsulfonylamino,
  or R(15) and R(16) together form a chain of 4 or 5 methylene groups, one CH$_2$ group of which is optionally replaced by —O—, —S—, —NH—, —N(CH$_3$)—, or —N(benzyl)—,
  R(17) is hydrogen or alkyl having 1, 2, or 3 C atoms,
R(5), R(6), R(7), and R(8) are the same or different and each is hydrogen, F, Cl, Br, I, alkyl having 1, 2, 3, 4, or 5 C atoms, cycloalkyl having 3, 4, 5, 6, 7, or 8 C atoms, —CN, —CF$_3$, —C$_2$F$_5$, —C$_3$F$_7$, —N$_3$, —NO$_2$, —Y—C$_s$H$_{2s}$—R(18), or phenyl,
  where any of the foregoing is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino,
  Y is —O—, —CO—, —CO—O—, —O—CO—, —S—, —SO—, —SO$_2$—, —SO$_2$—O—, —SO$_2$NR(10c), —NR(10c)—, or —CONR(10c)—, where R(10c) is hydrogen or alkyl having 1, 2, or 3 C atoms,
  s is zero, 1, 2, 3, 4, 5, or 6;
  R(18) is hydrogen, CF$_3$, C$_2$F$_5$, C$_3$F$_7$, cycloalkyl having 3, 4, 5, 6, 7 or 8 C atoms, —COOR(21), 1-piperidyl, 1-pyrrolidinyl, 4-morpholinyl, 4-methylpiperazin-1-yl, pyridyl, thienyl, imidazolyl, quinolyl, isoquinolyl, or phenyl,
    where pyridyl, thienyl, imidazolyl, quinolyl, isoquinolyl and phenyl are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino,
    R(21) is hydrogen or alkyl having 1, 2, or 3 C atoms,
R(9) is hydrogen, OR(10d) or OCOR(10d), where R(10d) is hydrogen or alkyl having 1, 2 or 3 C atoms,
B is hydrogen,
or
R(9) and B together form a bond; and
8) a compound of the formula VIII, an isomer thereof, or a physiologically acceptable salt of any of the foregoing:

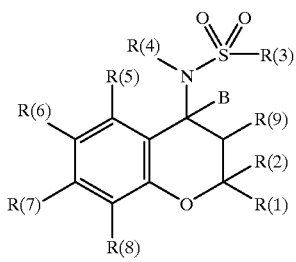

(VIII)

where
R(1) and R(2) are the same or different and each is hydrogen, CF$_3$, C$_2$F$_5$, C$_3$F$_7$, alkyl having 1, 2, 3, 4, 5, or 6 C atoms, or phenyl,
  where any of the foregoing is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino,
or
R(1) and R(2) together form an alkylene chain having 2, 3, 4, 5, 6, 7, 8, 9, or 10 C atoms,
R(3) is R(10)—C$_n$H$_{2n}$—NR(11)— or R(10)—C$_n$H$_{2n}$—,
  where one CH$_2$ group in the groups C$_n$H$_{2n}$ is optionally replaced by —O—, —CO—, —S—, —SO—, —SO$_2$—, or —NR(12a)—, where R(12a) is hydrogen, methyl or ethyl,
  R(10) is hydrogen, methyl, cycloalkyl having 3, 4, 5, 6, 7, or 8 C atoms, CF$_3$, C$_2$F$_5$, or C$_3$F$_7$,
  n is zero, 1, 2, 3, 4, 5, 6, 7, 8, 9, or 10,
  R(11) is hydrogen or alkyl having 1, 2, 3, 4, 5, or 6 C atoms,
  or
  R(10) and R(11) together form a bond if n is 3 or greater,
or
R(3) together with R(4) form an alkylene chain having 3, 4, 5, 6, 7, or 8 C atoms,
  where one CH$_2$ group of the alkylene chain is optionally replaced by —O—, —CO—, —S—, —SO—, —SO$_2$—, or —NR(12a)—,
  where R(12a) is hydrogen, methyl, or ethyl,
R(4) is R(13)—C$_r$H$_{2r}$,
  where one CH$_2$ group of the group C$_r$H$_{2r}$ is optionally replaced by —O—, —CH=CH—, —C≡C—, —CO—, —CO—O—, —O—CO—, —S—, —SO—, —SO$_2$—, —NR(14)—, or —CONR(14)—,
  where R(14) is hydrogen, alkyl having 1, 2, or 3 C atoms, —C$_y$H$_{2y}$—OR(12b), or —C$_y$H$_{2y}$—NR(12b)$_2$,
    where R(12b) is hydrogen, methyl, or ethyl,
    y is 2 or 3,
  R(13) is H, CF$_3$, C$_2$F$_5$, C$_3$F$_7$, cycloalkyl having 3, 4, 5, 6, 7, or 8 C atoms, —NR(15)R(16), —CONR(15)R(16), —OR(17), —COOR(17), phenyl, or an N-containing heterocycle having 1, 2, 3, 4, 5, 6, 7, 8, or 9 C atoms,
    where phenyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, R(15) and R(16) are the same or different and each is hydrogen or alkyl having 1, 2, 3, or 4 C atoms, or R(15) and R(16) together form a chain of 4 or 5 methylene groups, one $CH_2$ group of which is optionally replaced by —O—, —S—, —NH—, —N($CH_3$)—, or —N(benzyl)—, R(17) is hydrogen, alkyl having 1, 2, or 3 C atoms, —$C_xH_{2x}$OR(12c), where R(12c) is hydrogen, methyl or ethyl, x is 2 or 3, r is zero, 1, 2, 3, 4, 5, 6, 7, 8, 9, 10, 11, 12, 13, 14, 15, 16, 17, 18, 19, or 20, at least one of the substituents R(5), R(6), R(7) and R(8) is —Y—$C_sH_{2s}$—R(18), thienyl, furyl, or an N-containing heterocycle having 1, 2, 3, 4, 5, 6, 7, 8, or 9 C atoms, where thienyl, furyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, methylamino, dimethylamino, ethylamino, diethylamino, sulfamoyl, methylsulfonyl and methylsulfonylamino, Y is —O—, —CO—, —O—CO—, —S—, —SO—, —$SO_2$—, —$SO_2$—O—, —$SO_2$NR(12d)—, —NR(12d)—, or —CONR(12d)—, where the attachment to the benzene ring is, in each case, effected through the atom depicted on the left of each of the above groups;

where R(12d) is hydrogen, methyl or ethyl, s is 1, 2, 3, 4, 5, or 6,

R(18) is substituted phenyl carrying one or two substituents selected from $NO_2$, CN, $NH_2$, N(methyl)$_2$, OH, ethyl, —COOH, —COOmethyl, —COOethyl, —$CONH_2$, and —CON(methyl)$_2$, or R(18) is a substituted N-containing heterocycle having 1, 2, 3, 4, 5, 6, 7, 8, or 9 C atoms carrying 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(18) is —OR(19), —$SO_2$R(19), —NR(19)R(20), or —CONR(19)R(20), where R(19) and R(20) are the same or different and each is $C_tH_{2t}$—R(21), t is zero, 1, 2, 3, 4, 5, or 6, R(21) is hydrogen, $CF_3$, $C_2F_5$, $C_3F_7$, cycloalkyl having 3, 4, 5, 6, 7, or 8 C atoms, NR(22)R(23), —OR(24), phenyl, thienyl, or an N-containing heterocycle having 1, 2, 3, 4, 5, 6, 7, 8, or 9 C atoms, where phenyl, thienyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(22) and R(23) are the same or different and each is hydrogen, alkyl having 1, 2 or 3 C atoms, or R(22) and R(23) together are a chain of 4 or 5 methylene groups, one $CH_2$ group of which is optionally replaced by —O—, —S—, —NH—, —N($CH_3$)—, or —N(benzyl)—, R(24) is hydrogen, alkyl having 1, 2, or 3 C atoms, and in each case the other substituents R(5), R(6), R(7), and R(8), which are not defined above are the same or different and each is hydrogen, F, Cl, Br, I, alkyl having 1, 2, 3, 4, or 5 C atoms, cycloalkyl having 3, 4, 5, 6, 7, or 8 C atoms, CN, $CF_3$, $NO_2$, OR(12e), or NR(12e)R(12f), where R(12e) and R(12f) are the same or different and each is hydrogen or alkyl having 1, 2, 3, or 4 C atoms, R(9) is hydrogen, OR(12g), or OCOR(12g), where R(12g) is hydrogen or alkyl having 1, 2, or 3 C atoms, B is hydrogen, or R(9) and B together form a bond; and 9) a compound of the formula IX, an isomer thereof, or a physiologically acceptable salt of any of the foregoing:

(IX)

where R(5) is attached to one of the positions labeled 5, 6, 7, and 8, and where R(1) and R(2) are the same or different and each is hydrogen, $CF_3$, $C_2F_5$, $C_3F_7$, alkyl having 1, 2, 3, 4, 5 or 6 C atoms or phenyl, where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(1) and R(2) together form an alkylene chain having 2, 3, 4, 5, 6, 7, 8, 9, or 10 C atoms, R(3) is R(10)—$C_nH_{2n}$—NR(11)— or R(10)—$C_nH_{2n}$—, where one $CH_2$ group in the group $C_nH_{2n}$ is optionally replaced by —O—, —CO—, —S—, —SO—, —$SO_2$—, or —NR(12a)—, where R(12a) is hydrogen, methyl, or ethyl, R(10) is hydrogen, methyl, cycloalkyl having 3, 4, 5, 6, 7, or 8 C atoms, $CF_3$, $C_2F_5$, or $C_3F_7$, n is zero 1, 2, 3, 4, 5, 6, 7, 8, 9, or 10, R(11) is hydrogen or alkyl having 1, 2, 3, 4, 5, or 6 C atoms, or R(10) and R(11) together form a bond if n is 3 or greater;

or

R(3) together with R(4) is an alkylene chain having 3, 4, 5, 6, 7, or 8 C atoms, where one $CH_2$ group of the alkylene chain is optionally replaced by —O—, —CO—, —S—, —SO—, —$SO_2$—, or —NR(12a)—, where R(12a) is hydrogen, methyl, or ethyl,

19

R(4) is R(13)—$C_rH_{2r}$,
  where one $CH_2$ group of the group $C_rH_{2r}$ is optionally replaced by —O—, —CH=CH—, —C≡C—, —CO—, —CO—O—, —O—CO—, —S—, —SO—, —SO$_2$—, or —NR(14)—, where R(14) is hydrogen or alkyl having 1, 2, or 3 C atoms,
  R(13) is $CH_3$, $CF_3$, $C_2F_5$, $C_3F_7$, cycloalkyl having 3, 4, 5, 6, 7, or 8 C atoms, NR(15)R(16), phenyl, or an N-containing heterocycle having 1, 2, 3, 4, 5, 6, 7, 8, or 9 C atoms,
    where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
    R(15) and R(16) together are a chain of 4 or 5 methylene groups, one $CH_2$ group of which is optionally replaced by —O—, —S—, —NH—, —N(methyl)—, or —N(benzyl)—,
  r is zero, 1, 2, 3, 4, 5, 6, 7, 8, 9, 10, 11, 12, 13, 14, 15, 16, 17, 18, 19, or 20,
R(5) is —Y—$C_sH_{2s}$—R(18) or phenyl,
  where the phenyl is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
  Y is —O—, —S—, or —NR(10c)—, where R(10c) is hydrogen or alkyl having 1, 2, or 3 C atoms,
  s is 1, 2, 3, 4, 5, 6, 7, or 8,
  R(18) is hydrogen, $CF_3$, $C_2F_5$, $C_3F_7$, cycloalkyl having 3, 4, 5, 6, 7, or 8 C atoms, —COOR(21), NR(15a)R(16a), an unsubstituted N-containing heterocycle having 1, 2, 3, 4, 5, 6, 7, 8, or 9 C atoms, phenyl, or thienyl,
    where phenyl and thienyl are unsubstituted or substituted by 1 or 2 substituents selected from F, Cl, Br, I, $CF_3$, methyl, methoxy, sulfamoyl, methylsulfonyl, and methylsulfonylamino,
    R(15a) and R(16a) together form a chain of 4 or 5 methylene groups, one $CH_2$ group of which is optionally replaced by —O—, —S—, —NH—, —N(methyl)—, or —N(benzyl)—,
    R(21) is hydrogen or alkyl having 1, 2, or 3 C atoms,
R(6) is OR(10d) or OCOR(10d),
  where R(10d) is hydrogen or alkyl having 1, 2, or 3 C atoms,
B is hydrogen,
or
R(6) and B together form a bond, and 10) a compound of the formula X, an isomer thereof, or a physiologically acceptable salt of any of the foregoing:

20

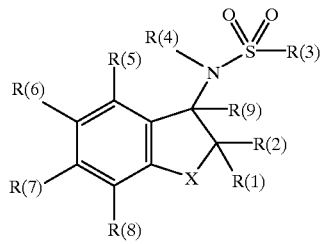

(X)

where
R(1) and R(2) are the same or different and each is hydrogen, $CF_3$, alkyl having 1, 2, 3, 4, 5, or 6 C atoms,
or
R(2) and R(9) together form a bond,
or R(2) is —OR(10a),
  where R(10a) is hydrogen, acetyl, or alkyl having 1, 2, or 3 C atoms,
R(3) is R(10b)—$C_nH_{2n}$—NR(11)— or R(10b)—$C_nH_{2n}$—,
  where one $CH_2$ group in the groups $C_nH_{2n}$ is optionally replaced by —O—, —CO—, —S—, —SO—, —SO$_2$—, or —NR(12a)—, R(12a) is hydrogen, methyl or ethyl,
  R(10b) is methyl, cycloalkyl having 3, 4, 5, 6, 7, or 8 C atoms, $CF_3$, $C_2F_5$, or $C_3F_7$,
  n is zero, 1, 2, 3, 4, 5, 6, 7, 8, 9, or 10,
  R(11) is hydrogen or alkyl having 1, 2, 3, 4, 5, or 6 C atoms,
or
  R(10b) and R(11) together form a bond if n is greater than 2,
or
R(3) together with R(4) form an alkylene chain having 3, 4, 5, 6, 7, or 8 C atoms,
  where one $CH_2$ group of the alkylene chain is optionally replaced by —O—, —CO—, —S—, —SO—, —SO$_2$—, or —NR(12a)—,
  where R(12a) is hydrogen, methyl, or ethyl,
R(4) is R(13)—$C_rH_{2r}$,
  where one $CH_2$ group of the group $C_rH_{2r}$ is optionally replaced by —O—, —CH=CH—, —C≡C—, —CO—, —CO—O—, —O—CO—, —S—, —SO—, —SO$_2$—, —NR(14)—, or —CONR(14)—,
  R(14) is hydrogen, alkyl having 1, 2, or 3 C atoms, —$C_yH_{2y}$—OR(12b), or —$C_yH_{2y}$—NR(12b)$_2$,
    where R(12b) is hydrogen, methyl, or ethyl,
    y is 2 or 3,
  R(13) is $CH_3$, $CF_3$, $C_2F_5$, $C_3F_7$, cycloalkyl having 3, 4, 5, 6, 7, or 8 C atoms, —NR(15)R(16), —CONR(15)R(16), —OR(17), —COOR(17), phenyl, or an N-containing heterocycle having 1, 2, 3, 4, 5, 6, 7, 8, or 9 C atoms,
    where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
    R(15) and R(16) are the same or different and each is hydrogen or alkyl having 1, 2, 3 or 4 C atoms, or
R(15) and R(16) together form a chain of 4 or 5 methylene groups, one CH$_2$ group of which is optionally replaced by —O—, —S—, —NH—, —N(CH$_3$)— or —N(benzyl)—, R(17) is hydrogen, alkyl having 1, 2, or 3 C atoms, —C$_z$H$_{2z}$OR(12c),
where R(12c) is hydrogen, methyl, or ethyl,
z is 2 or 3, r is zero, 1, 2, 3, 4, 5, 6, 7, 8, 9, 10, 11, 12, 13, 14, 15, 16, 17, 18, 19, or 20, R(5), R(6), R(7) and R(8) are the same or different and each is hydrogen, F, Cl, Br, I, alkyl having 1, 2, 3, 4, or 5 C atoms, cycloalkyl having 3, 4, 5, 6, 7, or 8 C atoms, —CN, —CF$_3$, —C$_2$F$_5$, —C$_3$F$_7$, —N$_3$, —NO$_2$, —Y—C$_s$H$_{2s}$—R(18), phenyl, thienyl, furyl, or an N-containing heterocycle having 1, 2, 3, 4, 5, 6, 7, 8 or 9 C atoms, where phenyl, thienyl, furyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, Y is —O—, —CO—, —CO—O—, —O—CO—, —S—, —SO—, —SO$_2$—, —O—SO$_2$—, —SO$_2$NR(10c)— or —CONR(10c)—, where the attachment to the benzene ring is, in each case, effected through the atom depicted on the left of each of the above groups, where R(10c) is hydrogen or alkyl having 1, 2, or 3 C atoms, s is zero, 1, 2, 3, 4, 5, or 6, R(18) is hydrogen, methyl, CF$_3$, C$_2$F$_5$, C$_3$F$_7$, cycloalkyl having 3, 4, 5, 6, 7, or 8 C atoms, —OR(21), —COOR(21), —NR(15a)R(16a), —CONR(15a)R(16a), phenyl, or an N-containing heterocycle having 1, 2, 3, 4, 5, 6, 7, 8, or 9 C atoms, where phenyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, R(15a) and R(16a) are the same or different and each is hydrogen or alkyl having 1, 2, 3, or 4 C atoms,
or
R(15a) and R(16a) together are a chain of 4 or 5 methylene groups, one CH$_2$ group of which is optionally replaced by —O—, —S—, —NH—, —N(CH$_3$)— or —N(benzyl)—, R(21) is hydrogen or alkyl having 1, 2, or 3 C atoms, R(9) is hydrogen or together with R(2) forms a bond, X is —CR(22)R(23)—, —O—, —NR(24)—, —S—, —SO—, or —SO$_2$—, R(22) and R(23) are the same or different and each is hydrogen, CF$_3$, alkyl having 1, 2, 3, 4, 5, or 6 C atoms, R(24) is hydrogen, alkyl having 1, 2, 3, 4, 5, or 6 C atoms, or phenyl, which is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, and 11) a compound of the formula XI, an isomer thereof, or a physiologically acceptable salt of any of the foregoing:

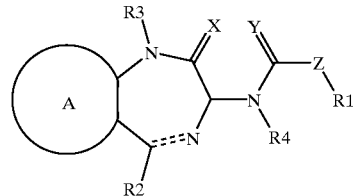

(XI)

where

A is substituted or unsubstituted thienyl or pyridyl,

X is O, S, =N—NH2, =N—OH, H2,

Y is O, NCN, H2,

Z is alkyl or alkenyl, unsubstituted or substituted by phenyl or cycloalkyl, where one or more CH$_2$ groups is optionally replaced by O, S, NH, or a bond, R1 is phenyl, unsubstituted or substituted, alkyl, cycloalkyl, a mono- or bicyclic heterocycle, or indanyl, R2 is phenyl, unsubstituted or substituted, alkyl, cycloalkyl, 2- or 3-furyl, or N-mono- or -bis-alkyl, R3 is H or alkyl, unsubstituted or substituted by N(CH$_3$)$_2$, OH, or fluoroalkyl;

R4 is H, alkyl which is optionally interrupted by one or two oxygen atoms; and 11) a compound of the formula XII, an isomer thereof, or a physiologically acceptable salt of any of the foregoing:

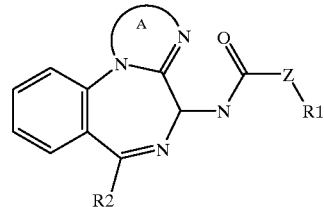

(XII)

where

A is a 2- or 3-membered chain consisting of C atoms, but in which one or more members is optionally nitrogen or oxygen, said chain being unsubstituted or substituted by alkyl, Z is alkyl or alkenyl,
which are unsubstituted or substituted by phenyl or cycloalkyl, and in which one or more CH$_2$ groups is optionally replaced by O, S, NH, a bond, or N-alkyl or N-phenyl;

R1 is phenyl, unsubstituted or substituted, alkyl, cycloalkyl, or a mono- or bicyclic heterocycle, R2 is phenyl, unsubstituted or substituted,
or
R2 is alkyl, cycloalkyl, 2- or 3-furyl, or N-mono- or -bis-alkyl; and 12) a compound of the formula XIII, an isomer thereof, or a physiologically acceptable salt of any of the foregoing:

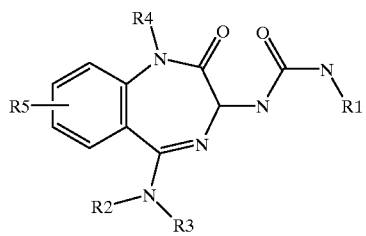

(XIII)

where

R1 is unsubstituted or substituted phenyl, or

R1 is alkyl, cycloalkyl, a mono- or bicyclic heterocycle, or indanyl,

R2 and R3 are the same or different and each is alkyl, which is unsubstituted or substituted by phenyl, or R2 and R3 are cycloalkyl or R2 and R3 together are an azacycle, R4 is alkyl, unsubstituted or substituted by phenyl, or R4 is phenyl or fluoroalkyl, R5 is H or alkyl; and 13) a compound of the formula XIV, an isomer thereof, or a physiologically acceptable salt of any of the foregoing:

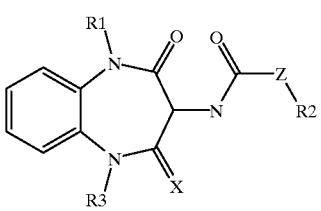

(XIV)

where

X is O or H2,

R1 is alkyl, cycloalkyl, fluoroalkyl, or oxo-substituted alkyl,

Z is unsubstituted or substituted alkyl, or

Z is alkenyl, cycloalkyl, cycloalkenyl, or a bond,

R2 is unsubstituted or substituted phenyl, or

R2 is cycloalkyl, unsubstituted or substituted,

R3 is alkyl, cycloalkyl, fluoroalkyl, or oxo-substituted; and 15) a compound of the formula XV, an isomer thereof, or a physiologically acceptable salt of any of the foregoing:

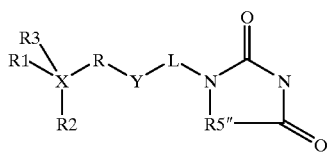

(XV)

where

X is a saturated or unsaturated 5-, 6-, or 7-membered heterocycle or carbocycle, R is a bond, a heteroatom, carbonyl, a heterocyclic ring, a carbocyclic ring, alkyl, alkenyl, alkoxy, alkylamino, arylalkyl, aryloxy, acyl, acyloxy, or acylamino, Y is a substituted or unsubstituted, saturated or unsaturated 5-, 6-, or 7-membered heterocyclic or carbocyclic ring, or a bond, R1, R2 and R3 are the same or different and each is H, Cl, F, Br, NH$_2$, CF$_3$, OH, SO$_3$H, CH$_3$SO$_2$NH, COOH, alkoxy, alkyl, alkoxycarbonyl, hydroxyalkyl, carboxyalkyl, aminoalkyl, acylamino, or acyloxy, L is alkylamino, alkenylamino, alkylimino, alkenylimino, or acylamino, where the nitrogen is attached to the nitrogen in position 1 of the 4-oxocyclic urea unit, R4 alkyl, alkenyl, alkynyl, alkylacyl, or heteroalkyl, A is substituted or unsubstituted, saturated or unsaturated alkyl or heteroalkyl, or a substituted or unsubstituted 5-, 6- or 7-membered heterocycle, R5 is alkyl; and 16) a compound of the formula XVI, an isomer thereof, or a physiologically acceptable salt of any of the foregoing:

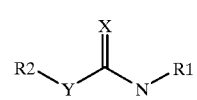

(XVI)

where

X is O, S, NH, NR, C—CN, N—OR, or N—NO$_2$,

Y is a bond, —C=C—, or NH,

R1 is alkyl, alkenyl, alkynyl, aryl, cycloalkyl, a heterocycle, or (heterocyclo)alkyl, R2 is aryl or a heterocycle; and 17) a compound of the formula XVII, an isomer thereof, or a physiologically acceptable salt of any of the foregoing:

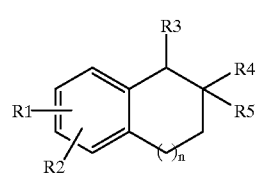

(XVII)

where

R1 is halogen, alkyl, alkenyl, alkynyl, cycloalkyl, aryl, (aryl)alkenyl, alkoxy, O-alkenyl, O-aryl, O-alkyl (heterocyclo), COO-alkyl, alkanoyl, CO-amino, CO-substituted amino, alkyl-CO-amino, alkyl-substituted amino, NHCO-alkyl, NHCO-aryl, NHCO-alkyl(heterocyclo), N(alkyl)CO-alkyl, N(alkyl)CO-aryl, N(alkyl)CO-heterocyclo, or N-(alkyl)CO-alkyl(heterocyclo), R2 is hydrogen, alkyl, halogen, aryl, alkoxy, amino, or substituted amino, R3 is oxo, hydroxyl, alkoxy, O—CO-alkyl, O—CO-aryl, O—CO-heterocyclo, NOH, NO-alkyl, N-amino, N-substituted amino, N—NHCONH-alkyl, N—NHSO$_2$-alkyl, N—NHSO$_2$-aryl, amino, substituted amino, NHCO-alkyl, NHCO-aryl, NHCO-heterocyclo, or spiroheterocyclo, R4 is hydrogen, alkyl, alkyl(CO-alkyl), or alkyl(COO-alkyl), or R3 and R4, together with the atom to which they are attached, form a 5- to 7-membered ring optionally containing up to three heteroatoms selected from O, N or S, R5 is hydrogen, alkyl, alkenyl, alkyl(heterocyclyl), alkyl-NHCO(alkyl), alkyl-NHCO(aryl), or alkyl-NHCO(alkylheterocyclyl), n is 0, 1, or 2.

Preference is given to the following compounds:

1) a chromane of the formula I, an isomer thereof, or a physiologically acceptable salt of any of the foregoing:

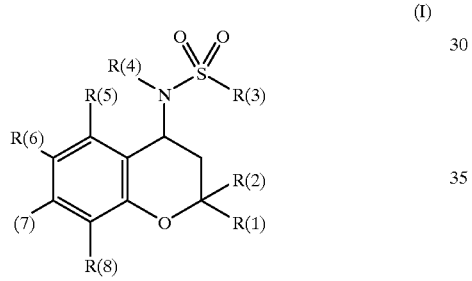

(I)

where

R(1) and R(2) are the same or different and each is hydrogen, $C_pF_{2p+1}$, alkyl having 1, 2, 3, 4, 5, or 6 C atoms, or phenyl, where any of the foregoing is unsubstituted or substituted by 1 or 2 substituents selected from F, Cl, Br, I, CF$_3$, methyl, methoxy, sulfamoyl, methylsulfonylamino, and methylsulfonyl, p is 1, 2, or 3, or R(1) and R(2) together are an alkylene chain having 2, 3, 4, 5, 6, 7, 8, 9, or 10 C atoms, R(3) is R(9)—$C_nH_{2n}$[NR(11)]$_m$—, R(9) is hydrogen or cycloalkyl having 3, 4, 5, 6, 7, or 8 C atoms, n is zero, 1, 2, 3, 4, 5, 6, 7, 8, 9, or 10, m is zero or 1, R(11) is hydrogen or alkyl having 1, 2, 3, 4, 5, or 6 C atoms, or R(11) together with R(9) is an alkylene group having 1, 2, 3, 4, 5, 6, 7, or 8 C atoms, where a CH$_2$ group of the group $C_nH_{2n}$ is optionally replaced by —O—, —SO$_q$, or —NR(10)—, q is zero, 1, or 2, R(10) is hydrogen, methyl, or ethyl, R(4) is R(12)—$C_rH_{2r}$, R(12) is hydrogen, cycloalkyl having 3, 4, 5, 6, 7, or 8 C atoms, piperidyl, 1-pyrrolidinyl, N-morpholino, N-methylpiperazino, $C_pF_{2p+1}$, pyridyl, thienyl, imidazolyl, or phenyl, where any of the foregoing is unsubstituted or substituted by 1 or 2 substituents selected from F, Cl, Br, I, CF$_3$, methyl, methoxy, sulfamoyl, methylsulfonyl, or methylsulfonylamino, r is 1, 2, 3, 4, 5, 6, 7, 8, 9, 10, 11, 12, 13, 14, 15, 16, 17, 18, 19, or 20, where a CH$_2$ group of the group $C_rH_{2r}$ is optionally replaced by —O—, —HC=CH—, —C≡C—, —CO—, —CO—O—, —SO$_q$—, or —NR(10)—, q is zero, 1, or 2, R(10) is hydrogen, methyl, or ethyl, R(5), R(6), R(7) and R(8) are the same or different and each is hydrogen, F, Cl, Br, I, alkyl having 1, 2, 3, or 4 C atoms, cycloalkyl having 3, 4, 5, 6, 7, or 8 C atoms, —CN, —CF$_3$, —C$_2$F$_5$, —C$_3$F$_7$, —N$_3$, —NO$_2$, —CONR(13)R(14), —COOR(15), R(16)—$C_sH_{2s}$—Y—, or phenyl, where any of the foregoing is unsubstituted or substituted by 1 or 2 substituents selected from F, Cl, Br, I, CF$_3$, methyl, methoxy, sulfamoyl, and methylsulfonyl, R(13) and R(14) are the same or different and each is hydrogen or alkyl having 1, 2, or 3 C atoms, R(15) is hydrogen, methyl, ethyl, phenyl, or —$C_uH_{2u}$—NR(13)R(14), u is 2 or 3, R(16) is hydrogen, cycloalkyl having 3, 4, 5, 6, 7, or 8 C atoms, —COOR(15), thienyl, imidazolyl, pyridyl, quinolyl, isoquinolyl, piperidyl, 1-pyrrolidinyl, N-morpholino, N-methylpiperazino, $C_tF_{2t+1}$, or phenyl, where any of the foregoing is unsubstituted or substituted by 1 or 2 substituents selected from F, Cl, Br, I, CF$_3$, methyl, methoxy, sulfamoyl, or methylsulfonyl, s is zero, 1, 2, 3, 4, 5, or 6, t is 1, 2, or 3, Y is SO$_q$, —CO—, —SO$_2$—NR(10)—, —O—, —NR(10)—, or —CO—NR(10), with the proviso that R(6) is other than —OCF$_3$, or —OC$_2$F$_5$, and 2) a compound of the formula II, an isomer thereof, or a physiologically acceptable salt of any of the foregoing:

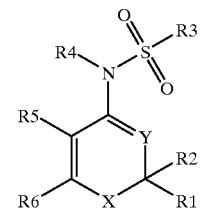

(II)

where

X is —O—, —S—, —SO—, —SO$_2$—, —NR(7)—, —CR(8a)R(8b)—, or —CO—,

R(7) is hydrogen or —(C$_a$H$_{2a}$)—R(9), where a CH$_2$ group of the groups $C_aH_{2a}$ is optionally replaced by —O—, —CH=CH—, —C≡C—, —CO—, —CO—O—, —O—CO—, —S—, —SO—, —SO$_2$—, NR(10)—, or —CONR(10)—, R(10) is hydrogen or alkyl having 1, 2, or 3 C atoms, a is zero, 1, 2, 3, 4, 5, 6, 7, or 8, R(9) is hydrogen, $CF_3$, $C_2F_5$, $C_3F_7$, cycloalkyl having 3, 4, 5, 6, 7, or 8 C atoms, dimethylamino, diethylamino, 1-piperidyl, 1-pyrrolidinyl, 4-morpholinyl, 4-methylpiperazin-1-yl, pyridyl, thienyl, imidazolyl, or phenyl, where pyridyl, thienyl, imidazolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(7) and R(1) together form a bond, R(8a) is hydrogen, $CF_3$, $C_2F_5$, $C_3F_7$, alkyl having 1, 2, 3, 4, 5, or 6 C atoms, or phenyl, where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(8b) is hydrogen, alkyl having 1, 2, or 3 C atoms, —OR(10), —COOR(10), or CO—R(10), where R(10) is hydrogen or alkyl having 1, 2, or 3 C atoms;

or one of the radicals R(8a) or R(8b) together with R(1) forms a bond,

Y is N or CR(11),

R(11) is hydrogen or alkyl having 1, 2, or 3 C atoms

R(1) and R(2) are identical or different and each is hydrogen, $CF_3$, $C_2F_5$, $C_3F_7$, F, Cl, methoxy, alkyl having 1, 2, 3, 4, 5, or 6 C atoms, or phenyl, where each of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(1) and R(2) together form an alkylene chain having 2, 3, 4, 5, 6, 7, 8, 9, or 10 C atoms, R(3) is R(12)—$C_nH_{2n}$—NR(13)— or R(12)—$C_nH_{2n}$—, where one $CH_2$ group in the groups $C_nH_{2n}$ is optionally replaced by —O—, —CO—, —S—, —SO—, —$SO_2$—, or —NR(10a)—, where R(10a) is hydrogen, methyl, or ethyl, R(12) is hydrogen, methyl, cycloalkyl having 3, 4, 5, 6, 7, or 8 C atoms, $CF_3$, $C_2F_5$, or $C_3F_7$, n is zero, 1, 2, 3, 4, 5, 6, 7, 8, 9, or 10, R(13) is hydrogen or alkyl having 1, 2, 3, 4, 5, or 6 C atoms, or R(12) and R(13) together form a bond if n is greater than 3, or R(3) and R(4) together form an alkylene chain having 3, 4, 5, 6, 7 or 8 C atoms, where one $CH_2$ group of the alkylene chain is optionally replaced by —O—, —CO—, —S—, —SO—, —$SO_2$—, or —NR(10a)—, where R(10a) is hydrogen, methyl, or ethyl, R(4) is R(14)—$C_rH_{2r}$, where one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(10b)—, or —CONR(10b)—, where R(10b) is hydrogen or alkyl having 1, 2, or 3 C atoms, R(14) is methyl, $CF_3$, $C_2F_5$, $C_3F_7$, cycloalkyl having 3, 4, 5, 6, 7, or 8 C atoms, —OH, —COOH, —NR(23)R(24), 1-piperidyl, 1-pyrrolidinyl, 4-morpholinyl, 4-methylpiperazin-1-yl, pyridyl, thienyl, imidazolyl, or phenyl, where pyridyl, thienyl, imidazolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(23) and R(24) are the same or different and each is hydrogen or alkyl having 1, 2, or 3 C atoms, or R(23) and R(24) together form a chain of 4 or 5 methylene groups, one $CH_2$ group of which is optionally replaced by —O—, —S—, —NH—, —N($CH_3$)—, or —N(benzyl)—, r is zero, 1, 2, 3, 4, 5, 6, 7, 8, 9, 10, 11, 12, 13, 14, 15, 16, 17, 18, 19, or 20, R(5) and R(6) together form a group —CR(15)=CR(16)—CR(17)=CR(18)—,
—CR(15)=CR(16)—CR(17)=N—,
—CR(15)=CR(16)—N=CR(18)—,
—CR(15)=N—CR(17)=N—,
—CR(15)=N—N=CR(18)—,
—N=CR(16)—CR(17)=N—, and
—CR(15)=CR(16)—, where either end of said group is attached to the ring at the R(5) position, R(15), R(16), R(17) and R(18) are the same or different and each is hydrogen, F, Cl, Br, I, alkyl having 1, 2, 3, 4, or 5 C atoms, cycloalkyl having 3, 4, 5, 6, 7, or 8 C atoms, —CN, —$CF_3$, —$C_2F_5$, —$C_3F_7$, —$N_3$, —$NO_2$, —Z—$C_sH_{2s}$—R(22), thienyl, or phenyl, wherein each of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;

Z is —O—, —CO—, —CO—O—, —O—CO—, —S—, —SO—, —$SO_2$—, —$SO_2$—O—, —$SO_2$NR(10c), —NR(10c)—, or —CONR(10c)—, where R(10c) is hydrogen or alkyl having 1, 2 or 3 C atoms;

s is zero, 1, 2, 3, 4, 5, or 6,

R(22) is hydrogen, $CF_3$, $C_2F_5$, $C_3F_7$, cycloalkyl having 3, 4, 5, 6, 7, or 8 C atoms, —NR(19)R(20), —COOR(21), 1-piperidyl, 1-pyrrolidinyl, 4-morpholinyl, 4-methylpiperazin-1-yl, pyridyl, thienyl, imidazolyl, quinolyl, isoquinolyl, or phenyl, where pyridyl, thienyl, imidazolyl, quinolyl, isoquinolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(19) and R(20) are the same or different and each is hydrogen or alkyl having 1, 2, or 3 C atoms,
or
R(19) and R(20) together form a chain of 4 or 5 methylene groups, one CH$_2$ group of which is optionally replaced by —O—, —S—, —NH—, —N(CH$_3$)—, or —N(benzyl)—,
R(21) is hydrogen or alkyl having 1, 2, or 3 C atoms,
with the proviso that Y is other than CR(11) when X is O; and 3) a compound of the formula III, an isomer thereof, or a physiologically acceptable salt of any of the foregoing:

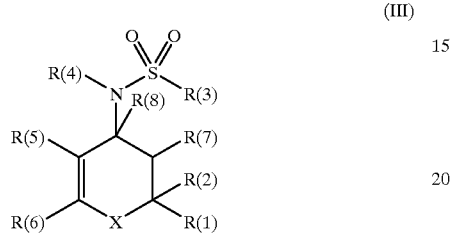

(III)

in which:
X is —[S(O)$_{zero, 1\ or\ 2}$]—, —NR(9)—, —[CR(9)R(23)]—, or —CO—,
R(9) is hydrogen or —(C$_n$H$_{2n}$)—R(10),
n is zero, 1, 2, 3, 4, 5, 6, 7 or 8,
R(10) is hydrogen, cycloalkyl having 3, 4, 5, 6, 7, or 8 C atoms, piperidyl, 1-pyrrolidinyl, N-morpholino, N-methylpiperazino, CF$_3$, C$_2$F$_5$ or C$_3$F$_7$, where one CH$_2$ group of the group C$_n$H$_{2n}$ is optionally replaced by —O—, —CH=CH—, —C≡C—, —CO—, —CO—O—, —[SO$_{zero, 1\ or\ 2}$]—, or —NR(11)—,
R(11) is hydrogen, methyl, or ethyl,
or
R(10) is pyridyl, thienyl, imidazolyl, or phenyl, which are unsubstituted or substituted by 1 or 2 substituents selected from F, Cl, Br, I, CF$_3$, methyl, methoxy, sulfamoyl, methylsulfonyl, and methylsulfonylamino,
or
R(9) together with R(1) forms a bond;
R(23) is hydrogen, alkyl having 1, 2, or 3 C atoms, OH, O-alkyl having 1, 2, or 3 C atoms, COOH, COO-alkyl having 1, 2, or 3 C atoms, or —CO—R(24); R(24) is hydrogen, methyl, or ethyl,
R(1) and R(2) are the same or different and each is hydrogen, CF$_3$, C$_2$F$_5$, C$_3$F$_7$, alkyl having 1, 2, 3, 4, 5, or 6 C atoms, or phenyl, where any of the foregoing is unsubstituted or substituted by 1 or 2 substituents selected from F, Cl, Br, I, CF$_3$, methyl, methoxy, sulfamoyl and methylsulfonyl,
or
R(1) and R(2) together are an alkylene chain having 2, 3, 4, 5, 6, 7, 8, 9, or 10 C atoms,
R(3) is R(12)—C$_a$H$_{2a}$[NR(13)]$_m$—,
R(12) is hydrogen or cycloalkyl having 3, 4, 5, 6, 7, or 8 C atoms, CF$_3$, C$_2$F$_5$, or C$_3$F$_7$,
a is zero, 1, 2, 3, 4, 5, 6, 7, 8, 9, or 10,
m is zero or 1,
R(13) is hydrogen or alkyl having 1, 2, 3, 4, 5, or 6 C atoms,
or
R(12) and R(13) together are an alkylene group having 4, 5, 6, 7, or 8 C atoms where one CH$_2$ group of the alkylene group is optionally replaced by —O—, —[SO$_{zero, 1\ or\ 2}$]—, —CO—, or —NR(11)—, where R(11) is hydrogen, methyl, or ethyl,
R(4) is R(14)—C$_r$H$_{2r}$,
r is 1, 2, 3, 4, 5, 6, 7, 8, 9, 10, 11, 12, 13, 14, 15, 16, 17, 18, 19, or 20;
R(14) is hydrogen, cycloalkyl having 3, 4, 5, 6, 7, or 8 C atoms, piperidyl, 1-pyrrolidinyl, N-morpholino, N-methylpiperazino, CF$_3$, C$_2$F$_5$, C$_3$F$_7$, pyridyl, thienyl, imidazolyl, or phenyl,
which is unsubstituted or substituted by 1 or 2 substituents selected from F, Cl, Br, I, CF$_3$, methyl, methoxy, sulfamoyl, methylsulfonyl, and methylsulfonylamino,
where one CH$_2$ group of the group C$_r$H$_{2r}$ is optionally replaced by —O—, —CH=CH—, —C≡C—, —CO—, —CO—O—, —CO—NR(11)—, —[SO$_{zero, 1\ or\ 2}$]—, or —NR(11)—;
or
R(3) and R(4) together form an alkylene chain having 3, 4, 5, 6, 7, or 8 C atoms, where one CH$_2$ group of the alkylene chain is optionally replaced by —O—, —[SO$_{zero, 1\ or\ 2}$]—, —CO—, or —NR(11)—,
R(5) and R(6) together are —CR(15)=CR(16)—CR(17)=CR(18)—, —CR(15)=CR(16)—CR(17)=N—, —CR(15)=CR(16)—N=CR(18)—, —CR(15)=N—CR(17)=N—, —CR(15)=N—N=CR(18)—, —N=CR(16)—CR(17)=N—, or —S—CR(15)=CR(16)—, R(15), R(16), R(17) and R(18)
are the same or different and each is hydrogen, F, Cl, Br, I, alkyl having 1, 2, 3, or 4 C atoms, cycloalkyl having 3, 4, 5, 6, 7, or 8 C atoms, CN, CF$_3$, C$_2$F$_5$, C$_3$F$_7$, N$_3$, NO$_2$, —CONR(19)R(20), —COOR(21), R(22)—C$_s$H$_{2s}$—Z—, or phenyl,
where any of the foregoing is unsubstituted or substituted by 1 or 2 substituents selected from F, Cl, Br, I, CF$_3$, methyl, methoxy, sulfamoyl, and methylsulfonyl,
R(19) and R(20) are the same or different and each is hydrogen or alkyl having 1, 2, or 3 C atoms,
R(21) is hydrogen, methyl, ethyl, phenyl, or —C$_u$H$_{2u}$—NR(19)R(20),
u is 2 or 3,
where the phenyl is unsubstituted or substituted by 1 or 2 substituents selected from F, Cl, Br, I, CF$_3$, methyl, methoxy, sulfamoyl, or methylsulfonyl,
R(22) is hydrogen, cycloalkyl having 3, 4, 5, 6, 7, or 8 C atoms, —COOR(21), thienyl, imidazolyl, pyridyl, quinolyl, isoquinolyl, piperidyl, 1-pyrrolidinyl, N-morpholino, N-methylpiperazino, CF$_3$, C$_2$F$_5$, C$_3$F$_7$, or phenyl,
where any of the foregoing is unsubstituted or substituted by 1 or 2 substituents selected from F, Cl, Br, I, CF$_3$, methyl, methoxy, sulfamoyl or methylsulfonyl,
s is zero, 1, 2, 3, 4, 5, or 6,
Z is —[S(O)$_{zero, 1\ or\ 2}$]—, —CO—, —SO$_2$—NR(11)—, —SO$_2$—O—, —O—, —NR(11)—, or —[CO—NR(11)]—,
R(7) is hydrogen, hydroxyl, alkoxy having 1, 2, 3, or 4 C atoms, acyloxy having 1, 2, 3, or 4 C atoms, Cl, Br, F, alkyl having 1, 2, 3, or 4 C atoms,
R(8) is hydrogen or alkyl having 1, 2, 3, 4, 5, or 6 C atoms; and 4) a chromane derivative of the formula IV, an isomer thereof, or a physiologically acceptable salt thereof:

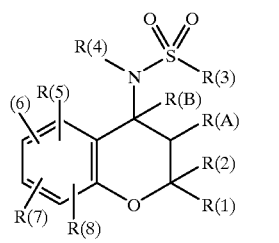

(IV)

where
R(1) and R(2) are the same or different and each is hydrogen, CF$_3$, C$_2$F$_5$, C$_3$F$_7$, alkyl having 1, 2, 3, 4, 5, or 6 C atoms, or phenyl,
where any of the foregoing is unsubstituted or substituted by 1 or 2 substituents selected from F, Cl, Br, I, CF$_3$, methyl, methoxy, sulfamoyl, and methylsulfonyl,
or
R(1) and R(2) together form an alkylene chain having 2, 3, 4, 5, 6, 7, 8, 9, or 10 C atoms,
R(A) is hydroxyl, alkanoyloxy having 1, 2, 3, 4, 5, or 6 C atoms, or alkylsulfonyloxy having 1, 2, 3, 4, 5, or 6 C atoms,
R(B) is hydrogen,
or
R(A) and R(B) together form a bond;
R(3) is R(9)—C$_n$H$_{2n}$[NR(11)]$_m$—,
R(9) is hydrogen or cycloalkyl having 3, 4, 5, 6, 7, or 8 C atoms,
n is zero, 1, 2, 3, 4, 5, 6, 7, 8, 9, or 10,
m is zero or 1,
R(11) is hydrogen or alkyl having 1, 2, 3, 4, 5, or 6 C atoms,
or
R(11) and R(9) together form an alkylene group having 1, 2, 3, 4, 5, 6, 7, or 8 C atoms,
where one CH$_2$ group of the group C$_n$H$_{2n}$ is optionally replaced by —O—, SO$_{zero,\ 1\ or\ 2}$— or —NR(10),
R(10) is hydrogen, methyl, or ethyl,
R(4) is R(12)—C$_r$H$_{2r}$,
R(12) is hydrogen, cycloalkyl having 3, 4, 5, 6, 7, or 8 C atoms, piperidyl, 1-pyrrolidinyl, N-morpholino, N-methylpiperazino, CF$_3$, C$_2$F$_5$, C$_3$F$_7$, pyridyl, thienyl, imidazolyl or phenyl,
where pyridyl, thienyl, imidazolyl, or phenyl are unsubstituted or substituted by 1 or 2 substituents selected from F, Cl, Br, I, CF$_3$, methyl, methoxy, sulfamoyl, methylsulfonyl, and methylsulfonylamino,
r is zero, 1, 2, 3, 4, 5, 6, 7, 8, 9, 10, 11, 12, 13, 14, 15, 16, 17, 18, 19, or 20,
where one CH$_2$ group of the group C$_r$H$_{2r}$ is optionally replaced by —O—, >CH=CH<, —C≡C—, —CO—, —CO—O—, SO$_{zero,\ 1\ or\ 2}$— or —NR(10)—,
R(5), R(6), R(7) and R(8) are the same or different and each is hydrogen, F, Cl, Br, I, alkyl having 1, 2, 3, 4, 5 or 6 C atoms, cycloalkyl having 3, 4, 5, 6, 7 or 8 C atoms, —CN, —CF$_3$, —C$_2$F$_5$, —C$_3$F$_7$, —N$_3$, —NO$_2$, —CONR(13)R(14), —COOR(15), R(16)—C$_s$H$_{2s}$—Y—, or phenyl,
where any of the foregoing is unsubstituted or substituted by 1 or 2 substituents selected from F, Cl, Br, I, CF$_3$, methyl, methoxy, sulfamoyl, and methylsulfonyl,
R(13) and R(14) are the same or different and each is hydrogen or alkyl having 1, 2, or 3 C atoms,
R(15) is hydrogen, methyl, ethyl, phenyl, or —C$_u$H$_{2u}$—NR(13)R(14),
u is 2 or 3,
R(16) is hydrogen, cycloalkyl having 3, 4, 5, 6, 7, or 8 C atoms, —COOR(15), thienyl, imidazolyl, pyridyl, quinolyl, isoquinolyl, piperidyl, 1-pyrrolidinyl, N-morpholino, N-methylpiperazino, CF$_3$, C$_2$F$_5$, C$_3$F$_7$, or phenyl,
where any of the foregoing is unsubstituted or substituted by 1 or 2 substituents selected from F, Cl, Br, I, CF$_3$, methyl, methoxy, sulfamoyl, and methylsulfonyl,
s is zero, 1, 2, 3, 4, 5, or 6,
Y —S—, —SO—, —SO$_2$—, —CO—, —SO$_2$—NR(10)—, —O—, —NR(10)—, or —CO—NR(10),
but with the proviso that two of the substituents R(5), R(6), R(7) and R(8) are other than hydrogen; and
5) a compound of the formula V, an isomer thereof, or a physiologically acceptable salt thereof:

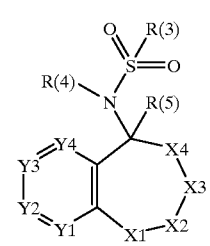

(V)

where
X1 is —O—, —S—, —SO—, —SO$_2$—, —CR(1)R(2)—, —NR(6)—, —CO—, or —CR(1)R(7)—,
R(1) and R(2) are the same or different and each is hydrogen, CF$_3$, C$_2$F$_5$, C$_3$F$_7$, alkyl having 1, 2, 3, 4, 5 or 6 C atoms, or phenyl,
where any of the foregoing is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino,
or
R(1) and R(2) together form an alkylene chain having 2, 3, 4, 5, 6, 7, 8, 9, or 10 C atoms,
R(6) is hydrogen or —C$_n$H$_{2n}$—R(8),
where one CH$_2$ group of the group C$_n$H$_{2n}$ is optionally replaced by —O—, —CH=CH—, —C≡C—, —CO—, —CO—O—, —O—CO—, —S—, —SO—, —SO$_2$—, —NR(9)—, or —CONR(9)—, R(9) is hydrogen or alkyl having 1, 2, or 3 C atoms,
n is zero, 1, 2, 3, 4, 5, 6, 7, or 8,
R(8) is hydrogen, CF$_3$, C$_2$F$_5$, C$_3$F$_7$, cycloalkyl having 3, 4, 5, 6, 7, or 8 C atoms, dimethylamino, diethylamino, 1-piperidyl, 1-pyrrolidinyl, 4-morpholinyl, 4-methylpiperazin-1-yl, pyridyl, thienyl, imidazolyl, or phenyl,
where pyridyl, thienyl, imidazolyl and phenyl are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino;

X2 is —CR(1)R(2)— or —CR(2)R(10)—, or

X2 is —O—, —S—, —SO—, —SO$_2$— or —NR(6)—, where the radicals R(1), R(2), and R(6) are as defined under X1, and the radicals R(1), R(2), and R(6) in X2 are the same or different as X1;

R(10) together with R(7) form a bond,

X3 is —CR(1)R(2)—, or

X3 is also —O—, —S—, —SO—, —SO$_2$—, or —NR(6)—, where the radicals R(1), R(2), and R(6) are as defined under X1, and the radicals R(1), R(2), and R(6) in X2 are the same or different as X1;

X4 is —CR(1)R(2)—, —NR(6)—, —NR(11)—, —CH(OR(30))—, or —CR(2)R(11)—, where the radicals R(1), R(2), and R(6) are as defined under X1, and the radicals R(1), R(2), and R(6) in X2 are the same or different as X1;

R(30) is hydrogen, alkyl having 1, 2, or 3 C atoms, or acyl having 1, 2, 3, or 4 C atoms, R(11) together with R(5) forms a bond, Y1, Y2, Y3, and Y4 are the same or different and each is —CR(12)— or N, where at most 2 of the groups Y1, Y2, Y3 and Y4 are optionally simultaneously N, the radicals R(12) are the same or different and each is hydrogen, F, Cl, Br, I, alkyl having 1, 2, 3, 4, or 5 C atoms, cycloalkyl having 3, 4, 5, 6, 7, or 8 C atoms, CN, CF$_3$, C$_2$F$_5$, C$_3$F$_7$, N$_3$, NO$_2$, —Z—C$_m$H$_{2m}$—R(13), or phenyl, which is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl and methylsulfonylamino;

Z is —O—, —CO—, —CO—O—, —O—CO—, —S—, —SO—, —SO$_2$—, —SO$_2$NR(14)—, —NR(14)— or —CONR(14)—,

R(14) is hydrogen or alkyl having 1, 2, or 3 C atoms;

m is zero, 1, 2, 3, 4, 5, or 6,

R(13) is hydrogen, CF$_3$, C$_2$F$_5$, C$_3$F$_7$, cycloalkyl having 3, 4, 5, 6, 7 or 8 C atoms, —NR(15)R(16), —CONR(15)R(16), —OR(30a), phenyl, thienyl or an N-containing heterocycle having 1, 2, 3, 4, 5, 6, 7, 8 or 9 C atoms, where phenyl, thienyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl and methylsulfonylamino, R(15) and R(16) are the same or different and each is hydrogen or alkyl having 1, 2 or 3 C atoms, or R(15) and R(16) together are a chain of 4 or 5 methylene groups, one CH$_2$ group of which is optionally replaced by —O—, —S—, —NH—, —N(CH$_3$)— or —N(benzyl)—, R(30a) is hydrogen, alkyl having 1, 2, or 3 C atoms or acyl having 1, 2, 3, or 4 C atoms, or Y1 and Y2 together are an S atom and Y3 and Y4 are each —CR(12)—, the radicals R(12) are the same or different and each is as defined under Y1, Y2, Y3, Y4, R(3) is R(17)—C$_x$H$_{2x}$—NR(18)— or R(17)—C$_x$H$_{2x}$—, where one CH$_2$ group in the groups C$_x$H$_{2x}$ is optionally replaced by —O—, —CO—, —S—, —SO—, —SO$_2$— or —NR(19)—, R(19) is hydrogen, methyl or ethyl, R(17) is hydrogen, methyl, cycloalkyl having 3, 4, 5, 6, 7 or 8 C atoms, CF$_3$, C$_2$F$_5$ or C$_3$F$_7$, x is zero, 1, 2, 3, 4, 5, 6, 7, 8, 9 or 10, R(18) is hydrogen or alkyl having 1, 2, 3, 4, 5, 6, 7 or 8 C atoms, or R(18) and R(17) together form a bond if x is 3 or greater, or R(3) is phenyl, which is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, or R(3) together with R(4) form an alkylene chain having 3, 4, 5, 6, 7, or 8 C atoms, where one CH$_2$ group of the alkylene chain is optionally replaced by —O—, —CO—, —S—, —SO, or SO$_2$, R(4) is —C$_r$H$_{2r}$—R(20), where one CH$_2$ group of the group C$_r$H$_{2r}$ is optionally replaced by —O—, —CH═CH—, —C≡C—, —CO—, —CO—O—, —O—CO—, —S—, —SO—, —SO$_2$—, —NR(21)—, or —CONR(21)—, R(21) is hydrogen or alkyl having 1, 2, or 3 C atoms;

r is zero, 1, 2, 3, 4, 5, 6, 7, 8, 9, 10, 11, 12, 13, 14, 15, 16, 17, 18, 19, or 20, R(20) is hydrogen, methyl, CF$_3$, C$_2$F$_5$, C$_3$F$_7$, cycloalkyl having 3, 4, 5, 6, 7, or 8 C atoms, —NR(22)R(23), phenyl, thienyl, or an N-containing heterocycle having 1, 2, 3, 4, 5, 6, 7, 8, or 9 C atoms, where phenyl, thienyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, R(22) and R(23) are the same or different and each is hydrogen or alkyl having 1, 2, or 3 C atoms, or R(22) and R(23) together form a chain of 4 or 5 methylene groups one CH$_2$ group of which is optionally replaced by —O—, —S—, —NH—, —N(CH$_3$)—, or —N(benzyl)—, R(5) is hydrogen or together with R(11) forms a bond; and 6) a compound of the formula VI, an isomer thereof, or a physiologically acceptable salt thereof,

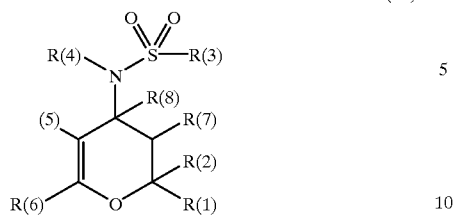

(VI)

where
R(1) and R(2) are the same or different and each is a hydrogen, $CF_3$, $C_2F_5$, $C_3F_7$, alkyl having 1, 2, 3, 4, 5, or 6 C atoms, or phenyl,
  where any of the foregoing is unsubstituted or substituted by 1 or 2 substituents selected from F, Cl, Br, I, $CF_3$, methyl, methoxy, sulfamoyl, and methylsulfonyl,
or
R(1) and R(2) together are an alkylene chain having 2, 3, 4, 5, 6, 7, 8, 9, or 10 C atoms,
  where one $CH_2$ group of the alkylene chain is optionally replaced by —O—, —CO—, —S—, —SO—, —$SO_2$—, or —NR(10)—, R(10) is hydrogen or alkyl having 1, 2, or 3 C atoms,
R(3) is R(12)—$C_aH_{2a}$[NR(13)]$_m$—,
  R(12) is hydrogen or cycloalkyl having 3, 4, 5, 6, 7, or 8 C atoms, $CF_3$, $C_2F_5$, or $C_3F_7$,
  a is zero, 1, 2, 3, 4, 5, 6, 7, 8, 9, or 10,
  m is zero or 1,
  R(13) is hydrogen or alkyl having 1, 2, 3, 4, 5, or 6 C atoms,
  or
  R(12) and R(13) together form an alkylene group having 4, 5, 6, 7 or 8 C atoms,
    where one $CH_2$ group of the alkylene group is optionally replaced by —O—, —[$SO_{zero,\ 1\ or\ 2}$]—, —CO— or —NR(10)—; R(10) is hydrogen or alkyl having 1, 2 or 3 C atoms;
R(4) R(14)—$C_rH_{2r}$,
  r is zero, 1, 2, 3, 4, 5, 6, 7, 8, 9, 10, 11, 12, 13, 14, 15, 16, 17, 18, 19, or 20,
  R(14) is hydrogen, cycloalkyl having 3, 4, 5, 6, 7, or 8 C atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
    where any of the foregoing is unsubstituted or substituted by 1 or 2 substituents selected from F, Cl, Br, I, $CF_3$, methyl, methoxy, sulfamoyl, methylsulfonyl and methylsulfonylamino,
  where one $CH_2$ group of the group $C_rH_{2r}$ is optionally replaced by —O—, —CH=CH—, —C C—, —CO—, —CO—O—, —CO—NR(11)—, —[$SO_{zero,\ 1\ or\ 2}$]— or —NR(11)—,
  R(11) is hydrogen or —($C_aH_{2a}$)—R(10),
    where one $CH_2$ group of the group $C_aH_{2a}$ is optionally replaced by —O—, —CH=CH—, —C≡C—, —CO—, —CO—O—, —O—CO—, —S—, —SO—, —$SO_2$—, NR(10)—, or —CONR(10)—, R(10) is hydrogen or alkyl having 1, 2, or 3 C atoms,
or
R(3) and R(4) together are an alkylene chain having 3, 4, 5, 6, 7, or 8 C atoms,
  where one $CH_2$ group of the alkylene chain is optionally replaced by —O—, —[$SO_{zero,\ 1\ or\ 2}$]—, —CO—, or —NR(11)—, R(11) is hydrogen or —($C_aH_{2a}$)—R(10),
  where one $CH_2$ group of the group $C_aH_{2a}$ is optionally replaced by —O—, —CH=CH—, —C≡C—, —CO—, —CO—O—, —O—CO—, —S—, —SO—, —$SO_2$—, NR(10)—, or —CONR(10)—,
R(10) is hydrogen or alkyl having 1, 2 or 3 C atoms,
R(5) and R(6) are
  —CR(15)=CR(16)—CR(17)=N—,
  —CR(15)=CR(16)—N=CR(17)—,
  —CR(15)=N—CR(17)=N—,
  —CR(15)=N—N=CR(17)—,
  —N=CR(16)—CR(17)=N—, or
  —S—CR(15)=CR(16)—;
R(15), R(16) and R(17) are the same or different and each is hydrogen, F, Cl, Br, I, alkyl having 1, 2, 3, or 4 C atoms, cycloalkyl having 3, 4, 5, 6, 7, or 8 C atoms, CN, $CF_3$, $C_2F_5$, $C_3F_7$, $N_3$, $NO_2$, —CONR(19)R(21), —COOR(21), R(22)—$C_sH_{2s}$—Z—, or phenyl,
  where any of the foregoing is unsubstituted or substituted by 1 or 2 substituents selected from F, Cl, Br, I, $CF_3$, methyl, methoxy, sulfamoyl and methylsulfonyl,
R(19) is hydrogen or alkyl having 1, 2, or 3 C atoms,
R(21) is hydrogen, methyl, ethyl, phenyl, or —$C_uH_{2u}$—NR(19)R(20),
  where the phenyl is unsubstituted or substituted by 1 or 2 substituents selected from F, Cl, Br, I, $CF_3$, methyl, methoxy, sulfamoyl and methylsulfonyl,
R(20) is hydrogen or alkyl having 1, 2, or 3 C atoms,
u is 2 or 3,
R(22) is hydrogen, cycloalkyl having 3, 4, 5, 6, 7, or 8 C atoms, —COOR(21), CONR(19)R(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
  where any of the foregoing is unsubstituted or substituted by 1 or 2 substituents selected from F, Cl, Br, I, $CF_3$, methyl, methoxy, sulfamoyl, and methylsulfonyl,
s is zero, 1, 2, 3, 4, 5, or 6,
Z is —[$S(O)_{zero,\ 1\ or\ 2}$]—, —CO—, —$SO_{(0,\ 1\ or\ 2)}$—NR(11)—, —$SO_2$—O—, —O—, —NR(11)—, or —[CO—NR(11)]—,
R(7) is hydrogen, hydroxyl, alkoxy having 1, 2, 3, or 4 C atoms, acyloxy having 1, 2, 3, or 4 C atoms, Cl, Br, F, alkyl having 1, 2, 3, or 4 C atoms,
R(8) is hydrogen or alkyl having 1, 2, 3, 4, 5, or 6 C atoms; and 7) a compound of the formula VII, an isomer thereof, or a physiologically acceptable salt of any of the foregoing:

(VII)

[Structure VII: chroman ring with R(4),R(5) on N-SO2-R(3) at position 4, B, R(9), R(2), R(1), R(6), R(7), R(8) substituents]

where

R(1) and R(2) are the same or different and each is hydrogen, $CF_3$, $C_2F_5$, $C_3F_7$, alkyl having 1, 2, 3, 4, 5, or 6 C atoms, or phenyl,
 which is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(1) and R(2) together form an alkylene chain having 2, 3, 4, 5, 6, 7, 8, 9, or 10 C atoms, R(3) is R(10)—$C_nH_{2n}$—NR(11)— or R(10)—$C_nH_{2n}$—,
 where one $CH_2$ group in the groups $C_nH_{2n}$ is optionally replaced by —O—, —CO—, —S—, —SO—, —$SO_2$—, or —NR(12a)—,
 R(12a) is hydrogen, methyl, or ethyl,
 R(10) is hydrogen, methyl, cycloalkyl having 3, 4, 5, 6, 7, or 8 C atoms, $CF_3$, $C_2F_5$ or $C_3F_7$,
 n is zero, 1, 2, 3, 4, 5, 6, 7, 8, 9, or 10,
 R(11) is hydrogen or alkyl having 1, 2, 3, 4, 5, or 6 C atoms,
 or
 R(10) and R(11) together form a bond if n is 3 or greater, R(4) is R(13)—$C_rH_{2r}$—Z—$C_qH_{2q}$—,
 q is 0, 1, 2, 3, 4, 5, 6, 7, or 8,
 r is 0, 1, 2, 3, 4, 5, 6, 7, or 8,
 Z is —CO—NR(14)—,
  —OCO—NR(14)—,
  —O—$C_xH_{2x}$—O—,
  —O—$C_xH_{2x}$—NR(14)—,
  —O—$C_xH_{2x}$—CO—O,
  —CO—O—$C_xH_{2x}$—O— or
  —CO—O—$C_xH_{2x}$—NR(14)—,
   where in each case either end of the groups defined by Z is attached to $C_qH_{2q}$—;
 x is 2, 3, or 4,
 R(14) is hydrogen, alkyl having 1, 2, or 3 C atoms, —$C_yH_{2y}$—OR(12b), —$C_yH_{2y}$—NR(12b)$_2$,
 R(12b) is hydrogen, methyl or ethyl,
 y is 2 or 3,
 R(13) is H, $CF_3$, $C_2F_5$, $C_3F_7$, cycloalkyl having 3, 4, 5, 6, 7, or 8 C atoms, —NR(15)R(16), —CONR(15)R(16), —C(=NR(17))NR(15)R(16), —OR(17), —COOR(17), phenyl, or an N-containing heterocycle having 1, 2, 3, 4, 5, 6, 7, 8, or 9 C atoms,
  where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, aminosulfonyl, and methylsulfonylamino, R(15) and R(16) are the same or different, and each is hydrogen, alkyl having 1, 2, 3, or 4 C atoms, or —$C_zH_{2z}$-phenyl,
 where phenyl is unsubstituted or substituted by 1 or 2 substituents selected from F, Cl, Br, $CF_3$, $NO_2$, CN, OH, methyl, ethyl, methoxy, dimethylamino, sulfamoyl, methylsulfonyl, aminosulfonyl, and methylsulfonylamino;

or

R(15) and R(16) together are a chain of 4 or 5 methylene groups, one $CH_2$ group of which is optionally replaced by —O—, —S—, —NH—, —N($CH_3$)— or —N(benzyl)—, R(17) is hydrogen or alkyl having 1, 2, or 3 C atoms, R(5), R(6), R(7) and R(8) are the same or different and each is hydrogen, F, Cl, Br, I, alkyl having 1, 2, 3, 4, or 5 C atoms, cycloalkyl having 3, 4, 5, 6, 7, or 8 C atoms, —CN, —$CF_3$, —$C_2F_5$, —$C_3F_7$, —$N_3$, —$NO_2$, —Y—$C_sH_{2s}$—R(18), or phenyl,
 where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, Y is —O—, —CO—, —CO—O—, —O—CO—, —S—, —SO—, —$SO_2$—, —$SO_2$—O—, —$SO_2$NR(10c), —NR(10c)—, or —CONR(10c)—, R(10c) is hydrogen or alkyl having 1, 2, or 3 C atoms, s is zero, 1, 2, 3, 4, 5, or 6;

R(18) is hydrogen, $CF_3$, $C_2F_5$, $C_3F_7$, cycloalkyl having 3, 4, 5, 6, 7, or 8 C atoms, —COOR(21), 1-piperidyl, 1-pyrrolidinyl, 4-morpholinyl, 4-methylpiperazin-1-yl, pyridyl, thienyl, imidazolyl, quinolyl, isoquinolyl, or phenyl,
 where pyridyl, thienyl, imidazolyl, quinolyl, isoquinolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(21) is hydrogen or alkyl having 1, 2, or 3 C atoms, R(9) is hydrogen, OR(10d), or OCOR(10d), R(10d) is hydrogen or alkyl having 1, 2, or 3 C atoms, B is hydrogen, or R(9) and B together form a bond, and 8) a compound of the formula VIII, an isomer thereof, or a physiologically acceptable salt thereof:

(VIII)

[Structure VIII: chroman ring analogous to VII with R(1)–R(9), B substituents]

where

R(1) and R(2) are the same or different and each is hydrogen, $CF_3$, $C_2F_5$, $C_3F_7$, alkyl having 1, 2, 3, 4, 5, or 6 C atoms, or phenyl, where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(1) and R(2) together form an alkylene chain having 2, 3, 4, 5, 6, 7, 8, 9, or 10 C atoms, R(3) is R(10)—$C_nH_{2n}$—NR(11)— or R(10)—$C_nH_{2n}$—, where one $CH_2$ group in the groups $C_nH_{2n}$ is optionally replaced by —O—, —CO—, —S—, —SO—, —$SO_2$—, or —NR(12a)—, R(12a) is hydrogen, methyl, or ethyl, R(10) is hydrogen, methyl, cycloalkyl having 3, 4, 5, 6, 7, or 8 C atoms, $CF_3$, $C_2F_5$, or $C_3F_7$, n is zero, 1, 2, 3, 4, 5, 6, 7, 8, 9, or 10, R(11) is hydrogen or alkyl having 1, 2, 3, 4, 5, or 6 C atoms, or R(10) and R(11) together form a bond if n is 3 or greater, or R(3) together with R(4) is an alkylene chain having 3, 4, 5, 6, 7 or 8 C atoms, where one $CH_2$ group of the alkylene chain is optionally replaced by —O—, —CO—, —S—, —SO—, —$SO_2$—, or —NR(12a)—, R(12a) is hydrogen, methyl or ethyl, R(4) is R(13)—$C_rH_{2r}$—, where one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(14)—, or —CONR(14)—, R(14) is hydrogen, alkyl having 1, 2, or 3 C atoms, —$C_yH_{2y}$—OR(12b), or —$C_yH_{2y}$—NR(12b)$_2$, R(12b) is hydrogen, methyl, or ethyl, y is 2 or 3, R(13) is H, $CF_3$, $C_2F_5$, $C_3F_7$, cycloalkyl having 3, 4, 5, 6, 7, or 8 C atoms, —NR(15)R(16), —CONR(15)R(16), —OR(17), —COOR(17), phenyl, or an N-containing heterocycle having 1, 2, 3, 4, 5, 6, 7, 8, or 9 C atoms, where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(15) and R(16) are the same or different and each is hydrogen or alkyl having 1, 2, 3, or 4 C atoms, or R(15) and R(16) together form a chain of 4 or 5 methylene groups, one $CH_2$ group of which is optionally replaced by —O—, —S—, —NH—, —N($CH_3$)—, or —N(benzyl)—, R(17) is hydrogen, alkyl having 1, 2, or 3 C atoms, —$C_xH_{2x}$OR(12c), R(12c) is hydrogen, methyl or ethyl, x is 2 or 3, r is zero, 1, 2, 3, 4, 5, 6, 7, 8, 9, 10, 11, 12, 13, 14, 15, 16, 17, 18, 19, or 20, at least one of the substituents R(5), R(6), R(7), and R(8) is —Y—$C_sH_{2s}$—R(18), thienyl, furyl or an N-containing heterocycle having 1, 2, 3, 4, 5, 6, 7, 8 or 9 C atoms, where thienyl, furyl, and the N-containing heterocycle are unsubstituted or substituted by 1 or 2 substituents selected from F, Cl, Br, I, $CF_3$, $NO_2$, CN, $NH_2$, OH, methyl, ethyl, methoxy, methylamino, dimethylamino, ethylamino, diethylamino, sulfamoyl, methylsulfonyl, and methylsulfonylamino, Y is —O—, —CO—, —O—CO—, —S—, —SO—, —$SO_2$—, —$SO_2$—O—, —$SO_2$NR(12d)—, —NR(12d)—, or —CONR(12d)—, where the attachment to the benzene ring is in each case effected through the atom depicted on the left of each of the above groups;

R(12d) is hydrogen, methyl, or ethyl;

s is 1, 2, 3, 4, 5 or 6;

R(18) is substituted phenyl having one or two substituents selected from $NO_2$, CN, $NH_2$, N(methyl)$_2$, OH, ethyl, —COOH, —COOmethyl, —COOethyl, —CONH$_2$, and —CON(methyl)$_2$, or R(18) is a substituted N-containing heterocycle having 1, 2, 3, 4, 5, 6, 7, 8, or 9 C atoms and carrying 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(18) is —OR(19), —$SO_2$R(19), —NR(19)R(20), —CONR(19)R(20), R(19) and R(20) are the same or different and each is $C_tH_{2t}$—R(21), t is zero, 1, 2, 3, 4, 5, or 6, R(21) is hydrogen, $CF_3$, $C_2F_5$, $C_3F_7$, cycloalkyl having 3, 4, 5, 6, 7, or 8 C atoms, NR(22)R(23), —OR(24), phenyl, thienyl, or an N-containing heterocycle having 1, 2, 3, 4, 5, 6, 7, 8, or 9 C atoms, where phenyl, thienyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;

R(22) and R(23) are the same or different and each is hydrogen, alkyl having 1, 2, or 3 C atoms, or R(22) and R(23) together form a chain of 4 or 5 methylene groups, one $CH_2$ group of which is optionally replaced by —O—, —S—, —NH—, —N($CH_3$)—, or —N(benzyl)—, R(24) is hydrogen, alkyl having 1, 2, or 3 C atoms, and the in each case the other substituents R(5), R(6), R(7) and R(8) which are not defined above are the same or different and each is hydrogen, F, Cl, Br, I, alkyl having 1, 2, 3, 4 or 5 C atoms, cycloalkyl having 3, 4, 5, 6, 7 or 8 C atoms, CN, $CF_3$, $NO_2$, OR(12e), or NR(12e)R(12f), R(12e) and R(12f) are the same or different and each is hydrogen or alkyl having 1, 2, 3, or 4 C atoms, R(9) is hydrogen, OR(12g), or OCOR(12g), R(12g) is hydrogen or alkyl having 1, 2, or 3 C atoms, B is hydrogen,
or
R(9) and B together form a bond; and 9) a compound of the formula IX, an isomer thereof, or a physiologically acceptable salt of any of the foregoing:

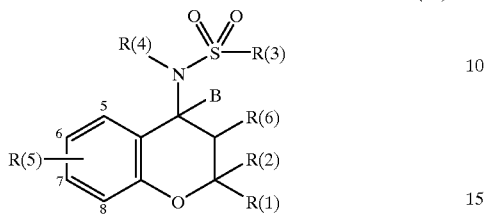

(IX)

where R(5) is attached to one of the positions labeled 5, 6, 7, and 8, and where R(1) and R(2) are the same or different and each is hydrogen, $CF_3$, $C_2F_5$, $C_3F_7$, alkyl having 1, 2, 3, 4, 5, or 6 C atoms, or phenyl,
  where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
or
R(1) and R(2) together form an alkylene chain having 2, 3, 4, 5, 6, 7, 8, 9, or 10 C atoms, R(3) is R(10)—$C_nH_{2n}$—NR(11)— or R(10)—$C_nH_{2n}$—,
  where one $CH_2$ group in the groups $C_nH_{2n}$ is optionally replaced by —O—, —CO—, —S—, —SO—, —$SO_2$—, or —NR(12a)—,
  R(12a) is hydrogen, methyl, or ethyl,
  R(10) is hydrogen, methyl, cycloalkyl having 3, 4, 5, 6, 7, or 8 C atoms, $CF_3$, $C_2F_5$, or $C_3F_7$,
  n is zero, 1, 2, 3, 4, 5, 6, 7, 8, 9, or 10,
  R(11) is hydrogen or alkyl having 1, 2, 3, 4, 5, or 6 C atoms,
  or
  R(10) and R(11) together form a bond if n is 3 or greater,
or
R(3) together with R(4) form an alkylene chain having 3, 4, 5, 6, 7, or 8 C atoms,
  where one $CH_2$ group of the alkylene chain is optionally replaced by —O—, —CO—, —S—, —SO—, —$SO_2$—, or —NR(12a)—,
  R(12a) is hydrogen, methyl, or ethyl,
R(4) is R(13)—$C_rH_{2r}$,
  where one $CH_2$ group of the group $C_rH_{2r}$ is optionally replaced by —O—, —CH=CH—, —C≡C—, —CO—, —CO—O—, —O—CO—, —S—, —SO—, —$SO_2$—, or —NR(14)—,
  R(14) is hydrogen or alkyl having 1, 2, or 3 C atoms,
  R(13) is $CH_3$, $CF_3$, $C_2F_5$, $C_3F_7$, cycloalkyl having 3, 4, 5, 6, 7, or 8 C atoms, NR(15)R(16), phenyl, or an N-containing heterocycle having 1, 2, 3, 4, 5, 6, 7, 8 or 9 C atoms,
    where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl and methylsulfonylamino, R(15) and R(16) together form a chain of 4 or 5 methylene groups, one $CH_2$ group of which is optionally replaced by —O—, —S—, —NH—, —N(methyl)— or —N(benzyl)—,
  r is zero, 1, 2, 3, 4, 5, 6, 7, 8, 9, 10, 11, 12, 13, 14, 15, 16, 17, 18, 19, or 20,
R(5) is —Y—$C_sH_{2s}$—R(18) or phenyl, where the phenyl is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
  Y is —O—, —S—, or —NR(10c)—, R(10c) is hydrogen or alkyl having 1, 2, or 3 C atoms,
  s is 1, 2, 3, 4, 5, 6, 7, or 8,
  R(18) is hydrogen, $CF_3$, $C_2F_5$, $C_3F_7$, cycloalkyl having 3, 4, 5, 6, 7 or 8 C atoms, —COOR(21), NR(15a)R(16a), an unsubstituted N-containing heterocycle having 1, 2, 3, 4, 5, 6, 7, 8, or 9 C atoms, phenyl, or thienyl,
    where phenyl and thienyl are unsubstituted or substituted by 1 or 2 substituents selected from F, Cl, Br, I, $CF_3$, methyl, methoxy, sulfamoyl, methylsulfonyl and methylsulfonylamino,
  R(15a) and R(16a) together form a chain of 4 or 5 methylene groups, one $CH_2$ group of which is optionally replaced by —O—, —S—, —NH—, —N(methyl)—, or —N(benzyl)—,
  R(21) is hydrogen or alkyl having 1, 2, or 3 C atoms,
R(6) is OR(10d) or OCOR(10d),
  where R(10d) is hydrogen or alkyl having 1, 2, or 3 C atoms,
B is hydrogen,
or
R(6) and B together form a bond; and 10) a compound of the formula X, an isomer thereof, or a physiologically acceptable salt of any of the foregoing:

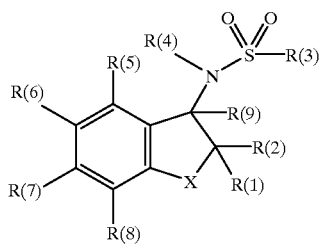

(X)

where
R(1) and R(2) are the same or different and each is hydrogen, $CF_3$, alkyl having 1, 2, 3, 4, 5, or 6 C atoms,
or
R(2) and R(9) together form a bond,
or R(2) is —OR(10a),
  where R(10a) is hydrogen, acetyl or alkyl having 1, 2, or 3 C atoms,
R(3) is R(10b)—$C_nH_{2n}$—NR(11)—, or R(10b)—$C_nH_{2n}$—, where one $CH_2$ group in the groups $C_nH_{2n}$ is optionally replaced by —O—, —CO—, —S—, —SO—, —$SO_2$—, or —NR(12a)—, where R(12a) is hydrogen, methyl, or ethyl,
R(10b) is methyl, cycloalkyl having 3, 4, 5, 6, 7, or 8 C atoms, $CF_3$, $C_2F_5$, or $C_3F_7$, n is zero, 1, 2, 3, 4, 5, 6, 7, 8, 9, or 10, R(11) is hydrogen or alkyl having 1, 2, 3, 4, 5, or 6 C atoms, or R(10b) and R(11) together form a bond if n is 2 or greater, or R(3) together with R(4) is an alkylene chain having 3, 4, 5, 6, 7, or 8 C atoms, where one $CH_2$ group of the alkylene chain is optionally replaced by —O—, —CO—, —S—, —SO—, —$SO_2$—, or —NR(12a)—, R(12a) is hydrogen, methyl or ethyl, R(4) is R(13)—$C_rH_{2r}$, where one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(14)— or —CONR(14)—, R(14) is hydrogen, alkyl having 1, 2, or 3 C atoms, —$C_yH_{2y}$—OR(12b), —$C_yH_{2y}$—NR(12b)$_2$, R(12b) is hydrogen, methyl, or ethyl, y is 2 or 3, R(13) is $CH_3$, $CF_3$, $C_2F_5$, $C_3F_7$, cycloalkyl having 3, 4, 5, 6, 7, or 8 C atoms, —NR(15)R(16), —CONR(15)R(16), —OR(17), —COOR(17), phenyl, or an N-containing heterocycle having 1, 2, 3, 4, 5, 6, 7, 8, or 9 C atoms, where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(15) and R(16) are the same or different and each is hydrogen or alkyl having 1, 2, 3, or 4 C atoms, or R(15) and R(16) together form a chain of 4 or 5 methylene groups, one $CH_2$ group of which is optionally replaced by —O—, —S—, —NH—, —N($CH_3$)— or —N(benzyl)—, R(17) is hydrogen, alkyl having 1, 2, or 3 C atoms, —$C_zH_{2z}$OR(12c), R(12c) is hydrogen, methyl, or ethyl, z is 2 or 3, r is zero, 1, 2, 3, 4, 5, 6, 7, 8, 9, 10, 11, 12, 13, 14, 15, 16, 17, 18, 19, or 20, R(5), R(6), R(7) and R(8) are the same or different and each is hydrogen, F, Cl, Br, I, alkyl having 1, 2, 3, 4, or 5 C atoms, cycloalkyl having 3, 4, 5, 6, 7 or 8 C atoms, —CN, —$CF_3$, —$C_2F_5$, —$C_3F_7$, —$N_3$, —$NO_2$, —Y—$C_sH_{2s}$—R(18), phenyl, thienyl, furyl, or an N-containing heterocycle having 1, 2, 3, 4, 5, 6, 7, 8, or 9 C atoms, where phenyl, thienyl, furyl, and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, Y is —O—, —CO—, —CO—O—, —O—CO—, —S—, —SO—, —$SO_2$—, —O—$SO_2$—, —$SO_2$NR(10c), or —CONR(10c)—, where the attachment to the benzene ring is, in each case, effected through the atom depicted on the left of each of the above groups, where R(10c) is hydrogen or alkyl having 1, 2, or 3 C atoms, s is zero, 1, 2, 3, 4, 5, or 6, R(18) is hydrogen, methyl, $CF_3$, $C_2F_5$, $C_3F_7$, cycloalkyl having 3, 4, 5, 6, 7, or 8 C atoms, —OR(21), —COOR(21), —NR(15a)R(16a), —CONR(15a)R(16a), phenyl, or an N-containing heterocycle having 1, 2, 3, 4, 5, 6, 7, 8, or 9 C atoms, where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(15a) and R(16a) are the same or different and each is hydrogen or alkyl having 1, 2, 3, or 4 C atoms, or R(15a) and R(16a) together form a chain of 4 or 5 methylene groups, one $CH_2$ group of which is optionally replaced by —O—, —S—, —NH—, —N($CH_3$)—, or —N(benzyl)—, R(21) is hydrogen or alkyl having 1, 2, or 3 C atoms, R(9) is hydrogen or, together with R(2), forms a bond, X is —CR(22)R(23)—, —O—, —NR(24)—, —S—, —SO—, —$SO_2$—, R(22) and R(23) are the same or different and each is hydrogen, $CF_3$, alkyl having 1, 2, 3, 4, 5, or 6 C atoms, R(24) is hydrogen, alkyl having 1, 2, 3, 4, 5, or 6 C atoms, or phenyl, where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl and methylsulfonylamino.

Unless defined otherwise, alkyl and alkenyl are straight-chain or branched ($C_1$–$C_4$)-alkyl and -alkenyl; respectively; alkoxy is ($C_1$–$C_4$)-alkoxy; cycloalkyl is ($C_3$–$C_8$)-cycloalkyl; aryl is ($C_6$–$C_{12}$)-aryl; heteroaryl is furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl; acyl is ($C_1$–$C_4$)—CO or ($C_6$–$C_{12}$)-aryl-CO or heteroaryl-CO; halo or halogen is F, Cl, Br; heterocyclo is as defined under heteroaryl, but also partially or fully hydrogenated.

The present invention describes the use of a novel class of active compounds, i.e. the $I_{KS}$ channel blockers, as chemotherapeutics for use against human and animal pathogenic endo- and ectoparasites. The action of these blockers is based on a novel anthelminthic and ectoparasiticidal principle; $I_{KS}$ channel blockers block the slowly activated potassium channel, resulting in a loss of function of the pharyngal muscle which is essential for food intake; this mechanism of action in the end leads to death of the parasites by starvation.

$I_{KS}$ channel blockers are effective against animal and human pathogenic trematodes (Fasciola hepatica, Fasciolopsis buski, Fasciola gigantica, Fascioloides magna, Dicrocoelium dendriticum, Opisthorchis felineus, Clonorchis sinensis, Paragonimus westermanni, Paragonimus kellikotti, Schistosoma haematobium, Schistosoma japonicum, Schistosoma mansoni) and animal and human pathogenic nematodes belonging to the families of the Trichuridae, Trichinellidae, Strongyloididae, Ancylostomatidae, Strongylidae, Trichostrongylidae, Metastrongylidae, Oesophagostomatidae, Dictyocaulidae, Protostrongylidae, Angiostrongylidae, Oxyuridae, Ascaridae, Toxocaridae, Dracunculidae, Habronematidae and Filariidae; additionally, the activity spectrum of the $I_{KS}$ channel blockers also includes animal and human pathogenic ectoparasites belonging to the class of the Arachnida (family: Argasidae, Ixodidae, Dermanyssidae, Demodicidae, Sarcoptidae, Psoroptidae, Varroidae) and the class of the Insecta comprising the orders of the Phthiraptera (Anoplura, Mallophaga), Diptera and Siphonaptera.

While being tolerated well by plants and having favorable toxicity toward warm-blooded animals, the active compounds are suitable for controlling phytopathogenic animal pests, especially insects, arachnids, nematodes and molluscs, and very particularly preferably for controlling insects and arachnids, which are encountered in agriculture, in animal breeding, in forestry, in the protection of stored products and materials, and in the hygiene sector. They are active against normally sensitive and resistant species and against all or certain stages of development. The abovementioned pests include:

From the order of the Acarina, for example, *Acarus siro*, Argas spp., *Eriophyes ribis, Phyllocoptruta oleivora*, Tarsonemus spp., *Bryobia praetiosa*, Panonychus spp., Tetranychus spp., Eotetranychus spp., Oligonychus spp. and Eutetranychus spp.

From the order of the Isopoda, for example, *Oniscus asselus, Armadium vulgar* and *Porcellio scaber*.

From the order of the Diplopoda, for example, *Blaniulus guttulatus*.

From the order of the Chilopoda, for example, *Geophilus carpophagus* and Scutigera spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea madeirae, Blattella germanica, Acheta domesticus*, Gryllotalpa spp., *Locusta migratoria migratorioides, Melanoplus differentialis* and *Schistocerca gregaria*.

From the order of the Isoptera, for example, Reticulitermes spp.

From the order of the Anoplura, for example, *Phylloera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis, Thrips tabaci* and Frankliniella spp.

From the order of the Heteroptera, for example, Euryaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum*, Aphis spp., *Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma, Anthrenus spp., Attagenus spp., Lyctus spp., *Meligethes aeneus*, Ptinus spp., *Niptus hololeucus, Gibbium psylloides*, Tribolium spp., Tenebrio molitor, Agriotes spp., Conoderus spp., *Melolontha melolontha, Amphimallon solstitialis, Costelytra zealandica* and Lissorhoptus spp.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Cuterebra spp., Hypobosca spp., Stomoxys spp., Oestrus spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopsis* and Ceratophyllus spp.

From the order of the Arachnida, for example, *Scorpio maurus* and *Latrodectus mactans*.

From the class of the Gastropoda, for example, Deroceras spp., Arion spp., Lymnaea spp., Galba spp., Succinea spp., Biomphalaria spp., Bulinus spp. and Oncomelania spp.

From the class of the Bivalva, for example, Dreissena spp.

The phytoparasitic nematodes which can be controlled in accordance with the invention include, for example, the root-parasitic soil nematodes such as those of the genera Meloidogyne (root knot eelworms, such as *Meloidogyne incognita, Meloidogyne hapla* and *Meloidogyne javanica*), Heterodera and Globodera (cyst-forming nematodes, such as *Globodera rostochiensis, Globodera pallida, Heterodera trifolii*) and of the genera Radopholus (such as *Radopholus similis*), Pratylenchus (such as *Pratylenchus neglectus, Pratylenchus penetrans* and *Pratylenchus curvitatus*), Tylenchulus (such as *Tylenchulus semipenetrans*), Tylenchorhynchus (such as *Tylenchorhynchus dubius* and *Tylenchorhynchus claytoni*), Rotylenchus (such as *Rotylenchus robustus*), Helicotylenchus (such as *Helicotylenchus multicinctus*), Belonoaimus (such as *Belonoaimus longicaudatus*), Longidorus (such as *Longidorus elongatus*), Trichodorus (such as *Trichodorus primitivus*), and Xiphinema (such as *Xiphinema index*).

The compounds according to the invention can also be used to control the nematode genera Ditylenchus (stem parasites, such as *Ditylenchus dipsaci* and *Ditylenchus destructor*), Aphelenchoides (leaf nematodes, such as *Aphelenchoides ritzemabosi*) and Anguina (leaf-gall nematodes, such as *Anguina tritici*).

The invention also relates to compositions, especially insecticidal and acaricidal compositions, which comprise the compounds of the formula (I) in addition to suitable formulation auxiliaries.

The compositions according to the invention comprise the active compounds of the formula (I) in general in a proportion of from 1 to 95% by weight.

They can be formulated in various ways depending on the biological and/or chemicophysical parameters which prevail. Possible formulations which are preferable are therefore:

wettable powders (WP), emulsifiable concentrates (EC), aqueous solutions (SL), emulsions, sprayable solutions, oil- or water-based dispersions (SC), suspoemulsions (SE), dusting agents (DP), seed-dressing products, granules in the form of microgranules, spray granules, coated granules and adsorption granules, water-dispersible granules (WG), ULV formulations, microcapsules, waxes or baits.

These individual types of formulation are known in principle and are described, for example, in:

Winnacker-Küchler, "Chemische Technologie" [Chemical Technology], Volume 7, C. Hauser Verlag Munich, 4th ed. 1986; van Falkenberg, "Pesticides Formulations", Marcel Dekker N.Y., 2nd ed. 1972–73; K. Martens, "Spray Drying Handbook", 3rd ed. 1979, G. Goodwin Ltd. London.

The formulation auxiliaries required, such as inert materials, surfactants, solvents and other additives, are likewise known and are described, for example, in:

Watkins, "Handbook of Insecticide Dust Diluents and Carriers", 2nd ed., Darland Books, Caldwell N.J.; H. v. Olphen, "Introduction to Clay Colloid Chemistry", 2nd ed., J. Wiley & Sons, N.Y.; Marsden, "Solvents Guide", 2nd ed., Interscience, N.Y. 1950; McCutcheon's, "Detergents and Emulsifiers Annual", MC Pubi. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1967; Winnacker-Küchler, "Chemische Technologie", Volume 7, C. Hauser Verlag Munich, 4th ed. 1986.

Based on these formulations, it is also possible to produce combinations with other pesticidally active compounds, fertilizers and/or growth regulators, for example in the form of a readymix or a tank mix. Wettable powders are preparations, uniformly dispersible in water, which contain, beside the active compound and in addition to a diluent or inert material, wetting agents, for example polyethoxylated alkylphenols, polyethoxylated fatty alcohols, alkyl- or alkylphenolsulfonates, and dispersing agents, for example sodium ligninsulfonate or sodium 2,2'-dinaphthylmethane-6,6'-disulfonate.

Emulsifiable concentrates are prepared by dissolving the active compound in an organic solvent, for example butanol, cyclohexanone, dimethylformamide, xylene or higher-boiling aromatics or hydrocarbons, with addition of one or more emulsifiers. As emulsifiers, the following can be used, for example: calcium salts of alkylarylsulfonates, such as Ca dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talc, natural clays such as kaolin, bentonite, pyrophillite or diatomaceous earth. Granules can be prepared either by atomizing the active compound onto adsorptive, granulated inert material or by applying active compound concentrates onto the surface of carriers such as sand or kaolinites, or of granulated inert material, by means of adhesives, for example polyvinyl alcohol or sodium polyacrylate, or alternatively mineral oils. Suitable active compounds can also be granulated in the fashion conventional for the preparation of fertilizer granules, if desired as a mixture with fertilizers.

In wettable powders, the concentration of active compound is generally from approximately 10 to 90% by weight, the remainder to 100% by weight being composed of customary formulation components. In the case of emulsifiable concentrates, the concentration of active compound may generally be from approximately 5 to 80% by weight. Formulations in dust form generally comprise from 5 to 20% by weight of active compound, sprayable solutions from about 2 to 20% by weight. In the case of granules, the content of active compound depends partly on whether the active compound is in liquid or solid form and on which granulation auxiliaries, fillers, etc. are being used.

In addition, the abovementioned formulations of active compound comprise, if appropriate, the adhesives, wetting agents, dispersants, emulsifiers, penetrants, solvents, fillers or carriers which are customary in each case.

The concentrates, which are in the commercially customary form, are if appropriate diluted in the customary manner for their use, for example using water in the case of wettable powders, emulsifiable concentrates, dispersions and some microgranules. Dust and granule preparations, and also sprayable solutions, are normally not diluted any further with other inert substances before being used.

The application rate required varies with the external conditions, such as temperature and humidity among others. It can fluctuate within wide limits, for example between 0.0005 and 10.0 kg/ha or more of active compound, but is preferably between 0.001 and 5 kg/ha.

The active compounds according to the invention may be present in their commercially customary formulations, and in the application forms prepared from these formulations, as mixtures with other active compounds, such a s insecticides, attractants, sterilants, acaricides, nematicides, fungicides, growth regulators or herbicides.

The pesticides include, for example, phosphoric esters, carbamates, carboxylates, formamidines, tin compounds, compounds pre pared by microorganisms, inter alia.

Preferred co-components for mixtures are 1. from the group of the phosphorus compounds acephate, azamethiphos, azinphosethyl, azinphosmethyl, bromophos, bromophos-ethyl, cadusafos (F-67825), chlorethoxyphos, chlorfenvinphos, chlormephos, chlorpyrifos, chlorpyrifos-methyl, demeton, demeton-S-methyl, demeton-S-methylsulphone, dialifos, diazinon, dichlorvos, dicrotophos, dimethoate, disulfoton, EPN, ethion, ethoprophos, etrimfos, famphur, fenamiphos, fenitriothion, fensulfothion, fenthion, fonofos, formothion, fosthiazate (ASC-66824), heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, primiphos-ethyl, pirimiphos-methyl, profenofos, propaphos, proetamphos, prothiofos, pyraclofos, pyridapenthion, quinalphos, sulprofos, temephos, terbufos, tebupirimfos, tetrachlorvinphos, thiometon, triazophos, trichlorphon, vamidothion;

2. from the group of the carbamates alanylcarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenylbutyryl (methyl)carbamate, oxamyl, pirimicarb, propoxur, thiodicarb, thiofanox, 1-methylthio(ethylideneamino) N-methyl-N-(morpholinothio)carbamate (UC 51717), triazamate;

3. from the group of the carboxylates acrinathrin, allethrin, alphametrin, beta-cypermethrin, 5-benzyl-3-furyl-methyl (E)-(1R)-cis-2,2-dimethyl-3-(2-oxothiolan-3-ylidenemethyl)-cyclopropanecarboxylate, beta-cyfluthrin, beta-cypermethrin, bioallethrin, bioallethrin((S)-cyclopentyl isomer), bioresmethrin, biphenate, (RS)-1-cyano-1-(6-phenoxy-2-pyridyl)methyl (1RS)-trans-3-(4-tert-butyl-phenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D-isomer), imiprothrin (S-41311), lambda-cyhalothrin, permethrin, pheothrin ((R)-isomer), prallethrin, pyrethrine (natural products), resmethrin, tefluthrin, tetramethrin, theta-cypermethrin (TD-2344), tralomethrin, transfluthrin, zeta-cypermethrin (F-56701);

4. from the group of the amidines amitraz, chlordimeform;

5. from the group of the tin compounds cyhexatin, fenbutatin oxide;

6. others abamectin, ABG-9008, acetamipirid, Anagrapha falcitera, AKD-1022, AKD-3059, ANS-118, *Bacillus thuringiensis, Beauveria bassianea*, bensultap, bifenazate (D-2341), binapacryl, BJL-932, bromopropylate, BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chromafenozide, (ANS-118), CG-216, CG-217, CG-234, A-184699, (2-naphthylmethyl) cyclopropan-ecarboxylate (Ro12-0470), cyromazin, diacloden (thiamethoxam), diafenthiuron, ethyl N-(3,5-dichloro-4-(1,1,2,3,3,3-hexafluoro-1-propyloxy)phenyl) carbamoyl)-2-chloro-benzo-carboximidate, DDT, dicofol, difluobenzuron, N-(2,3-dihydro-3-methyl-1,3-thiazol-2-ylidene)-2,4-ylidene)-2,4-xylidene, dinobuton, dinocap, diofenolan, DPX-062, emamcetin-benzoate (MK-244), endosulfan, ethiprole, (sulfethiprole), ethofenprox, etoxazole (YI-5301), fenazaquin, fenoxycarb, fipronil, flumite, (flufenzine, SZI-121), 2-fluoro-5-(4-(4-ethoxyphenyl)-4-methyl-1-pentyl)diphenyl ether (MTI 800), granulosis and nuclear polyhedrosis viruses, fenpyroximate, fenthiocarb, flubenzimine, flucycloxuron, flufenoxuron, flufenprox (ICI-A-5683), fluproxyfen, gamma-HCH, halofenozide (RH-0345), halofenprox (MTI-732), hexaflumuron (DE-473), hexythiazox, HOI-9004, hydramethyinon (AC 217300), lufenuron, imidacloprid, indoxacarb (DPX-MP062), kanemite (AKD-2023), M-020, MIT-446, ivermectin, M-020, methoxyfenozide (Intrepid, RH-2485), milbemectin, NC-196, neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), pyriproxyfen (S-71639), NC-196, NC-111, NNI-9768, novaluron (MCW-275), OK-9701, OK-9601, OK-9602, propargite, pymethrozine, pyridaben, pyrimidifen (SU-8801), RH-0345, RH-2485, RYI-210, S-1283, S-1833, SB7242, SI-8601, silafluofen, silamadine (CG-177), spinosad, SU-9118, tebufenozide, tebufenpyrad (MK-239), teflubenzuron, tefuranitozine (MIT-446), tetradifon, tetrasul, thiacloprid, thiocyclam, TI-435, tolfenpyrad (OMI-88), triazamate (RH-7988), trifumuron, verbutin, vertalec (Mykotal), YI-5301.

The content of the active compound in the use forms prepared from the commercial formulations may be from 0.00000001 to 95% by weight of active compound, preferably between 0.00001 and 1% by w eight.

Application is effected in a conventional fashion, matched to the use forms.

The active compounds according to the invention of the formula (I) ar e also suitable for controlling endo- and ectoparasites in the veterinary sector or in the sector of animal husbandry.

The active compounds according to the invention are in this case applied in a known fashion, such as by oral application in the form of, for example, tablets, capsules, potions or granules, by dermal application in the form of, for example, dipping, spraying, pouring-on and spotting-on and powdering, and also by parenteral application in the form of, for example, injection.

The compounds, used according to the invention can accordingly also be employed particularly advantageously in livestock husbandry (for example cattle, sheep, pigs and poultry such as chickens, geese etc.). In a preferred embodiment of the invention, the novel compounds, if appropriate in suitable formulations (cf. above) and if appropriate with the drinking water or feed, are administered orally to the animals. Since excretion of these compounds occurs in an effective fashion in the droppings, the development of insects in the animal droppings can be prevented very simply in this way. The dosages and formulations suitable in each case are particularly dependent on the type and stage of development of the productive animals and also on the degree of infestation, and can easily be determined and fixed by conventional methods. In the case of cattle, the novel compounds can be employed, for example, in dosages of 0.01 to 100 mg/kg of body weight.

The compounds used according to the invention are also distinguished by an outstanding fungicidal action. Fungal pathogens which have already penetrated the plant tissue can be successfully subjected to curative control. This is particularly important and advantageous in the case of those fungal diseases which can no longer be controlled effectively with the otherwise customary fungicides when infection has taken place already. The spectrum of action of the claimed compounds embraces various economically important phytopathogenic fungi, for example *Plasmopara viticola, Phytophthora infestans, Erysiphe graminis, Piricularia oryzae, Pyrenophora teres, Leptosphaerea nodorum, Pellikularia sasakii* and *Puccinia recondita*.

In addition, the compounds according to the invention are also suitable for use in technical fields, for example as wood preservatives, as preservatives in paints, in cooling lubricants for metalworking, or as preservatives in drilling and cutting oils.

The active compounds according to the invention in their commercially customary formulations can be employed either alone or in combination with other fungicides known from the literature.

Fungicides known from the literature which can be combined according to the invention with the compounds of the formula I include, for example, the following products:

aldimorph, andoprim, anilazine, azoxystrobin, azaconazole, BAS 450F, benalaxyl, benodanil, benomyl, bethoxazin, binapacryl, bion (CGA-245704), bitertanol, bromuconazole, buthiobate, captafol, captan, carbendazim, carboxin, carpropamide, CGA 173506, cymoxanil, cyproconazole, cyprodinil, cyprofuram, diflumetorim, dichlofluanid, dichlomezine, diclobutrazol, diclocymet (S-2900), diclomezine, diethofencarb, difenconazol (CGA 169374), difluconazole, dimethirimol, dimethomorph, diniconazole, dinocap, dithianon, dodemorph, dodine, edifenfos, epoxiconazole, ethirimol, etridiazole, famoxadone, (DPX-JE874), fenarimol, fenbuconazole, fenfuram, fenhexamide, fenpiclonil, fenpropidin, fenpromorph, fentin acetate, fenti hydroxide, ferimzone (TF 164), fluazinam, fluobenzimine, fludioxonil, flumetover (RPA-403397), fluquinconazole, fluorimide, flusilazole, flusulfamide, flutolanil, flutriafol, folpet, fosetylaluminum, fuberidazole, furalaxyl, furconazole, furametpyr (S-82658), furmecyclox, guazatine, hexaconazole, imazalil, imibenconazole, ipconazole, iprobenfos, iprodione, isoprothiolane, KNF 317, cresoxime-methyl (BAS-490F), copper compounds such as Cu oxychloride, oxine-Cu, Cu oxide, mancozeb, maneb, mepapanipyrim (KIFD 3535), mepronil, metalaxyl, metalaxyl-M (CGA-329351), metconazole, methasulfocarb, methfuroxam, metominofen (SSF-126), metominostrobin (fenominostrobin, SSF-126), MON-24000, MON-6550, MON-41100, myclobutanil, nabam, nitrothalidopropyl, nuarimol, ofurace, OK-9601, OK-9603, oxadixyl, oxycarboxin, penconazole, pencycuron, PP 969, polyoxins, probenazole, propineb, prochloraz, procymidon, propamocarb, propiconazole, prothiocarb, pyracarbolid, pyrazophos, pyrifenox, pyrimethanil, pyroquilon, quinoxyfen (DE-795), rabenzazole, RH-7592, RH-7281, sulfur, spiroxamine, SSF-109, tebuconazole, tetraconazole, TTF 167, thiabendazole, thicyofen, thifluzamide (RH-130753), thiofanatemethyl, thiram, TM-402, tolclofos-methyl, tolylfluanid, triadimefon, triadimenol, triazoxide, trichoderma harzianum (DHF-471), tricyclazole, tridemorph, triflumizol, triforine, triflumizole (UCC-A815), triticonazole, validamycin, vinchlozolin, XRD 563, zineb, sodium dodecylsulfonate, sodium dodecyl sulfate, sodium C13/C15 alcohol ether sulfonate, sodium cetostearyl phosphate ester, sodium dioctylsulfosuccinate, sodium isopropylnapthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium choride and 1-hydroxyethyl-2-alkyl-imidazoline.

The abovementioned components for combinations are known active compounds of which many are described in The Pesticide Manual (Editor: Clive Tomlin), 11th edition (1997), Crop Protection Publications/ISBN 1-901396-11-8 795.

The content of active compound in the use forms prepared from the commercial formulations can vary within wide limits, and the concentration of active compound in the use forms can be from 0.0001 up to 95% by weight of active compound, preferably between 1 and 50% by weight. Application is effected in a conventional fashion, matched to the use forms.

A. FORMULATION EXAMPLES a) A dusting agent is obtained by mixing 10 parts by weight of active compound and 90 parts by weight of talc as inert material and comminuting in a hammer mill.

b) A wettable powder which is easily dispersible in water is obtained by mixing 25 parts by weight of active compound, 65 parts by weight of kaolincontaining quartz as inert material, 10 parts by weight of potassium ligninsulfonate and 1 part by weight of sodium oleoylmethyltaurate as wetting and dispersing agent, and grinding in a pinned disk mill.

c) A dispersion concentrate which is easily dispersible in water is prepared by mixing 40 parts by weight of active compound with 7 parts by weight of a sulfosuccinic monoester, 2 parts by weight of a sodium ligninsulfonate and 51 parts by weight of water and grinding in a ball mill to a fineness of below 5 microns.

d) An emulsifiable concentrate can be prepared from 15 parts by weight of active compound, 75 parts by weight of cyclohexane as solvent and 10 parts by weight of ethoxylated nonylphenol (10 EO) as emulsifier.

e) Granules can be prepared from 2 to 15 parts by weight of active compound and an inert granule carrier material such as attapulgite, granulated pumice and/or quartz sand. It is expedient to use a suspension of the wettable powder of Example b) with a solids content of 30% which is sprayed onto the surface of attapulgite granules which are then dried and intimately mixed. The proportion by weight of the wettable powder in this case is about 5% and that of the inert carrier material is about 95% of the finished granules.

To test the ct of $I_{KS}$ channel blockers on the KQT1 channel, electrophysiological studies were carried out on Xenopus oocytes which express the KQT1 channel (specific $I_{KS}$ channel of the nematode Caenorhabditis elegans). An adult female frog (Xenopus laevis) was sacrified lege artis, and oocytes of all development stages were removed from the ovarian bags. Oocytes of the development stages V and VI were selected; using a nanoliter injector mounted in a micromanipulator, 10 ng of the KQT1-specific m-RNA were injected into each oocyte. After 1–4 days, sufficient KQT1 channels were expressed for it to be possible to measure the corresponding currents. For measuring the slowly activated potassium currents under constant intracellular conditions, the two-microelectrode voltage clamp method was employed. This method is based on operating with 2 intracellular microelectrodes; the first electrode measures the membrane potential against a reference electrode, the second electrode is used to inject current which is necessary to maintain a desired potential. During the measurement, the holding potential was adjusted to −80 mV, which corresponds to the open-circuit membrane potential.

The electrophysiological measuring stand comprised a vibration-damped experiment table on which were mounted a purpose-made measuring chamber, 2 micromanipulators, in each case with a preamplifier and a holder for injection microelectrodes, and a stereomicroscope.

The complete measuring stand was surrounded by a Faraday cage to minimize electrical disturbances during the measurement. During the measurement, the oocyte was suspended in a solution of ND96 buffer. To activate the voltage-dependent $I_{KS}$ channel, the oocyte membrane was depolarized by a voltage jump from the holding potential (−80 mV) to 0 mV, and this state was maintained for 10 seconds before the holding potential was reestablished. The time profile of the measuring protocol was repeated every 45 s. During the depolarization phase, the slowly activated potassium current was measured. The channel-blocking effect of various $I_{KS}$ channel blockers was tested at concentrations of 100, 10, 1 and 0.1 µM; the measured current amplitude without the influence of the preparation compared with the current amplitude under the influence of the preparation was used as an indication of the activity of an $I_{KS}$ channel blocker and was expressed in percent inhibition or $IC_{50}$. Depending on the structure of the $I_{KS}$ channel blockers, inhibition values of 90% or IC50 values of <2 μM were determined at concentrations of 10 μM.

Using gene function analysis, which resulted in inactivation of the KQT1 gene by targeted mutation, it was possible to elucidate the physiological role of the $I_{KS}$ channel in the pharyngeal pump mechanism. After preparation of KQT1-negative mutants of C. elegans it was observed that these mutants were not viable and starved.

To test the effect of the $I_{KS}$ channel blockers on helminths, an in vitro test (larvae development test) was carried out using larvae of the chicken ascarid Ascaridia galli. Embryonated eggs of A. galli were surface-sterilized by treatment with 5% strength sodium hypochlorite solution and, after removal of this solution, opened mechanically by rotating glass beads (5 mm). The hatched L2-larvae were enriched via larvae enrichment processes, taken up in a special nutrient medium (KW-2 medium) and incubated at 41° C. and 10% $CO_2$.

48 hours after hatching, the larvae were incubated in microtiter plates (96 well) for 5 days, using medicated medium (200 μl) in the concentrations (200, 100, 50 . . . 0.1 μg/ml) (41° C., 10% $CO_2$). During the 5-day incubation time, motility, morphology and vitality were checked daily using a microscope and documented. After medication, the larvae culture was incubated for 48 hours using Neutral Red in a concentration of 0.16%; after removal of the Neutral Red by changing the medium, the enrichment of the vital dye in the intestine of the larvae was evaluated as an indication of active food intake and thus proof of vitality. The medication of the larvae with $I_{KS}$ channel blockers in the concentrations 200, 100, 50 and 25 μg/ml resulted in a mortality of 100%.

The effect of $I_{KS}$ channel blockers against ectoparasites was examined in the flea larvae test (cat flea= Ctenocephalides felis). 5 mg of substance were dissolved in 0.5 ml of acetone and mixed with 500 mg of blood meal. After the solvent had evaporated, in each case 2 g of quartz sand were mixed with medicated blood meal such that preparation concentrations of 1000, 500, 250, 100 ppm resulted. Per medicated sample or solvent control, 15 flea eggs were placed into the mixture of medicated blood meal and quartz sand, and the eggs were subsequently incubated at 37° C. and high atmospheric humidity. The larval development, pupation and development to the adult stage was checked at intervals of 3–5 days, and the mortality rates were documented. As a function of the dose, a larvicidal effect of 100%, compared with the solvent control, was observed.

In principle, in the treatment of helminths and ectoparasites, therapeutic, meta- and prophylactic measures have to be distinguished; these different treatment methods require specific pharmaceutical formulations. Such formulations ensure, for example, the continuous release of sub-therapeutic to therapeutic doses of anthelmintics or of ectoparasiticides which are classified as "sustained" and "pulse-release boluses", depending on their release mode. The former are further differentiated into "slow-release boluses", i.e. those having a decreasing release rate, and "continous-release boluses", i.e. those having a steady release mode. In contrast, "pulse-release boluses" release the entire active compound in the course of a few hours to days. In addition to the release technology, which also embraces microencapsulation of active compounds and which is becoming increasingly popular in veterinary medicine, so-called "spot on" or "pour on" formulations are customary for external use on animals; administration of tablets, pastes or injections for solution and the use of collars comprising the medicaments, for example counteracting ectoparasites, are state of the art.

Activity against KQT1 in *Xenopus oocytes*

| Structure | Name | Inhibition at 10M |
|---|---|---|
| 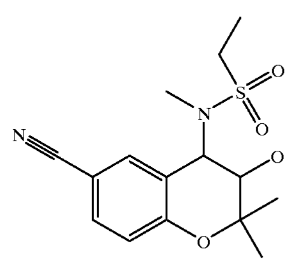 | 6-CYANO-4-TRANS-(N-ETHYLSULFONYL-N-METHYLAMINO)-3 HYDROXY-2,2-DIMETHYLCHROMANE | 40% |
| 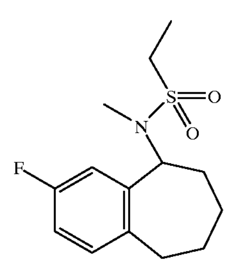 | N-ETHYLSULFONYL-N-METHYLAMINO-8-FLUOROBENZOCYCLO-HEPTANE | 78% |

-continued

| Structure | Name | Inhibition at 10M |
|---|---|---|
| 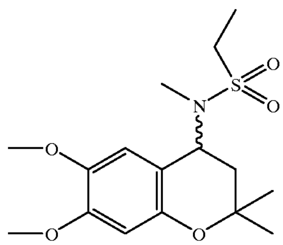 | 4-N-ETHYLSULFONYL-N-METHYLAMINO-6,7 DIMETHOXY-2,2-DIMETHYLCHROMANE | 30% |
| 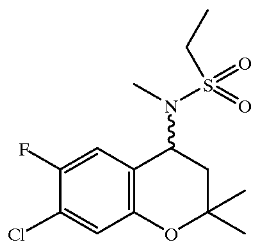 | 7-CHLORO-4-N-ETHYLSULFONYL-N-METHYLAMINO-6-FLUORO-2,2-DIMETHYLCHROMANE | 89% |
| 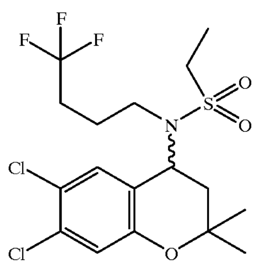 | 6,7-DICHLORO-4-[N-ETHYLSULFONYL-N-(4,4,4-TRIFLUORO-BUTYL)AMINO]-2,2-DIMETHYLCHROMANE | 88% |
| 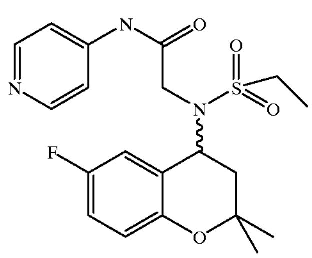 | 2-[ETHANESULFONYL-(6-FLUORO-2,2-DIMETHYL-CHROMAN-4-YL)-AMINO]-N-PYRIDIN-4-YL-ACETAMIDE | 35% |
| 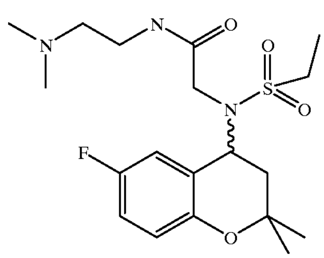 | N-(2-DIMETHYLAMINO-ETHYL)-2-[ETHANE-SULFONYL-(6-FLUORO-2,2-DIMETHYL-CHROMAN-4-YL)-AMINO]-ACETAMIDE | 22% |

| Structure | Name | Inhibition at 10M |
|---|---|---|
| 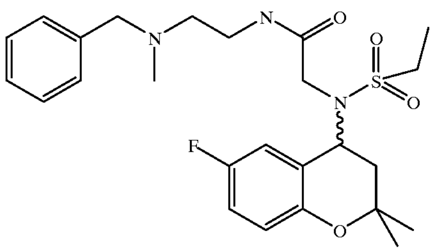 | N-[2-(BENZYL-METHYL-AMINO)-ETHYL]-2-[ETHANESULFONYL-(6-FLUORO-2,2-DIMETHYL-CHROMAN-4-YL)-AMINO]-ACETAMIDE | 36% |
| Chiral | (3R,4S)-(+)-N-[-3-HYDROXY-2,2-DIMETHYL-6-(4,4,4-TRIFLUORO-BUTOXY)-CHROMAN-4-YL]-N-METHYL-METHANE-SULFONAMIDE | 46% |
| Chiral | (3S,4R)-(−)-N-[-3-HYDROXY-2,2-DIMETHYL-6-(4,4,4-TRIFLUORO-BUTOXY)-CHROMAN-4-YL]-N-METHYL-METHANE-SULFONAMIDE | 97% |
| 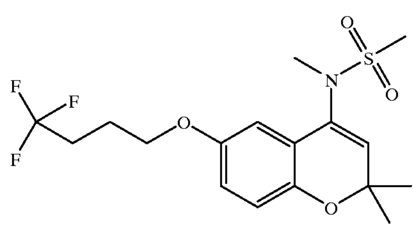 | N-[2,2-DIMETHYL-6-(4,4,4-TRIFLUOROBUTOXY)-2H-CHROMEN-4-YL]-N-METHYL-METHANESULFONAMIDE | 92% |

We claim:

1. A method for treating a disease involving a helminth or ectoparasite, said method comprising administering to a patient in need thereof an effective amount of a KQT1 channel blocker.

2. A method according to claim 1, wherein the KQT1 channel blocker further possesses $I_{KS}$ channel inhibitor activity.

3. A method according to claim 2, wherein the KQT1 channel blocker possesses simultaneous activity as an $I_{KS}$ channel inhibitor.

4. A method according to claim 1, wherein the KQT1 channel blocker comprises at least one compound selected from 1) a chromane of the formula I, or an isomer thereof, or a physiologically acceptable salt of any of the foregoing:

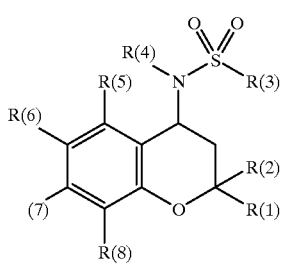

(I)

where

R(1) and R(2) are the same or different, and each is hydrogen, $C_pF_{2p+1}$, alkyl having 1, 2, 3, 4, 5, or 6 C atoms, or phenyl, where any of the foregoing is unsubstituted or substituted by 1 or 2 substituents selected from F, Cl, Br, I, $CF_3$, methyl, methoxy, sulfamoyl, methylsulfonylamino, and methylsulfonyl, and p is 1, 2, or 3, or R(1) and R(2) together form an alkylene chain having 2, 3, 4, 5, 6, 7, 8, 9 or 10 C atoms, R(3) is R(9)—$C_nH_{2n}$[NR(11)]$_m$—, where R(9) is hydrogen or cycloalkyl having 3, 4, 5, 6, 7, or 8 C atoms, n is zero, 1, 2, 3, 4, 5, 6, 7, 8, 9, or 10, m is zero or 1, R(11) is hydrogen or alkyl having 1, 2, 3, 4, 5, or 6 C atoms, or R(11) together with R(9) form an alkylene group having 1, 2, 3, 4, 5, 6, 7, or 8 C atoms, where a $CH_2$ group of the group $C_nH_{2n}$ is optionally replaced by —O—, —$SO_q$— or —NR(10)—, q is zero, 1 or 2, R(10) is hydrogen, methyl, or ethyl, R(4) is R(12)—$C_rH_{2r}$, where R(12) is hydrogen, cycloalkyl having 3, 4, 5, 6, 7, or 8 C atoms, piperidyl, 1-pyrrolidinyl, N-morpholino, N-methylpiperazino, $C_pF_{2p+1}$, pyridyl, thienyl, imidazolyl or phenyl, any of the foregoing being unsubstituted or substituted by 1 or 2 substituents selected from F, Cl, Br, I, $CF_3$, methyl, methoxy, sulfamoyl, methylsulfonyl, or methylsulfonylamino;

r is 1, 2, 3, 4, 5, 6, 7, 8, 9, 10, 11, 12, 13, 14, 15, 16, 17, 18, 19, or 20, where a $CH_2$ group of the group $C_rH_{2r}$ is optionally replaced by —O—, —HC=CH—, —C≡C—, —CO—, —CO—O—, —$SO_q$— or —NR(10)—, q is zero, 1, or 2, R(10) is hydrogen, methyl or ethyl, R(5), R(6), R(7) and R(8) are the same or different and each is hydrogen, F, Cl, Br, I, alkyl having 1, 2, 3, or 4 C atoms, cycloalkyl having 3, 4, 5, 6, 7 or 8 C atoms, —CN, —$CF_3$, —$C_2F_5$, —$C_3F_7$, —$N_3$, —$NO_2$, —CONR(13)R(14), —COOR(15), R(16)—$C_sH_{2s}$—Y— or phenyl, where any of the foregoing is unsubstituted or substituted by 1 or 2 substituents selected from F, Cl, Br, I, $CF_3$, methyl, methoxy, sulfamoyl, and methylsulfonyl, R(13) and R(14) are the same or different and each is hydrogen or alkyl having 1, 2, or 3 C atoms, R(15) is hydrogen, methyl, ethyl, phenyl, or —$C_uH_{2u}$—NR(13)R(14)

u is 2 or 3,

R(16) is hydrogen, cycloalkyl having 3, 4, 5, 6, 7, or 8 C atoms, —COOR(15), thienyl, imidazolyl, pyridyl, quinolyl, isoquinolyl, piperidyl, 1-pyrrolidinyl, N-morpholino, N-methylpiperazino, $C_tF_{2t+1}$, or phenyl, where any of the foregoing is unsubstituted or substituted by 1 or 2 substituents selected from F, Cl, Br, I, $CF_3$, methyl, methoxy, sulfamoyl, and methylsulfonyl, s is zero, 1, 2, 3, 4, 5, or 6, t is 1, 2, or 3, Y is $SO_q$, —CO—, —$SO_2$—NR(10)—, —O—, —NR(10)— or —CO—NR(10), with the proviso that R(6) is other than —$OCF_3$ or —$OC_2F_5$; and 2) a compound of the formula II, an isomer thereof, or a physiologically acceptable salt of any of the foregoing,

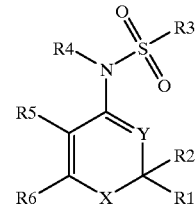

(II)

where

X is —O—, —S—, —SO—, —$SO_2$—, —NR(7)—, —CR(8a)R(8b)—, or —CO—,

R(7) is hydrogen or —($C_aH_{2a}$)—R(9), where a $CH_2$ group of the group $C_aH_{2a}$ is optionally replaced by —O—, —CH=CH—, —C≡C—, —CO—, —CO—O—, —O—CO—, —S—, —SO—, —$SO_2$—, NR(10)— or —CONR(10)—, where R(10) is hydrogen or alkyl having 1, 2, or 3 C atoms, a is zero, 1, 2, 3, 4, 5, 6, 7, or 8;

R(9) is hydrogen, $CF_3$, $C_2F_5$, $C_3F_7$, cycloalkyl having 3, 4, 5, 6, 7 or 8 C atoms, dimethylamino, diethylamino, 1-piperidyl, 1-pyrrolidinyl, 4-morpholinyl, 4-methylpiperazin-1-yl, pyridyl, thienyl, imidazolyl, or phenyl, where pyridyl, thienyl, imidazolyl, and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(7) and R(1) together form a bond, R(8a) is hydrogen, $CF_3$, $C_2F_5$, $C_3F_7$, alkyl having 1, 2, 3, 4, 5, or 6 C atoms, or phenyl, which is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(8b) is hydrogen, alkyl having 1, 2, or 3 C atoms, —OR(10), —COOR(10), CO—R(10), where R(10) is hydrogen or alkyl having 1, 2, or 3 C atoms, or one of the radicals (8a) or R(8b) together with R(1) form a bond, Y is N or CR(11), where R(11) is hydrogen or alkyl having 1, 2, or 3 C atoms, R(1) and R(2) are the same or different and each is hydrogen, $CF_3$, $C_2F_5$, $C_3F_7$, F, Cl, methoxy, alkyl having 1, 2, 3, 4, 5 or 6 C atoms, or phenyl, where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(1) and R(2) together form an alkylene chain having 2, 3, 4, 5, 6, 7, 8, 9, or 10 C atoms, R(3) is R(12)—$C_nH_{2n}$—NR(13)— or R(12)—$C_nH_{2n}$—, where one CH$_2$ group in the groups C$_n$H$_{2n}$ is optionally replaced by —O—, —CO—, —S—, —SO—, —SO$_2$—, or —NR(10a)—, R(10a) is hydrogen, methyl, or ethyl, R(12) is hydrogen, methyl, cycloalkyl having 3, 4, 5, 6, 7, or 8 C atoms, CF$_3$, C$_2$F$_5$, or C$_3$F$_7$, n is zero, 1, 2, 3, 4, 5, 6, 7, 8, 9, or 10, R(13) is hydrogen or alkyl having 1, 2, 3, 4, 5, or 6 C atoms, or R(12) and R(13) together form a bond if n is 3 or greater, or R(3) and R(4) together form an alkylene chain having 3, 4, 5, 6, 7, or 8 C atoms, where one CH$_2$ group of the alkylene chain is optionally replaced by —O—, —CO—, —S—, —SO—, —SO$_2$— or —NR(10a)—, R(10a) is hydrogen, methyl, or ethyl, R(4) is R(14)—C$_r$H$_{2r}$, where one CH$_2$ group of the group C$_r$H$_{2r}$ is optionally replaced by —O—, —CH=CH—, —C≡C—, —CO—, —CO—O—, —O—CO—, —S—, —SO—, —SO$_2$—, —NR(10b)—, or —CONR(10b)—, where R(10b) is hydrogen or alkyl having 1, 2, or 3 C atoms;

R(14) is methyl, CF$_3$, C$_2$F$_5$, C$_3$F$_7$, cycloalkyl having 3, 4, 5, 6, 7, or 8 C atoms, —OH, —COOH, —NR(23)R(24), 1-piperidyl, 1-pyrrolidinyl, 4-morpholinyl, 4-methylpiperazin-1-yl, pyridyl, thienyl, imidazolyl, or phenyl, where pyridyl, thienyl, imidazolyl and phenyl are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, R(23) and R(24) is the same or different and each is hydrogen or alkyl having 1, 2, or 3 C atoms, or R(23) and R(24) together form a chain of 4 or 5 methylene groups, one CH$_2$ group of which is optionally replaced by —O—, —S—, —NH—, —N(CH$_3$)—, or —N(benzyl)—, r is zero, 1, 2, 3, 4, 5, 6, 7, 8, 9, 10, 11, 12, 13, 14, 15, 16, 17, 18, 19, or 20, R(5) and R(6) together form a group selected from
—CR(15)=CR(16)—CR(17)=CR(18)—,
—CR(15)=CR(16)—CR(17)=N—,
—CR(15)=CR(16)—N=CR(18)—,
—CR(15)=N—CR(17)=N—,
—CR(15)=N—N=CR(18)—,
—N=CR(16)—CR(17)=N—, and
—CR(15)=CR(16)—, where either end of said group is attached to the ring at the R(5) position, R(15), R(16), R(17) and R(18) are the same or different and each is hydrogen, F, Cl, Br, I, alkyl having 1, 2, 3, 4, or 5 C atoms, cycloalkyl having 3, 4, 5, 6, 7, or 8 C atoms, —CN, —CF$_3$, —C$_2$F$_5$, —C$_3$F$_7$, —N$_3$, —NO$_2$, —Z—C$_s$H$_{2s}$—R(22), thienyl or phenyl, which is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, Z is —O—, —CO—, —CO—O—, —O—CO—, —S—, —SO—, —SO$_2$—, —SO$_2$—O—, —SO$_2$NR(10c), —NR(10c)—, or —CONR(10c)—, R(10c) is hydrogen or alkyl having 1, 2, or 3 C atoms, s is zero, 1, 2, 3, 4, 5, or 6;

R(22) is hydrogen, CF$_3$, C$_2$F$_5$, C$_3$F$_7$, cycloalkyl having 3, 4, 5, 6, 7, or 8 C atoms, —NR(19)R(20), —COOR(21), 1-piperidyl, 1-pyrrolidinyl, 4-morpholinyl, 4-methylpiperazin-1-yl, pyridyl, thienyl, imidazolyl, quinolyl, isoquinolyl or phenyl, where pyridyl, thienyl, imidazolyl, quinolyl, isoquinolyl and phenyl are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl and methylsulfonylamino, R(19) and R(20) are the same or different and each is hydrogen or alkyl having 1, 2, or 3 C atoms, or R(19) and R(20) together form a chain of 4 or 5 methylene groups, one CH$_2$ group of which is optionally replaced by —O—, —S—, —NH—, —N(CH$_3$)—, or —N(benzyl)—, R(21) is hydrogen or alkyl having 1, 2, or 3 C atoms, with the proviso that Y is other than CR(11) at the same time as X is O; and 3) a compound of the formula III, an isomer thereof, or a physiologically acceptable salt of any of the foregoing:

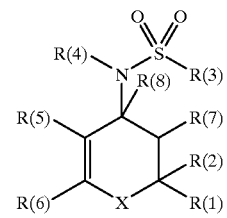

(III)

where

X is —[S(O)$_{zero, 1\ or\ 2}$]—, —NR(9)—, —[CR(9)R(23)]—, or —CO—,

R(9) is hydrogen or —(C$_n$H$_{2n}$)—R(10), n is zero, 1, 2, 3, 4, 5, 6, 7, or 8, R(10) is hydrogen, cycloalkyl having 3, 4, 5, 6, 7, or 8 C atoms, piperidyl, 1-pyrrolidinyl, N-morpholino, N-methylpiperazino, CF$_3$, C$_2$F$_5$, or C$_3$F$_7$, where one CH$_2$ group of the group C$_n$H$_{2n}$ is optionally replaced by —O—, —CH=CH—, —C≡C—, —CO—, —CO—O—, —[SO$_{zero, 1\ or\ 2}$]—, or —NR(11)—, R(11) is hydrogen, methyl, or ethyl, or R(10) is pyridyl, thienyl, imidazolyl, or phenyl, which are unsubstituted or substituted by 1 or 2 substituents selected from F, Cl, Br, I, CF$_3$, methyl, methoxy, sulfamoyl, methylsulfonyl, and methylsulfonylamino, or
R(9) together with R(1) form a bond,
R(23) is hydrogen, alkyl having 1, 2, or 3 C atoms, OH, O-alkyl having 1, 2, or 3 C atoms, COOH, COO-alkyl having 1, 2, or 3 C atoms or —CO—R(24),
R(24) is hydrogen, methyl, or ethyl,
R(1) and R(2) are the same or different and each is hydrogen, $CF_3$, $C_2F_5$, $C_3F_7$, alkyl having 1, 2, 3, 4, 5, or 6 C atoms, or phenyl,
where any of the foregoing is unsubstituted or substituted by 1 or 2 substituents selected from F, Cl, Br, I, $CF_3$, methyl, methoxy, sulfamoyl, and methylsulfonyl,
or
R(1) and R(2) together form an alkylene chain having 2, 3, 4, 5, 6, 7, 8, 9 or 10 C atoms,
R(3) is R(12)—$C_aH_{2a}$[NR(13)]$_m$—,
R(12) is hydrogen or cycloalkyl having 3, 4, 5, 6, 7, or 8 C atoms, $CF_3$, $C_2F_5$ or $C_3F_7$,
a is zero, 1, 2, 3, 4, 5, 6, 7, 8, 9, or 10,
m is zero or 1,
R(13) is hydrogen or alkyl having 1, 2, 3, 4, 5, or 6 C atoms,
or
R(12) and R(13) together are an alkylene group having 4, 5, 6, 7, or 8 C atoms,
where one $CH_2$ group of the alkylene group is optionally replaced by —O—, —[$SO_{zero, 1\ or\ 2}$]—, —CO—, or —NR(11)—,
where R(11) is hydrogen, methyl, or ethyl,
R(4) is R(14)—$C_rH_{2r}$,
r is 1, 2, 3, 4, 5, 6, 7, 8, 9, 10, 11, 12, 13, 14, 15, 16, 17, 18, 19, or 20,
R(14) is hydrogen, cycloalkyl having 3, 4, 5, 6, 7, or 8 C atoms, piperidyl, 1-pyrrolidinyl, N-morpholino, N-methylpiperazino, $CF_3$, $C_2F_5$, $C_3F_7$, pyridyl, thienyl, imidazolyl or phenyl,
where any of the foregoing is unsubstituted or substituted by 1 or 2 substituents selected from F, Cl, Br, I, $CF_3$, methyl, methoxy, sulfamoyl, methylsulfonyl, and methylsulfonylamino,
where one $CH_2$ group of the group $C_rH_{2r}$ is optionally replaced by —O—, —CH=CH—, —C☐C—, —CO—, —CO—O—, —CO—NR(11)—, —[$SO_{zero, 1\ or\ 2}$]—, or —NR(11)—,
or
R(3) and R(4) together form an alkylene chain having 3, 4, 5, 6, 7, or 8 C atoms,
where one $CH_2$ group of the alkylene chain is optionally replaced by —O—, —[$SO_{zero, 1\ or\ 2}$]—, —CO— or —NR(11)—,
R(5) and R(6) together are —CR(15)=CR(16)—CR(17)=CR(18)—, —CR(15)=CR(16)—CR(17)=N—, —CR(15)=CR(16)—N=CR(18)—, —CR(15)=N—CR(17)=N—, —CR(15)=N—N=CR(18)—, —N=CR(16)—CR(17)=N—, or —S—CR(15)=CR(16)—,
where R(15), R(16), R(17) and R(18) are the same or different and each is hydrogen, F, Cl, Br, I, alkyl having 1, 2, 3, or 4 C atoms, cycloalkyl having 3, 4, 5, 6, 7, or 8 C atoms, CN, $CF_3$, $C_2F_5$, $C_3F_7$, $N_3$, $NO_2$, —CONR(19)R(20), —COOR(21), R(22)—$C_sH_{2s}$—Z—, or phenyl,
where any of the foregoing is unsubstituted or substituted by 1 or 2 substituents selected from F, Cl, Br, I, $CF_3$, methyl, methoxy, sulfamoyl, and methylsulfonyl,
R(19) and R(20) are the same or different and each is hydrogen or alkyl having 1, 2, or 3 C atoms,
R(21) is hydrogen, methyl, ethyl, phenyl, or —$C_uH_{2u}$—NR(19)R(20),
u is 2 or 3,
where the phenyl is unsubstituted or substituted by 1 or 2 substituents selected from F, Cl, Br, I, $CF_3$, methyl, methoxy, sulfamoyl, and methylsulfonyl,
R(22) is hydrogen, cycloalkyl having 3, 4, 5, 6, 7, or 8 C atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
where any of the foregoing is unsubstituted or substituted by 1 or 2 substituents selected from F, Cl, Br, I, $CF_3$, methyl, methoxy, sulfamoyl or methylsulfonyl,
s is zero, 1, 2, 3, 4, 5, or 6,
z is —[$S(O)_{zero,\ 1\ or\ 2}$]—, —CO—, —$SO_2$—NR(11)—, —$SO_2$—O—, —O—, —NR(11)—, or —[CO—NR(11)]—,
R(7) is hydrogen, hydroxyl, alkoxy having 1, 2, 3, or 4 C atoms, acyloxy having 1, 2, 3, or 4 C atoms, Cl, Br, F, alkyl having 1, 2, 3, or 4 C atoms,
R(8) is hydrogen or alkyl having 1, 2, 3, 4, 5, or 6 C atoms, and
4) a chromane derivative of the formula IV, an isomer thereof, or a physiologically acceptable salt of any of the foregoing:

(IV)

where
R(1) and R(2) are the same or different and each is hydrogen, $CF_3$, $C_2F_5$, $C_3F_7$, alkyl having 1, 2, 3, 4, 5, or 6 C atoms, or phenyl, where any of the foregoing is unsubstituted or substituted by 1 or 2 substituents selected from F, Cl, Br, I, $CF_3$, methyl, methoxy, sulfamoyl, and methylsulfonyl,
or
R(1) and R(2) together form an alkylene chain having 2, 3, 4, 5, 6, 7, 8, 9, or 10 C atoms,
R(A) is hydroxyl, alkanoyloxy having 1, 2, 3, 4, 5, or 6 C atoms or alkylsulfonyloxy having 1, 2, 3, 4, 5, or 6 C atoms,
R(B) is hydrogen,
or
R(A) and R(B) together form a bond,
R(3) is R(9)—$C_nH_{2n}$[NR(11)]$_m$—,
R(9) is hydrogen or cycloalkyl having 3, 4, 5, 6, 7, or 8 C atoms,
n is zero, 1, 2, 3, 4, 5, 6, 7, 8, 9, or 10,
m is zero or 1,
R(11) is hydrogen or alkyl having 1, 2, 3, 4, 5, or 6 C atoms, or
R(11) and R(9) together form an alkylene group having 1, 2, 3, 4, 5, 6, 7, or 8 C atoms,
where one $CH_2$ group of the group $C_nH_{2n}$ is optionally replaced by —O—, [$SO_{zero,\ 1\ or\ 2}$], or —NR(10),
R(10) is hydrogen, methyl, or ethyl,
R(4) is R(12)—$C_rH_{2r}$,
R(12) is hydrogen, cycloalkyl having 3, 4, 5, 6, 7, or 8 C atoms, piperidyl, 1-pyrrolidinyl, N-morpholino, N-methylpiperazino, $CF_3$, $C_2F_5$, $C_3F_7$, pyridyl, thienyl, imidazolyl or phenyl,
where pyridyl, thienyl, imidazolyl, or phenyl are unsubstituted or substituted by 1 or 2 substituents selected from F, Cl, Br, I, $CF_3$, methyl, methoxy, sulfamoyl, methylsulfonyl and methylsulfonylamino,
r is zero, 1, 2, 3, 4, 5, 6, 7, 8, 9, 10, 11, 12, 13, 14, 15, 16, 17, 18, 19, or 20,
where one $CH_2$ group of the group $C_rH_{2r}$ is optionally replaced by —O—, >CH=CH<, —C≡C—, —CO—, —CO—O—, $SO_{zero,\ 1\ or\ 2}$— or —NR(10)—,
R(5), R(6), R(7) and R(8) are the same or different and each is hydrogen, F, Cl, Br, I, alkyl having 1, 2, 3, 4, 5, or 6 C atoms, cycloalkyl having 3, 4, 5, 6, 7 or 8 C atoms, —CN, —$CF_3$, —$C_2F_5$, —$C_3F_7$, —$N_3$, —$NO_2$, —CONR(13)R(14), —COOR(15), R(16)—$C_sH_{2s}$—Y— or phenyl,
where any of the foregoing is unsubstituted or substituted by 1 or 2 substituents selected from F, Cl, Br, I, $CF_3$, methyl, methoxy, sulfamoyl and methylsulfonyl,
R(13) and R(14) are the same or different and each is hydrogen or alkyl having 1, 2, or 3 C atoms,
R(15) is hydrogen, methyl, ethyl, phenyl or —$C_uH_{2u}$—NR(13)R(14),
u is 2 or 3,
R(16) is hydrogen, cycloalkyl having 3, 4, 5, 6, 7, or 8 C atoms, —COOR(15), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$ or phenyl,
where any of the foregoing is unsubstituted or substituted by 1 or 2 substituents selected from F, Cl, Br, I, $CF_3$, methyl, methoxy, sulfamoyl and methylsulfonyl,
s is zero, 1, 2, 3, 4, 5, or 6,
Y —S—, —SO—, —$SO_2$—, —CO—, —$SO_2$—NR(10)—, —O—, —NR(10)—, or —CO—NR(10),
with the proviso that two of the substituents R(5), R(6), R(7) and R(8) are other than hydrogen; and 5) a compound of the formula V, an isomer thereof, or a physiologically acceptable salt of any of the foregoing:

(V)

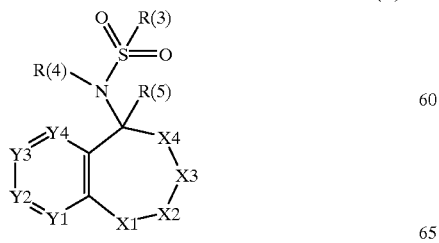

where
X1 is —O—, —S—, —SO—, —$SO_2$—, —CR(1)R(2)—, —NR(6)—, —CO—, or —CR(1)R(7)—,
R(1) and R(2) are the same or different and each is hydrogen, $CF_3$, $C_2F_5$, $C_3F_7$, alkyl having 1, 2, 3, 4, 5, or 6 C atoms, or phenyl,
where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
or
R(1) and R(2) together form an alkylene chain having 2, 3, 4, 5, 6, 7, 8, 9 or 10 C atoms,
R(6) is hydrogen or —$C_nH_{2n}$—R(8),
where one $CH_2$ group of the group $C_nH_{2n}$ is optionally replaced by —O—, —CH=CH—, —C≡C—, —CO—, —CO—O—, —O—CO—, —S—, —SO—, —$SO_2$—, —NR(9)—, or —CONR(9)—, R(9) is hydrogen or alkyl having 1, 2, or 3 C atoms,
n is zero, 1, 2, 3, 4, 5, 6, 7, or 8,
R(8) is hydrogen, $CF_3$, $C_2F_5$, $C_3F_7$, cycloalkyl having 3, 4, 5, 6, 7, or 8 C atoms, dimethylamino, diethylamino, 1-piperidyl, 1-pyrrolidinyl, 4-morpholinyl, 4-methylpiperazin-1-yl, pyridyl, thienyl, imidazolyl or phenyl,
where pyridyl, thienyl, imidazolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
X2 is —CR(1)R(2)—, —CR(2)R(10)—, —O—, —S—, —SO—, —$SO_2$—, or —NR(6)—,
where the radicals R(1), R(2), and R(6) are as defined under X1, and the radicals R(1), R(2), and R(6) in X2 are the same or different as X1,
R(10) together with R(7) forms a bond,
X3 is —CR(1)R(2)—, —O—, —S—, —SO—, —$SO_2$— or —NR(6)—,
where the radicals R(1), R(2), and R(6) are as defined under X1, and the radicals R(1), R(2), and R(6) in X2 are the same or different as X1,
X4 is —CR(1)R(2)—, —NR(6)—, —NR(11)—, —CH(OR(30))—, or —CR(2)R(11)—,
where the radicals R(1), R(2), and R(6) are as defined under X1, and the radicals R(1), R(2), and R(6) in X2 are the same or different as X1,
R(30) is hydrogen, alkyl having 1, 2, or 3 C atoms, or acyl having 1, 2, 3, or 4 C atoms,
R(11) together with R(5) forms a bond,
Y1, Y2, Y3, and Y4 are the same or different and each is —CR(12)— or N, where at most 2 of the groups Y1, Y2, Y3 and Y4 are simultaneously N,
the radicals R(12) are the same or different and each is hydrogen, F, Cl, Br, I, alkyl having 1, 2, 3, 4, or 5 C atoms, cycloalkyl having 3, 4, 5, 6, 7, or 8 C atoms, CN, $CF_3$, $C_2F_5$, $C_3F_7$, $N_3$, $NO_2$, —Z—$C_mH_{2m}$—R(13), or phenyl,
where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
Z is —O—, —CO—, —CO—O—, —O—CO—, —S—, —SO—, —$SO_2$—, —$SO_2$NR(14)—, —NR(14)—, or —CONR(14)—, R(14) is hydrogen or alkyl having 1, 2, or 3 C atoms, m is zero, 1, 2, 3, 4, 5, or 6, R(13) is hydrogen, $CF_3$, $C_2F_5$, $C_3F_7$, cycloalkyl having 3, 4, 5, 6, 7, or 8 C atoms, —NR(15)R(16), —CONR(15)R(16), —OR(30a), phenyl, thienyl, or an N-containing heterocycle having 1, 2, 3, 4, 5, 6, 7, 8 or 9 C atoms, where phenyl, thienyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(15) and R(16) are the same or different and each is hydrogen or alkyl having 1, 2, or 3 C atoms, or R(15) and R(16) together are a chain of 4 or 5 methylene groups, one $CH_2$ group of which is optionally replaced by —O—, —S—, —NH—, —N($CH_3$)— or —N(benzyl)—, R(30a) is hydrogen, alkyl having 1, 2, or 3 C atoms, or acyl having 1, 2, 3, or 4 C atoms, or Y1 and Y2 together are an S atom and Y3 and Y4 are each —CR(12)—, where the radicals R(12) are the same or different and each is as defined under Y1, Y2, Y3, and Y4, R(3) is R(17)—$C_xH_{2x}$—NR(18)— or R(17)—$C_xH_{2x}$—, where one $CH_2$ group in the groups $C_xH_{2x}$ is optionally replaced by —O—, —CO—, —S—, —SO—, —$SO_2$—, or —NR(19)—, where R(19) is hydrogen, methyl, or ethyl, R(17) is hydrogen, methyl, cycloalkyl having 3, 4, 5, 6, 7, or 8 C atoms, $CF_3$, $C_2F_5$, or $C_3F_7$, x is zero, 1, 2, 3, 4, 5, 6, 7, 8, 9, or 10, R(18) is hydrogen or alkyl having 1, 2, 3, 4, 5, 6, 7, or 8 C atoms, or R(18) and R(17) together form a bond if x is 3 or greater, or R(3) is phenyl, which is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(3) together with R(4) are an alkylene chain having 3, 4, 5, 6, 7, or 8 C atoms, where one $CH_2$ group of the alkylene chain is optionally replaced by —O—, —CO—, —S—, —SO—, or $SO_2$, R(4) is —$C_rH_{2r}$—R(20), where one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(21)—, or —CONR(21)—, R(21) is hydrogen or alkyl having 1, 2, or 3 C atoms, r is zero, 1, 2, 3, 4, 5, 6, 7, 8, 9, 10, 11, 12, 13, 14, 15, 16, 17, 18, 19, or 20, R(20) is hydrogen, methyl, $CF_3$, $C_2F_5$, $C_3F_7$, cycloalkyl having 3, 4, 5, 6, 7 or 8 C atoms, —NR(22)R(23), phenyl, thienyl, or an N-containing heterocycle having 1, 2, 3, 4, 5, 6, 7, 8, or 9 C atoms, where phenyl, thienyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(22) and R(23) are the same or different and each is hydrogen or alkyl having 1, 2, or 3 C atoms, or R(22) and R(23) together are a chain of 4 or 5 methylene groups one $CH_2$ group of which is optionally replaced by —O—, —S—, —NH—, —N($CH_3$)— or —N(benzyl)—, R(5) is hydrogen or together with R(11) forms a bond; and 6) a compound of the formula VI, an isomer thereof, or a physiologically acceptable salt of any of the foregoing:

(VI)

in which:

R(1) and R(2) are the same or different and each is hydrogen, $CF_3$, $C_2F_5$, $C_3F_7$, alkyl having 1, 2, 3, 4, 5, or 6 C atoms, or phenyl, where any of the foregoing is unsubstituted or substituted by 1 or 2 substituents selected from F, Cl, Br, I, $CF_3$, methyl, methoxy, sulfamoyl, and methylsulfonyl, or R(1) and R(2) together form an alkylene chain having 2, 3, 4, 5, 6, 7, 8, 9, or 10 C atoms, where one $CH_2$ group of the alkylene chain is optionally replaced by —O—, —CO—, —S—, —SO—, —$SO_2$—, or —NR(10)—, R(10) is hydrogen or alkyl having 1, 2, or 3 C atoms, R(3) is R(12)—$C_aH_{2a}$[NR(13)]$_m$—, R(12) is hydrogen or cycloalkyl having 3, 4, 5, 6, 7, or 8 C atoms, $CF_3$, $C_2F_5$, or $C_3F_7$, a is zero, 1, 2, 3, 4, 5, 6, 7, 8, 9, or 10, m is zero or 1, R(13) is hydrogen or alkyl having 1, 2, 3, 4, 5, or 6 C atoms, or R(12) and R(13) together form an alkylene group having 4, 5, 6, 7 or 8 C atoms, where one $CH_2$ group of the alkylene group is optionally replaced by —O—, —[$SO_{zero, 1\ or\ 2}$]—, —CO— or —NR(10)—, R(10) is hydrogen or alkyl having 1, 2, or 3 C atoms, R(4) is R(14)—$C_rH_{2r}$ where r is zero, 1, 2, 3, 4, 5, 6, 7, 8, 9, 10, 11, 12, 13, 14, 15, 16, 17, 18, 19, or 20, R(14) is hydrogen, cycloalkyl having 3, 4, 5, 6, 7, or 8 C atoms, piperidyl, 1-pyrrolidinyl, N-morpholino, N-methylpiperazino, $CF_3$, $C_2F_5$, $C_3F_7$, pyridyl, thienyl, imidazolyl, or phenyl, where any of the foregoing is unsubstituted or substituted by 1 or 2 substituents selected from F, Cl, Br, I, CF$_3$, methyl, methoxy, sulfamoyl, methylsulfonyl, and methylsulfonylamino,
where one CH$_2$ group of the group C$_r$H$_{2r}$ is optionally replaced by —O—, —CH=CH—, —C≡C—, —CO—, —CO—O—, —CO—NR(11)—, —[SO$_{zero, 1\ or\ 2}$]—, or —NR(11)—,
R(11) is hydrogen or —(C$_a$H$_{2a}$)—R(10),
where one CH$_2$ group of the group C$_a$H$_{2a}$ is optionally replaced by —O—, —CH=CH—, —C≡C—, —CO—, —CO—O—, —O—CO—, —S—, —SO—, —SO$_2$—, NR(10)—, or —CONR(10)—,
R(10) is hydrogen or alkyl having 1, 2, or 3 C atoms, or R(3) and R(4) together form an alkylene chain having 3, 4, 5, 6, 7 or 8 C atoms,
where one CH$_2$ group of the alkylene chain is optionally replaced by —O—, —[SO$_{zero, 1\ or\ 2}$]—, —CO—, or —NR(11)—, where
R(11) is hydrogen or —(C$_a$H$_{2a}$)—R(10),
where one CH$_2$ group of the group C$_a$H$_{2a}$ is optionally replaced by —O—, —CH=CH—, —C≡C—, —CO—, —CO—O—, —O—CO—, —S—, —SO—, —SO$_2$—, NR(10)—, or —CONR(10)—,
R(10) is hydrogen or alkyl having 1, 2, or 3 C atoms, R(5) and R(6) are
—CR(15)=CR(16)—CR(17)=N—,
—CR(15)=CR(16)—N=CR(17)—,
—CR(15)=N—CR(17)=N—,
—CR(15)=N—N=CR(17)—,
—N=CR(16)—CR(17)=N— or
—S—CR(15)=CR(16)—;
R(15), R(16), and R(17) are the same or different and each is hydrogen, F, Cl, Br, I, alkyl having 1, 2, 3, or 4 C atoms, cycloalkyl having 3, 4, 5, 6, 7, or 8 C atoms, CN, CF$_3$, C$_2$F$_5$, C$_3$F$_7$, N$_3$, NO$_2$, —CONR(19)R(21), —COOR(21), R(22)—C$_s$H$_{2s}$—Z—, or phenyl,
where any of the foregoing is unsubstituted or substituted by 1 or 2 substituents selected from F, Cl, Br, I, CF$_3$, methyl, methoxy, sulfamoyl and methylsulfonyl,
R(19) is hydrogen or alkyl having 1, 2, or 3 C atoms,
R(21) is hydrogen, methyl, ethyl, phenyl or —C$_u$H$_{2u}$—NR(19)R(20),
where the phenyl is unsubstituted or substituted by 1 or 2 substituents selected from F, Cl, Br, I, CF$_3$, methyl, methoxy, sulfamoyl, and methylsulfonyl, where
R(20) is hydrogen or alkyl having 1, 2, or 3 C atoms,
u is 2 or 3,
R(22) is hydrogen, cycloalkyl having 3, 4, 5, 6, 7 or 8 C atoms, —COOR(21), CONR(19)R(21), thienyl, imidazolyl, pyridyl, quinolyl, isoquinolyl, piperidyl, 1-pyrrolidinyl, N-morpholino, N-methylpiperazino, CF$_3$, C$_2$F$_5$, C$_3$F$_7$ or phenyl,
where any of the foregoing is unsubstituted or substituted by 1 or 2 substituents selected from F, Cl, Br, I, CF$_3$, methyl, methoxy, sulfamoyl and methylsulfonyl,
s is zero, 1, 2, 3, 4, 5, or 6,
Z is —[S(O)$_{zero, 1\ or\ 2}$]—, —CO—, —SO$_{(0, 1\ or\ 2)}$—NR(11)—, —SO$_2$—O—, —O—, —NR(11)—, or —[CO—NR(11)]—, R(7) is hydrogen, hydroxyl, alkoxy having 1, 2, 3, or 4 C atoms, acyloxy having 1, 2, 3, or 4 C atoms, Cl, Br, F, alkyl having 1, 2, 3, or 4 C atoms,
R(8) is hydrogen or alkyl having 1, 2, 3, 4, 5, or 6 C atoms; and
7) a compound of the formula VII, an isomer thereof, or a physiologically acceptable salt of any of the foregoing:

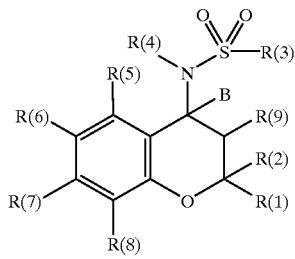

(VII)

where
R(1) and R(2) are the same or different and each is hydrogen, CF$_3$, C$_2$F$_5$, C$_3$F$_7$, alkyl having 1, 2, 3, 4, 5 or 6 C atoms or phenyl,
where any of the foregoing is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, or R(1) and R(2) together are an alkylene chain having 2, 3, 4, 5, 6, 7, 8, 9, or 10 C atoms,
R(3) is R(10)—C$_n$H$_{2n}$—NR(11)— or R(10)—C$_n$H$_{2n}$—,
where one CH$_2$ group in the groups C$_n$H$_{2n}$ is optionally replaced by —O—, —CO—, —S—, —SO—, —SO$_2$—, or —NR(12a)—;
R(12a) is hydrogen, methyl or ethyl,
R(10) is hydrogen, methyl, cycloalkyl having 3, 4, 5, 6, 7, or 8 C atoms, CF$_3$, C$_2$F$_5$, or C$_3$F$_7$,
n is zero, 1, 2, 3, 4, 5, 6, 7, 8, 9, or 10,
R(11) is hydrogen or alkyl having 1, 2, 3, 4, 5, or 6 C atoms, or R(10) and R(11) together form a bond if n is 3 or greater,
R(4) is R(13)—C$_r$H$_{2r}$—Z—C$_q$H$_{2q}$—,
q is 0, 1, 2, 3, 4, 5, 6, 7, or 8,
r is 0, 1, 2, 3, 4, 5, 6, 7, or 8,
Z is —CO—NR(14)—,
—OCO—NR(14)—,
—O—C$_x$H$_{2x}$—O—,
—O—C$_x$H$_{2x}$—NR(14)—,
—O—C$_x$H$_{2x}$—CO—O,
—CO—O—C$_x$H$_{2x}$—O— or
—CO—O—C$_x$H$_{2x}$—NR(14)—,
where either end of the groups defined by Z is attached to C$_r$H$_{2r}$,
x is 2, 3, or 4,
R(14) is hydrogen, alkyl having 1, 2, or 3 C atoms, —C$_y$H$_{2y}$—OR(12b), —C$_y$H$_{2y}$—NR(12b)$_2$,
where R(12b) is hydrogen, methyl, or ethyl,
y is 2 or 3,
R(13) is H, CF$_3$, C$_2$F$_5$, C$_3$F$_7$, cycloalkyl having 3, 4, 5, 6, 7 or 8 C atoms, —NR(15)R(16), —CONR (15)R(16), —C(=NR(17))NR(15)R(16), —OR (17), —COOR(17), phenyl or an N-containing heterocycle having 1, 2, 3, 4, 5, 6, 7, 8, or 9 C atoms,
  where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, aminosulfonyl and methylsulfonylamino,
R(15) and R(16) are the same or different and each is hydrogen, alkyl having 1, 2, 3, or 4 C atoms, or —$C_zH_{2z}$-phenyl,
  where phenyl is unsubstituted or substituted by 1 or 2 substituents selected from F, Cl, Br, $CF_3$, $NO_2$, CN, OH, methyl, ethyl, methoxy, dimethylamino, sulfamoyl, methylsulfonyl, aminosulfonyl and methylsulfonylamino,
or
R(15) and R(16) together form a chain of 4 or 5 methylene groups, one $CH_2$ group of which is optionally replaced by —O—, —S—, —NH—, —N($CH_3$)—, or —N(benzyl)—,
R(17) is hydrogen or alkyl having 1, 2, or 3 C atoms,
R(5), R(6), R(7), and R(8) are the same or different and each is hydrogen, F, Cl, Br, I, alkyl having 1, 2, 3, 4, or 5 C atoms, cycloalkyl having 3, 4, 5, 6, 7, or 8 C atoms, —CN, —$CF_3$, —$C_2F_5$, —$C_3F_7$, —$N_3$, —$NO_2$, —Y—$C_sH_{2s}$—R(18), or phenyl,
  where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
  Y is —O—, —CO—, —CO—O—, —O—CO—, —S—, —SO—, —$SO_2$—, —$SO_2$—O—, —$SO_2$NR(10c), —NR(10c)—, or —CONR(10c)—, where R(10c) is hydrogen or alkyl having 1, 2, or 3 C atoms,
  s is zero, 1, 2, 3, 4, 5, or 6;
R(18) is hydrogen, $CF_3$, $C_2F_5$, $C_3F_7$, cycloalkyl having 3, 4, 5, 6, 7 or 8 C atoms, —COOR(21), 1-piperidyl, 1-pyrrolidinyl, 4-morpholinyl, 4-methylpiperazin-1-yl, pyridyl, thienyl, imidazolyl, quinolyl, isoquinolyl, or phenyl,
  where pyridyl, thienyl, imidazolyl, quinolyl, isoquinolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
R(21) is hydrogen or alkyl having 1, 2, or 3 C atoms,
R(9) is hydrogen, OR(10d) or OCOR(10d), where R(10d) is hydrogen or alkyl having 1, 2 or 3 C atoms,
B is hydrogen,
or
R(9) and B together form a bond; and
8) a compound of the formula VIII, an isomer thereof, or a physiologically acceptable salt of any of the foregoing:

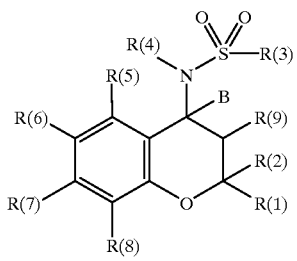

(VIII)

where
R(1) and R(2) are the same or different and each is hydrogen, $CF_3$, $C_2F_5$, $C_3F_7$, alkyl having 1, 2, 3, 4, 5, or 6 C atoms, or phenyl,
  where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
or
R(1) and R(2) together form an alkylene chain having 2, 3, 4, 5, 6, 7, 8, 9, or 10 C atoms,
R(3) is R(10)—$C_nH_{2n}$—NR(11)— or R(10)—$C_nH_{2n}$—,
  where one $CH_2$ group in the groups $C_nH_{2n}$ is optionally replaced by —O—, —CO—, —S—, —SO—, —$SO_2$—, or —NR(12a)—,
  where R(12a) is hydrogen, methyl or ethyl,
  R(10) is hydrogen, methyl, cycloalkyl having 3, 4, 5, 6, 7, or 8 C atoms, $CF_3$, $C_2F_5$, or $C_3F_7$,
  n is zero, 1, 2, 3, 4, 5, 6, 7, 8, 9, or 10,
  R(11) is hydrogen or alkyl having 1, 2, 3, 4, 5, or 6 C atoms,
  or
  R(10) and R(11) together form a bond if n is 3 or greater,
or
R(3) together with R(4) form an alkylene chain having 3, 4, 5, 6, 7, or 8 C atoms,
  where one $CH_2$ group of the alkylene chain is optionally replaced by —O—, —CO—, —S—, —SO—, —$SO_2$—, or —NR(12a)—,
  where R(12a) is hydrogen, methyl, or ethyl,
R(4) is R(13)—$C_rH_{2r}$,
  where one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(14)—, or —CONR(14)—,
  where R(14) is hydrogen, alkyl having 1, 2, or 3 C atoms, —$C_yH_{2y}$—OR(12b), or —$C_yH_{2y}$—NR(12b)$_2$,
    where R(12b) is hydrogen, methyl, or ethyl,
    y is 2 or 3,
  R(13) is H, $CF_3$, $C_2F_5$, $C_3F_7$, cycloalkyl having 3, 4, 5, 6, 7, or 8 C atoms, —NR(15)R(16), —CONR(15)R(16), —OR(17), —COOR(17), phenyl, or an N-containing heterocycle having 1, 2, 3, 4, 5, 6, 7, 8, or 9 C atoms,
    where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(15) and R(16) are the same or different and each is hydrogen or alkyl having 1, 2, 3, or 4 C atoms, or R(15) and R(16) together form a chain of 4 or 5 methylene groups, one $CH_2$ group of which is optionally replaced by —O—, —S—, —NH—, —N($CH_3$)—, or —N(benzyl)—, R(17) is hydrogen, alkyl having 1, 2, or 3 C atoms, —$C_xH_{2x}$OR(12c), where R(12c) is hydrogen, methyl or ethyl, x is 2 or 3, r is zero, 1, 2, 3, 4, 5, 6, 7, 8, 9, 10, 11, 12, 13, 14, 15, 16, 17, 18, 19, or 20, at least one of the substituents R(5), R(6), R(7) and R(8) is —Y—$C_sH_{2s}$—R(18), thienyl, furyl, or an N-containing heterocycle having 1, 2, 3, 4, 5, 6, 7, 8, or 9 C atoms, where thienyl, furyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, methylamino, dimethylamino, ethylamino, diethylamino, sulfamoyl, methylsulfonyl and methylsulfonylamino, Y is —O—, —CO—, —O—CO—, —S—, —SO—, —$SO_2$—, —$SO_2$—O—, —$SO_2$NR(12d)—, —NR(12d)—, or —CONR(12d)—, where the attachment to the benzene ring is, in each case, effected through the atom depicted on the left of each of the above groups;

where R(12d) is hydrogen, methyl or ethyl, s is 1, 2, 3, 4, 5, or 6,

R(18) is substituted phenyl carrying one or two substituents selected from $NO_2$, CN, $NH_2$, N(methyl)$_2$, OH, ethyl, —COOH, —COOmethyl, —COOethyl, —$CONH_2$, and —CON(methyl)$_2$, or R(18) is a substituted N-containing heterocycle having 1, 2, 3, 4, 5, 6, 7, 8, or 9 C atoms carrying 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(18) is —OR(19), —$SO_2$R(19), —NR(19)R(20), or —CONR(19)R(20), where R(19) and R(20) are the same or different and each is $C_tH_{2t}$—R(21), t is zero, 1, 2, 3, 4, 5, or 6, R(21) is hydrogen, $CF_3$, $C_2F_5$, $C_3F_7$, cycloalkyl having 3, 4, 5, 6, 7, or 8 C atoms, NR(22)R(23), —OR(24), phenyl, thienyl, or an N-containing heterocycle having 1, 2, 3, 4, 5, 6, 7, 8, or 9 C atoms, where phenyl, thienyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(22) and R(23) are the same or different and each is hydrogen, alkyl having 1, 2 or 3 C atoms, or R(22) and R(23) together are a chain of 4 or 5 methylene groups, one $CH_2$ group of which is optionally replaced by —O—, —S—, —NH—, —N($CH_3$)—, or —N(benzyl)—, R(24) is hydrogen, alkyl having 1, 2, or 3 C atoms, and in each case the other substituents R(5), R(6), R(7), and R(8), which are not defined above are the same or different and each is hydrogen, F, Cl, Br, I, alkyl having 1, 2, 3, 4, or 5 C atoms, cycloalkyl having 3, 4, 5, 6, 7, or 8 C atoms, CN, $CF_3$, $NO_2$, OR(12e), or NR(12e)R(12f), where R(12e) and R(12f) are the same or different and each is hydrogen or alkyl having 1, 2, 3, or 4 C atoms, R(9) is hydrogen, OR(12g), or OCOR(12g), where R(12g) is hydrogen or alkyl having 1, 2, or 3 C atoms, B is hydrogen, or R(9) and B together form a bond; and 9) a compound of the formula IX, an isomer thereof, or a physiologically acceptable salt of any of the foregoing:

(IX)

where R(5) is attached to one of the positions labeled 5, 6, 7, and 8, and where R(1) and R(2) are the same or different and each is hydrogen, $CF_3$, $C_2F_5$, $C_3F_7$, alkyl having 1, 2, 3, 4, 5 or 6 C atoms or phenyl, where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(1) and R(2) together form an alkylene chain having 2, 3, 4, 5, 6, 7, 8, 9, or 10 C atoms, R(3) is R(10)—$C_nH_{2n}$—NR(11)— or R(10)—$C_nH_{2n}$—, where one $CH_2$ group in the group $C_nH_{2n}$ is optionally replaced by —O—, —CO—, —S—, —SO—, —$SO_2$—, or —NR(12a)—, where R(12a) is hydrogen, methyl, or ethyl, R(10) is hydrogen, methyl, cycloalkyl having 3, 4, 5, 6, 7, or 8 C atoms, $CF_3$, $C_2F_5$, or $C_3F_7$, n is zero, 1, 2, 3, 4, 5, 6, 7, 8, 9, or 10, R(11) is hydrogen or alkyl having 1, 2, 3, 4, 5, or 6 C atoms, or R(10) and R(11) together form a bond if n is 3 or greater;

or

R(3) together with R(4) is an alkylene chain having 3, 4, 5, 6, 7, or 8 C atoms, where one $CH_2$ group of the alkylene chain is optionally replaced by —O—, —CO—, —S—, —SO—, —$SO_2$—, or —NR(12a)—, where R(12a) is hydrogen, methyl, or ethyl, R(4) is R(13)—$C_rH_{2r}$, where one $CH_2$ group of the group $C_rH_{2r}$ is optionally replaced by —O—, —CH=CH—, —C≡C—, —CO—, —CO—O—, —O—CO—, —S—, —SO—, —SO$_2$—, or —NR(14)—,
where R(14) is hydrogen or alkyl having 1, 2, or 3 C atoms, R(13) is CH$_3$, CF$_3$, C$_2$F$_5$, C$_3$F$_7$, cycloalkyl having 3, 4, 5, 6, 7, or 8 C atoms, NR(15)R(16), phenyl, or an N-containing heterocycle having 1, 2, 3, 4, 5, 6, 7, 8, or 9 C atoms,
where phenyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, R(15) and R(16) together are a chain of 4 or 5 methylene groups, one CH$_2$ group of which is optionally replaced by —O—, —S—, —NH—, —N(methyl)—, or —N(benzyl)—, r is zero, 1, 2, 3, 4, 5, 6, 7, 8, 9, 10, 11, 12, 13, 14, 15, 16, 17, 18, 19, or 20, R(5) is —Y—C$_s$H$_{2s}$—R(18) or phenyl,
where the phenyl is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, Y is —O—, —S—, or —NR(10c)—, where R(10c) is hydrogen or alkyl having 1, 2, or 3 C atoms, s is 1, 2, 3, 4, 5, 6, 7, or 8, R(18) is hydrogen, CF$_3$, C$_2$F$_5$, C$_3$F$_7$, cycloalkyl having 3, 4, 5, 6, 7, or 8 C atoms, —COOR(21), NR(15a)R(16a), an unsubstituted N-containing heterocycle having 1, 2, 3, 4, 5, 6, 7, 8, or 9 C atoms, phenyl, or thienyl,
where phenyl and thienyl are unsubstituted or substituted by 1 or 2 substituents selected from F, Cl, Br, I, CF$_3$, methyl, methoxy, sulfamoyl, methylsulfonyl, and methylsulfonylamino, R(15a) and R(16a) together form a chain of 4 or 5 methylene groups, one CH$_2$ group of which is optionally replaced by —O—, —S—, —NH—, —N(methyl)—, or —N(benzyl)—, R(21) is hydrogen or alkyl having 1, 2, or 3 C atoms, R(6) is OR(10d) or OCOR(10d),
where R(10d) is hydrogen or alkyl having 1, 2, or 3 C atoms, B is hydrogen,
or
R(6) and B together form a bond, and 10) a compound of the formula X, an isomer thereof, or a physiologically acceptable salt of any of the foregoing:

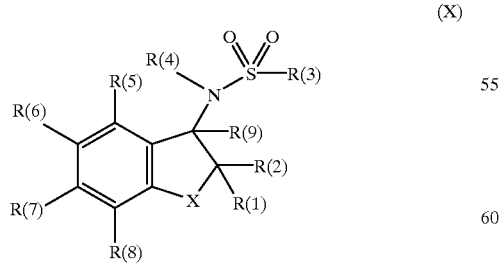

(X)

where
R(1) and R(2) are the same or different and each is hydrogen, CF$_3$, alkyl having 1, 2, 3, 4, 5, or 6 C atoms, or
R(2) and R(9) together form a bond,
or R(2) is —OR(10a),
where R(10a) is hydrogen, acetyl, or alkyl having 1, 2, or 3 C atoms, R(3) is R(10b)—C$_n$H$_{2n}$—NR(11)— or R(10b)—C$_n$H$_{2n}$—,
where one CH$_2$ group in the groups C$_n$H$_{2n}$ is optionally replaced by —O—, —CO—, —S—, —SO—, —SO$_2$—, or —NR(12a)—, R(12a) is hydrogen, methyl or ethyl, R(10b) is methyl, cycloalkyl having 3, 4, 5, 6, 7, or 8 C atoms, CF$_3$, C$_2$F$_5$, or C$_3$F$_7$, n is zero, 1, 2, 3, 4, 5, 6, 7, 8, 9, or 10, R(11) is hydrogen or alkyl having 1, 2, 3, 4, 5, or 6 C atoms, or
R(10b) and R(11) together form a bond if n is greater than 2, or
R(3) together with R(4) form an alkylene chain having 3, 4, 5, 6, 7, or 8 C atoms,
where one CH$_2$ group of the alkylene chain is optionally replaced by —O—, —CO—, —S—, —SO—, —SO$_2$—, or —NR(12a)—, where R(12a) is hydrogen, methyl, or ethyl, R(4) is R(13)—C$_r$H$_{2r}$,
where one CH$_2$ group of the group C$_r$H$_{2r}$ is optionally replaced by —O—, —CH=CH—, —C≡C—, —CO—, —CO—O—, —O—CO—, —S—, —SO—, —SO$_2$—, —NR(14)—, or —CONR(14)—, R(14) is hydrogen, alkyl having 1, 2, or 3 C atoms, —C$_y$H$_{2y}$—OR(12b), or —C$_y$H$_{2y}$—NR(12b)$_2$,
where R(12b) is hydrogen, methyl, or ethyl,
y is 2 or 3, R(13) is CH$_3$, CF$_3$, C$_2$F$_5$, C$_3$F$_7$, cycloalkyl having 3, 4, 5, 6, 7, or 8 C atoms, —NR(15)R(16), —CONR(15)R(16), —OR(17), —COOR(17), phenyl, or an N-containing heterocycle having 1, 2, 3, 4, 5, 6, 7, 8, or 9 C atoms,
where phenyl and the N-containing heterocycle are unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino, R(15) and R(16) are the same or different and each is hydrogen or alkyl having 1, 2, 3 or 4 C atoms, or
R(15) and R(16) together form a chain of 4 or 5 methylene groups, one CH$_2$ group of which is optionally replaced by —O—, —S—, —NH—, —N(CH$_3$)— or —N(benzyl)—, R(17) is hydrogen, alkyl having 1, 2, or 3 C atoms, —C$_z$H$_{2z}$OR(12c),
where R(12c) is hydrogen, methyl, or ethyl,
z is 2 or 3, r is zero, 1, 2, 3, 4, 5, 6, 7, 8, 9, 10, 11, 12, 13, 14, 15, 16, 17, 18, 19, or 20, R(5), R(6), R(7) and R(8) are the same or different and each is hydrogen, F, Cl, Br, I, alkyl having 1, 2, 3, 4, or 5 C atoms, cycloalkyl having 3, 4, 5, 6, 7, or 8 C atoms, —CN, —CF$_3$, —C$_2$F$_5$, —C$_3$F$_7$, —N$_3$, —NO$_2$, —Y—C$_s$H$_{2s}$—R(18), phenyl, thienyl, furyl, or an N-containing heterocycle having 1, 2, 3, 4, 5, 6, 7, 8 or 9 C atoms, where phenyl, thienyl, furyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, Y is —O—, —CO—, —CO—O—, —O—CO—, —S—, —SO—, —$SO_2$—, —O—$SO_2$—, —$SO_2$NR(10c)— or —CONR(10c)—, where the attachment to the benzene ring is, in each case, effected through the atom depicted on the left of each of the above groups,
  where R(10c) is hydrogen or alkyl having 1, 2, or 3 C atoms, s is zero, 1, 2, 3, 4, 5, or 6, R(18) is hydrogen, methyl, $CF_3$, $C_2F_5$, $C_3F_7$, cycloalkyl having 3, 4, 5, 6, 7, or 8 C atoms, —OR(21), —COOR(21), —NR(15a)R(16a), —CONR(15a)R(16a), phenyl, or an N-containing heterocycle having 1, 2, 3, 4, 5, 6, 7, 8, or 9 C atoms,
  where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(15a) and R(16a) are the same or different and each is hydrogen or alkyl having 1, 2, 3, or 4 C atoms, or R(15a) and R(16a) together are a chain of 4 or 5 methylene groups, one $CH_2$ group of which is optionally replaced by —O—, —S—, —NH—, —N($CH_3$)— or —N(benzyl)—, R(21) is hydrogen or alkyl having 1, 2, or 3 C atoms, R(9) is hydrogen or together with R(2) forms a bond, X is —CR(22)R(23)—, —O—, —NR(24)—, —S—, —SO—, or —$SO_2$—, R(22) and R(23) are the same or different and each is hydrogen, $CF_3$, alkyl having 1, 2, 3, 4, 5, or 6 C atoms, R(24) is hydrogen, alkyl having 1, 2, 3, 4, 5, or 6 C atoms, or phenyl, which is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, and 11) a compound of the formula XI, an isomer thereof, or a physiologically acceptable salt of any of the foregoing:

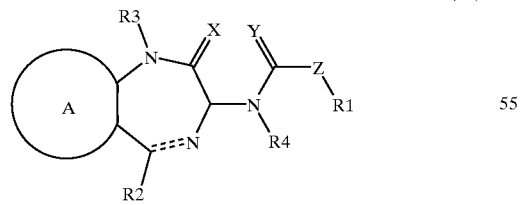

(XI)

where
A is substituted or unsubstituted thienyl or pyridyl,
X is O, S, =N—NH2, =N—OH, H2,
Y is O, NCN, H2,
Z is alkyl or alkenyl, unsubstituted or substituted by phenyl or cycloalkyl, where one or more $CH_2$ groups is optionally replaced by O, S, NH, or a bond, R1 is phenyl, unsubstituted or substituted, alkyl, cycloalkyl, a mono- or bicyclic heterocycle, or indanyl, R2 is phenyl, unsubstituted or substituted, alkyl, cycloalkyl, 2- or 3-furyl, or N-mono- or -bis-alkyl, R3 is H or alkyl, unsubstituted or substituted by N($CH_3$)$_2$, OH, or fluoroalkyl;

R4 is H, alkyl which is optionally interrupted by one or two oxygen atoms; and 12) a compound of the formula XII, an isomer thereof, or a physiologically acceptable salt of any of the foregoing:

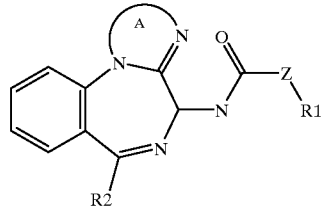

(XII)

where
A is a 2- or 3-membered chain consisting of C atoms, but in which one or more members is optionally nitrogen or oxygen, said chain being unsubstituted or substituted by alkyl, Z is alkyl or alkenyl, which are unsubstituted or substituted by phenyl or cycloalkyl, and in which one or more $CH_2$ groups is optionally replaced by O, S, NH, a bond, or N-alkyl or N-phenyl;

R1 is phenyl, unsubstituted or substituted, alkyl, cycloalkyl, or a mono- or bicyclic heterocycle, R2 is phenyl, unsubstituted or substituted,
or
R2 is alkyl, cycloalkyl, 2- or 3-furyl, or N-mono- or -bis-alkyl; and 13) a compound of the formula XIII, an isomer thereof, or a physiologically acceptable salt of any of the foregoing:

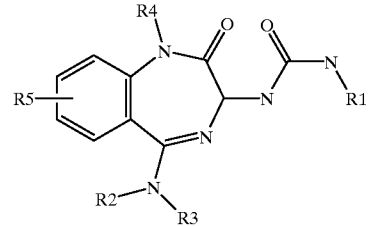

(XIII)

where
R1 is unsubstituted or substituted phenyl,
or
R1 is alkyl, cycloalkyl, a mono- or bicyclic heterocycle, or indanyl, R2 and R3 are the same or different and each is alkyl, which is unsubstituted or substituted by phenyl,
or
R2 and R3 are cycloalkyl
or
R2 and R3 together are an azacycle, R4 is alkyl, unsubstituted or substituted by phenyl,
or R4 is phenyl or fluoroalkyl,
R5 is H or alkyl; and 14) a compound of the formula XIV, an isomer thereof, or a physiologically acceptable salt of any of the foregoing:

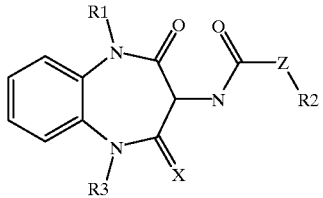

(XIV)

where
X is O or H2,
R1 is alkyl, cycloalkyl, fluoroalkyl, or oxo-substituted alkyl,
Z is unsubstituted or substituted alkyl,
or
Z is alkenyl, cycloalkyl, cycloalkenyl, or a bond,
R2 is unsubstituted or substituted phenyl,
or
R2 is cycloalkyl, unsubstituted or substituted,
R3 is alkyl, cycloalkyl, fluoroalkyl, or oxo-substituted; and 15) a compound of the formula XV, an isomer thereof, or a physiologically acceptable salt of any of the foregoing:

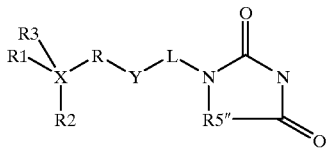

(XV)

where
X is a saturated or unsaturated 5-, 6-, or 7-membered heterocycle or carbocycle,
R is a bond, a heteroatom, carbonyl, a heterocyclic ring, a carbocyclic ring, alkyl, alkenyl, alkoxy, alkylamino, arylalkyl, aryloxy, acyl, acyloxy, or acylamino,
Y is a substituted or unsubstituted, saturated or unsaturated 5-, 6-, or 7-membered heterocyclic or carbocyclic ring, or a bond,
R1, R2 and R3 are the same or different and each is H, Cl, F, Br, NH$_2$, CF$_3$, OH, SO$_3$H, CH$_3$SO$_2$NH, COOH, alkoxy, alkyl, alkoxycarbonyl, hydroxyalkyl, carboxyalkyl, aminoalkyl, acylamino, or acyloxy,
L is alkylamino, alkenylamino, alkylimino, alkenylimino, or acylamino, where the nitrogen is attached to the nitrogen in position 1 of the 4-oxocyclic urea unit,
R4 alkyl, alkenyl, alkynyl, alkylacyl, or heteroalkyl,
A is substituted or unsubstituted, saturated or unsaturated alkyl or heteroalkyl, or a substituted or unsubstituted 5-, 6- or 7-membered heterocycle,
R5 is alkyl; and 16) a compound of the formula XVI, an isomer thereof, or a physiologically acceptable salt of any of the foregoing:

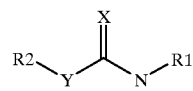

(XVI)

where
X is O, S, NH, NR, C—CN, N—OR, or N—NO$_2$,
Y is a bond, —C=C—, or NH,
R1 is alkyl, alkenyl, alkynyl, aryl, cycloalkyl, a heterocycle, or (heterocyclo)alkyl,
R2 is aryl or a heterocycle; and 17) a compound of the formula XVII, an isomer thereof, or a physiologically acceptable salt of any of the foregoing:

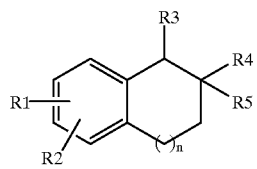

(XVII)

where
R1 is halogen, alkyl, alkenyl, alkynyl, cycloalkyl, aryl, (aryl)alkenyl, alkoxy, O-alkenyl, O-aryl, O-alkyl (heterocyclo), COO-alkyl, alkanoyl, CO-amino, CO-substituted amino, alkyl-CO-amino, alkyl-substituted amino, NHCO-alkyl, NHCO-aryl, NHCO-alkyl(heterocyclo), N(alkyl)CO-alkyl, N(alkyl)CO-aryl, N(alkyl)CO-heterocyclo, or N-(alkyl)CO-alkyl(heterocyclo),
R2 is hydrogen, alkyl, halogen, aryl, alkoxy, amino, or substituted amino,
R3 is oxo, hydroxyl, alkoxy, O—CO-alkyl, O—CO-aryl, O—CO-heterocyclo, NOH, NO-alkyl, N-amino, N-substituted amino, N—NHCONH-alkyl, N—NHSO$_2$-alkyl, N—NHSO$_2$-aryl, amino, substituted amino, NHCO-alkyl, NHCO-aryl, NHCO-heterocyclo, or spiroheterocyclo,
R4 is hydrogen, alkyl, alkyl(CO-alkyl), or alkyl(COO-alkyl),
or
R3 and R4, together with the atom to which they are attached, form a 5- to 7-membered ring optionally containing up to three heteroatoms selected from O, N or S,
R5 is hydrogen, alkyl, alkenyl, alkyl(heterocyclyl), alkyl-NHCO(alkyl), alkyl-NHCO(aryl), or alkyl-NHCO(alkylheterocyclyl),
n is 0, 1, or 2.

5. A method according to claim 1, wherein the KQT1 channel blocker comprises at least one compound selected from:

1) a chromane of the formula I, an isomer thereof, or a physiologically acceptable salt of any of the foregoing:

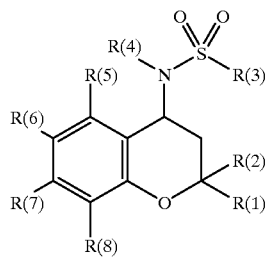

(I)

where

R(1) and R(2) are the same or different and each is hydrogen, $C_pF_{2p+1}$, alkyl having 1, 2, 3, 4, 5, or 6 C atoms, or phenyl,
 where any of the foregoing is unsubstituted or substituted by 1 or 2 substituents selected from F, Cl, Br, I, $CF_3$, methyl, methoxy, sulfamoyl, methylsulfonylamino, and methylsulfonyl,
 p is 1, 2, or 3,
or
R(1) and R(2) together are an alkylene chain having 2, 3, 4, 5, 6, 7, 8, 9, or 10 C atoms,
R(3) is R(9)—$C_nH_{2n}$[NR(11)]$_m$—,
 R(9) is hydrogen or cycloalkyl having 3, 4, 5, 6, 7, or 8 C atoms,
 n is zero, 1, 2, 3, 4, 5, 6, 7, 8, 9, or 10,
 m is zero or 1,
 R(11) is hydrogen or alkyl having 1, 2, 3, 4, 5, or 6 C atoms,
 or
 R(11) together with R(9) is an alkylene group having 1, 2, 3, 4, 5, 6, 7, or 8 C atoms,
 where a $CH_2$ group of the group $C_nH_{2n}$ is optionally replaced by —O—, —$SO_q$, or —NR(10),
 q is zero, 1, or 2,
 R(10) is hydrogen, methyl, or ethyl,
R(4) is R(12)—$C_rH_{2r}$,
 R(12) is hydrogen, cycloalkyl having 3, 4, 5, 6, 7, or 8 C atoms, piperidyl, 1-pyrrolidinyl, N-morpholino, N-methylpiperazino, $C_pF_{2p+1}$, pyridyl, thienyl, imidazolyl, or phenyl,
  where any of the foregoing is unsubstituted or substituted by 1 or 2 substituents selected from F, Cl, Br, I, $CF_3$, methyl, methoxy, sulfamoyl, methylsulfonyl, or methylsulfonylamino,
 r is 1, 2, 3, 4, 5, 6, 7, 8, 9, 10, 11, 12, 13, 14, 15, 16, 17, 18, 19, or 20,
 where a $CH_2$ group of the group $C_rH_{2r}$ is optionally replaced by —O—, —HC=CH—, —C≡C—, —CO—, —CO—O—, —$SO_q$—, or —NR(10)—,
 q is zero, 1, or 2,
 R(10) is hydrogen, methyl, or ethyl,
R(5), R(6), R(7) and R(8) are the same or different and each is hydrogen, F, Cl, Br, I, alkyl having 1, 2, 3, or 4 C atoms, cycloalkyl having 3, 4, 5, 6, 7, or 8 C atoms, —CN, —$CF_3$, —$C_2F_5$, —$C_3F_7$, —$N_3$, —$NO_2$, —CONR(13)R(14), —COOR(15), R(16)—$C_sH_{2s}$—Y—, or phenyl,
 where any of the foregoing is unsubstituted or substituted by 1 or 2 substituents selected from F, Cl, Br, I, $CF_3$, methyl, methoxy, sulfamoyl, and methylsulfonyl,
R(13) and R(14) are the same or different and each is hydrogen or alkyl having 1, 2, or 3 C atoms,
R(15) is hydrogen, methyl, ethyl, phenyl, or —$C_uH_{2u}$—NR(13)R(14), u is 2 or 3,
R(16) is hydrogen, cycloalkyl having 3, 4, 5, 6, 7, or 8 C atoms, —COOR(15), thienyl, imidazolyl, pyridyl, quinolyl, isoquinolyl, piperidyl, 1-pyrrolidinyl, N-morpholino, N-methylpiperazino, $C_tF_{2t+1}$, or phenyl,
 where any of the foregoing is unsubstituted or substituted by 1 or 2 substituents selected from F, Cl, Br, I, $CF_3$, methyl, methoxy, sulfamoyl, or methylsulfonyl,
 s is zero, 1, 2, 3, 4, 5, or 6,
 t is 1, 2, or 3,
Y is $SO_q$, —CO—, —$SO_2$—NR(10)—, —O—, —NR(10)—, or —CO—NR(10),
with the proviso that R(6) is other than —$OCF_3$, or —$OC_2F_5$, and 2) a compound of the formula II, an isomer thereof, or a physiologically acceptable salt of any of the foregoing:

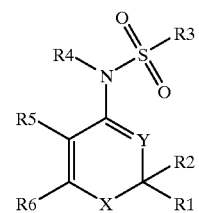

(II)

where

X is —O—, —S—, —SO—, —$SO_2$—, —NR(7)—, —CR(8a)R(8b)—, or —CO—,
R(7) is hydrogen or —($C_aH_{2a}$)—R(9),
 where a $CH_2$ group of the groups $C_aH_{2a}$ is optionally replaced by —O—, —CH=CH—, —C≡C—, —CO—, —CO—O—, —O—CO—, —S—, —SO—, —$SO_2$—, NR(10)—, or —CONR(10)—,
 R(10) is hydrogen or alkyl having 1, 2, or 3 C atoms,
 a is zero, 1, 2, 3, 4, 5, 6, 7, or 8,
 R(9) is hydrogen, $CF_3$, $C_2F_5$, $C_3F_7$, cycloalkyl having 3, 4, 5, 6, 7, or 8 C atoms, dimethylamino, diethylamino, 1-piperidyl, 1-pyrrolidinyl, 4-morpholinyl, 4-methylpiperazin-1-yl, pyridyl, thienyl, imidazolyl, or phenyl,
 where pyridyl, thienyl, imidazolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
or
R(7) and R(1) together form a bond,
R(8a) is hydrogen, $CF_3$, $C_2F_5$, $C_3F_7$, alkyl having 1, 2, 3, 4, 5, or 6 C atoms, or phenyl,
 where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
R(8b) is hydrogen, alkyl having 1, 2, or 3 C atoms, —OR(10), —COOR(10), or CO—R(10),
 where R(10) is hydrogen or alkyl having 1, 2, or 3 C atoms;

or
one of the radicals R(8a) or R(8b) together with R(1) forms a bond,

Y is N or CR(11), R(11) is hydrogen or alkyl having 1, 2, or 3 C atoms

R(1) and R(2) are identical or different and each is hydrogen, $CF_3$, $C_2F_5$, $C_3F_7$, F, Cl, methoxy, alkyl having 1, 2, 3, 4, 5, or 6 C atoms, or phenyl,
where each of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
or
R(1) and R(2) together form an alkylene chain having 2, 3, 4, 5, 6, 7, 8, 9, or 10 C atoms, R(3) is R(12)—$C_nH_{2n}$—NR(13)— or R(12)—$C_nH_{2n}$—,
where one $CH_2$ group in the groups $C_nH_{2n}$ is optionally replaced by —O—, —CO—, —S—, —SO—, —$SO_2$—, or —NR(10a)—,
where R(10a) is hydrogen, methyl, or ethyl,
R(12) is hydrogen, methyl, cycloalkyl having 3, 4, 5, 6, 7, or 8 C atoms, $CF_3$, $C_2F_5$, or $C_3F_7$,
n is zero, 1, 2, 3, 4, 5, 6, 7, 8, 9, or 10,
R(13) is hydrogen or alkyl having 1, 2, 3, 4, 5, or 6 C atoms,
or
R(12) and R(13) together form a bond if n is greater than 3,
or
R(3) and R(4) together form an alkylene chain having 3, 4, 5, 6, 7 or 8 C atoms,
where one $CH_2$ group of the alkylene chain is optionally replaced by —O—, —CO—, —S—, —SO—, —$SO_2$—, or —NR(10a)—,
where R(10a) is hydrogen, methyl, or ethyl, R(4) is R(14)—$C_rH_{2r}$,
where one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(10b)—, or —CONR(10b)—,
where R(10b) is hydrogen or alkyl having 1, 2, or 3 C atoms,
R(14) is methyl, $CF_3$, $C_2F_5$, $C_3F_7$, cycloalkyl having 3, 4, 5, 6, 7, or 8 C atoms, —OH, —COOH, —NR(23)R(24), 1-piperidyl, 1-pyrrolidinyl, 4-morpholinyl, 4-methylpiperazin-1-yl, pyridyl, thienyl, imidazolyl, or phenyl,
where pyridyl, thienyl, imidazolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
R(23) and R(24) are the same or different and each is hydrogen or alkyl having 1, 2, or 3 C atoms,
or
R(23) and R(24) together form a chain of 4 or 5 methylene groups, one $CH_2$ group of which is optionally replaced by —O—, —S—, —NH—, —N($CH_3$)—, or —N(benzyl)—,
r is zero, 1, 2, 3, 4, 5, 6, 7, 8, 9, 10, 11, 12, 13, 14, 15, 16, 17, 18, 19, or 20, R(5) and R(6) together form a group
—CR(15)=CR(16)—CR(17)=CR(18)—,
—CR(15)=CR(16)—CR(17)=N—,
—CR(15)=CR(16)—N=CR(18)—,
—CR(15)=N—CR(17)=N—,
—CR(15)=N—N=CR(18)—,
—N=CR(16)—CR(17)=N—, and
—CR(15)=CR(16)—,
where either end of said group is attached to the ring at the R(5) position,
R(15), R(16), R(17) and R(18) are the same or different and each is hydrogen, F, Cl, Br, I, alkyl having 1, 2, 3, 4, or 5 C atoms, cycloalkyl having 3, 4, 5, 6, 7, or 8 C atoms, —CN, —$CF_3$, —$C_2F_5$, —$C_3F_7$, —$N_3$, —$NO_2$, —Z—$C_sH_{2s}$—R(22), thienyl, or phenyl,
wherein each of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;
Z is —O—, —CO—, —CO—O—, —O—CO—, —S—, —SO—, —$SO_2$—, —$SO_2$—O—, —$SO_2$NR(10c), —NR(10c)—, or —CONR(10c)—,
where R(10c) is hydrogen or alkyl having 1, 2 or 3 C atoms;
s is zero, 1, 2, 3, 4, 5, or 6,
R(22) is hydrogen, $CF_3$, $C_2F_5$, $C_3F_7$, cycloalkyl having 3, 4, 5, 6, 7, or 8 C atoms, —NR(19)R(20), —COOR(21), 1-piperidyl, 1-pyrrolidinyl, 4-morpholinyl, 4-methylpiperazin-1-yl, pyridyl, thienyl, imidazolyl, quinolyl, isoquinolyl, or phenyl,
where pyridyl, thienyl, imidazolyl, quinolyl, isoquinolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
R(19) and R(20) are the same or different and each is hydrogen or alkyl having 1, 2, or 3 C atoms,
or
R(19) and R(20) together form a chain of 4 or 5 methylene groups, one $CH_2$ group of which is optionally replaced by —O—, —S—, —NH—, —N($CH_3$)—, or —N(benzyl)—,
R(21) is hydrogen or alkyl having 1, 2, or 3 C atoms, with the proviso that Y is other than CR(11) when X is O; and 3) a compound of the formula III, an isomer thereof, or a physiologically acceptable salt of any of the foregoing:

(III)

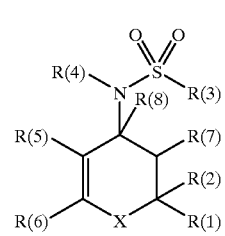

in which:

X is —[S(O)$_{zero, 1 \text{ or } 2}$]—, —NR(9)—, —[CR(9)R(23)]—, or —CO—,

R(9) is hydrogen or —(C$_n$H$_{2n}$)—R(10), n is zero, 1, 2, 3, 4, 5, 6, 7 or 8, R(10) is hydrogen, cycloalkyl having 3, 4, 5, 6, 7, or 8 C atoms, piperidyl, 1-pyrrolidinyl, N-morpholino, N-methylpiperazino, CF$_3$, C$_2$F$_5$ or C$_3$F$_7$, where one CH$_2$ group of the group C$_n$H$_{2n}$ is optionally replaced by —O—, —CH=CH—, —C≡C—, —CO—, —CO—O—, —[SO$_{zero, 1 \text{ or } 2}$]—, or —NR(11)—, R(11) is hydrogen, methyl, or ethyl, or R(10) is pyridyl, thienyl, imidazolyl, or phenyl, which are unsubstituted or substituted by 1 or 2 substituents selected from F, Cl, Br, I, CF$_3$, methyl, methoxy, sulfamoyl, methylsulfonyl, and methylsulfonylamino, or R(9) together with R(1) forms a bond;

R(23) is hydrogen, alkyl having 1, 2, or 3 C atoms, OH, O-alkyl having 1, 2, or 3 C atoms, COOH, COO-alkyl having 1, 2, or 3 C atoms, or —CO—R(24);

R(24) is hydrogen, methyl, or ethyl,

R(1) and R(2) are the same or different and each is hydrogen, CF$_3$, C$_2$F$_5$, C$_3$F$_7$, alkyl having 1, 2, 3, 4, 5, or 6 C atoms, or phenyl, where any of the foregoing is unsubstituted or substituted by 1 or 2 substituents selected from F, Cl, Br, I, CF$_3$, methyl, methoxy, sulfamoyl and methylsulfonyl, or R(1) and R(2) together are an alkylene chain having 2, 3, 4, 5, 6, 7, 8, 9, or 10 C atoms, R(3) is R(12)—C$_a$H$_{2a}$[NR(13)]$_m$—, R(12) is hydrogen or cycloalkyl having 3, 4, 5, 6, 7, or 8 C atoms, CF$_3$, C$_2$F$_5$, or C$_3$F$_7$, a is zero, 1, 2, 3, 4, 5, 6, 7, 8, 9, or 10, m is zero or 1, R(13) is hydrogen or alkyl having 1, 2, 3, 4, 5, or 6 C atoms, or R(12) and R(13) together are an alkylene group having 4, 5, 6, 7, or 8 C atoms where one CH$_2$ group of the alkylene group is optionally replaced by —O—, —[SO$_{zero, 1 \text{ or } 2}$]—, —CO—, or —NR(11)—, where R(11) is hydrogen, methyl, or ethyl, R(4) is R(14)—C$_r$H$_{2r}$, r is 1, 2, 3, 4, 5, 6, 7, 8, 9, 10, 11, 12, 13, 14, 15, 16, 17, 18, 19, or 20;

R(14) is hydrogen, cycloalkyl having 3, 4, 5, 6, 7, or 8 C atoms, piperidyl, 1-pyrrolidinyl, N-morpholino, N-methylpiperazino, CF$_3$, C$_2$F$_5$, C$_3$F$_7$, pyridyl, thienyl, imidazolyl, or phenyl, which is unsubstituted or substituted by 1 or 2 substituents selected from F, Cl, Br, I, CF$_3$, methyl, methoxy, sulfamoyl, methylsulfonyl, and methylsulfonylamino, where one CH$_2$ group of the group C$_r$H$_{2r}$ is optionally replaced by —O—, —CH=CH—, —C≡C—, —CO—, —CO—O—, —CO—NR(11)—, —[SO$_{zero, 1 \text{ or } 2}$]—, or —NR(11)—;

or

R(3) and R(4) together form an alkylene chain having 3, 4, 5, 6, 7, or 8 C atoms, where one CH$_2$ group of the alkylene chain is optionally replaced by —O—, —[SO$_{zero, 1 \text{ or } 2}$]—, —CO—, or —NR(11)—, R(5) and R(6) together are —CR(15)=CR(16)—CR(17)=CR(18)—, —CR(15)=CR(16)—CR(17)=N—, —CR(15)=CR(16)—N=CR(18)—, —CR(15)=N—CR(17)=N—, —CR(15)=N—N=CR(18)—, —N=CR(16)—CR(17)=N—, or —S—CR(15)=CR(16)—, R(15), R(16), R(17) and R(18)

are the same or different and each is hydrogen, F, Cl, Br, I, alkyl having 1, 2, 3, or 4 C atoms, cycloalkyl having 3, 4, 5, 6, 7, or 8 C atoms, CN, CF$_3$, C$_2$F$_5$, C$_3$F$_7$, N$_3$, NO$_2$, —CONR(19)R(20), —COOR(21), R(22)—C$_s$H$_{2s}$—Z—, or phenyl, where any of the foregoing is unsubstituted or substituted by 1 or 2 substituents selected from F, Cl, Br, I, CF$_3$, methyl, methoxy, sulfamoyl, and methylsulfonyl, R(19) and R(20) are the same or different and each is hydrogen or alkyl having 1, 2, or 3 C atoms, R(21) is hydrogen, methyl, ethyl, phenyl, or —C$_u$H$_{2u}$—NR(19)R(20), u is 2 or 3, where the phenyl is unsubstituted or substituted by 1 or 2 substituents selected from F, Cl, Br, I, CF$_3$, methyl, methoxy, sulfamoyl, or methylsulfonyl, R(22) is hydrogen, cycloalkyl having 3, 4, 5, 6, 7, or 8 C atoms, —COOR(21), thienyl, imidazolyl, pyridyl, quinolyl, isoquinolyl, piperidyl, 1-pyrrolidinyl, N-morpholino, N-methylpiperazino, CF$_3$, C$_2$F$_5$, C$_3$F$_7$, or phenyl, where any of the foregoing is unsubstituted or substituted by 1 or 2 substituents selected from F, Cl, Br, I, CF$_3$, methyl, methoxy, sulfamoyl or methylsulfonyl, s is zero, 1, 2, 3, 4, 5, or 6, Z is —[S(O)$_{zero, 1 \text{ or } 2}$]—, —CO—, —SO$_2$—NR(11)—, —SO$_2$—O—, —O—, —NR(11)—, or —[CO—NR(11)]—, R(7) is hydrogen, hydroxyl, alkoxy having 1, 2, 3, or 4 C atoms, acyloxy having 1, 2, 3, or 4 C atoms, Cl, Br, F, alkyl having 1, 2, 3, or 4 C atoms, R(8) is hydrogen or alkyl having 1, 2, 3, 4, 5, or 6 C atoms; and 4) a chromane derivative of the formula IV, an isomer thereof, or a physiologically acceptable salt thereof:

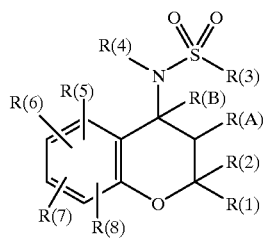

(IV)

where

R(1) and R(2) are the same or different and each is hydrogen, CF$_3$, C$_2$F$_5$, C$_3$F$_7$, alkyl having 1, 2, 3, 4, 5, or 6 C atoms, or phenyl, where any of the foregoing is unsubstituted or substituted by 1 or 2 substituents selected from F, Cl, Br, I, $CF_3$, methyl, methoxy, sulfamoyl, and methylsulfonyl, or R(1) and R(2) together form an alkylene chain having 2, 3, 4, 5, 6, 7, 8, 9, or 10 C atoms, R(A) is hydroxyl, alkanoyloxy having 1, 2, 3, 4, 5, or 6 C atoms, or alkylsulfonyloxy having 1, 2, 3, 4, 5, or 6 C atoms, R(B) is hydrogen, or R(A) and R(B) together form a bond;

R(3) is R(9)—$C_nH_{2n}$[NR(11)]$_m$—,

R(9) is hydrogen or cycloalkyl having 3, 4, 5, 6, 7, or 8 C atoms, n is zero, 1, 2, 3, 4, 5, 6, 7, 8, 9, or 10, m is zero or 1, R(11) is hydrogen or alkyl having 1, 2, 3, 4, 5, or 6 C atoms, or R(11) and R(9) together form an alkylene group having 1, 2, 3, 4, 5, 6, 7, or 8 C atoms, where one $CH_2$ group of the group $C_nH_{2n}$ is optionally replaced by —O—, $SO_{zero, 1 \text{ or } 2}$— or —NR(10), R(10) is hydrogen, methyl, or ethyl, R(4) is R(12)—$C_rH_{2r}$, R(12) is hydrogen, cycloalkyl having 3, 4, 5, 6, 7, or 8 C atoms, piperidyl, 1-pyrrolidinyl, N-morpholino, N-methylpiperazino, $CF_3$, $C_2F_5$, $C_3F_7$, pyridyl, thienyl, imidazolyl or phenyl, where pyridyl, thienyl, imidazolyl, or phenyl are unsubstituted or substituted by 1 or 2 substituents selected from F, Cl, Br, I, $CF_3$, methyl, methoxy, sulfamoyl, methylsulfonyl, and methylsulfonylamino, r is zero, 1, 2, 3, 4, 5, 6, 7, 8, 9, 10, 11, 12, 13, 14, 15, 16, 17, 18, 19, or 20, where one $CH_2$ group of the group $C_rH_{2r}$ is optionally replaced by —O—, >CH=CH<, —C≡C—, —CO—, —CO—O—, $SO_{zero, 1 \text{ or } 2}$— or —NR(10)—, R(5), R(6), R(7) and R(8) are the same or different and each is hydrogen, F, Cl, Br, I, alkyl having 1, 2, 3, 4, 5 or 6 C atoms, cycloalkyl having 3, 4, 5, 6, 7 or 8 C atoms, —CN, —$CF_3$, —$C_2F_5$, —$C_3F_7$, —$N_3$, —$NO_2$, —CONR(13)R(14), —COOR(15), R(16)—$C_sH_{2s}$—Y—, or phenyl, where any of the foregoing is unsubstituted or substituted by 1 or 2 substituents selected from F, Cl, Br, I, $CF_3$, methyl, methoxy, sulfamoyl, and methylsulfonyl, R(13) and R(14) are the same or different and each is hydrogen or alkyl having 1, 2, or 3 C atoms, R(15) is hydrogen, methyl, ethyl, phenyl, or —$C_uH_{2u}$—NR(13)R(14), u is 2 or 3, R(16) is hydrogen, cycloalkyl having 3, 4, 5, 6, 7, or 8 C atoms, —COOR(15), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl, where any of the foregoing is unsubstituted or substituted by 1 or 2 substituents selected from F, Cl, Br, I, $CF_3$, methyl, methoxy, sulfamoyl, and methylsulfonyl, s is zero, 1, 2, 3, 4, 5, or 6, Y —S—, —SO—, —$SO_2$—, —CO—, —$SO_2$—NR(10)—, —O—, —NR(10)—, or —CO—NR(10), but with the proviso that two of the substituents R(5), R(6), R(7) and R(8) are other than hydrogen; and 5) a compound of the formula V, an isomer thereof, or a physiologically acceptable salt thereof:

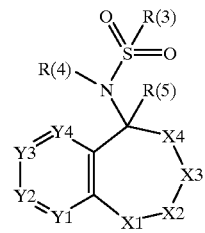

(V)

where

X1 is —O—, —S—, —SO—, —$SO_2$—, —CR(1)R(2)—, —NR(6)—, —CO—, or —CR(1)R(7)—,

R(1) and R(2) are the same or different and each is hydrogen, $CF_3$, $C_2F_5$, $C_3F_7$, alkyl having 1, 2, 3, 4, 5 or 6 C atoms, or phenyl, where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(1) and R(2) together form an alkylene chain having 2, 3, 4, 5, 6, 7, 8, 9, or 10 C atoms, R(6) is hydrogen or —$C_nH_{2n}$—R(8), where one $CH_2$ group of the group $C_nH_{2n}$ is optionally replaced by —O—, —CH=CH—, —C≡C—, —CO—, —CO—O—, —O—CO—, —S—, —SO—, —$SO_2$—, —NR(9)—, or —CONR(9)—, R(9) is hydrogen or alkyl having 1, 2, or 3 C atoms, n is zero, 1, 2, 3, 4, 5, 6, 7, or 8, R(8) is hydrogen, $CF_3$, $C_2F_5$, $C_3F_7$, cycloalkyl having 3, 4, 5, 6, 7, or 8 C atoms, dimethylamino, diethylamino, 1-piperidyl, 1-pyrrolidinyl, 4-morpholinyl, 4-methylpiperazin-1-yl, pyridyl, thienyl, imidazolyl, or phenyl, where pyridyl, thienyl, imidazolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;

X2 is —CR(1)R(2)— or —CR(2)R(10)—, or

X2 is —O—, —S—, —SO—, —$SO_2$— or —NR(6)—, where the radicals R(1), R(2), and R(6) are as defined under X1, and the radicals R(1), R(2), and R(6) in X2 are the same or different as X1;

R(10) together with R(7) form a bond,

X3 is —CR(1)R(2)—, or

X3 is also —O—, —S—, —SO—, —$SO_2$—, or —NR(6)—, where the radicals R(1), R(2), and R(6) are as defined under X1, and the radicals R(1), R(2), and R(6) in X2 are the same or different as X1;

X4 is —CR(1)R(2)—, —NR(6)—, —NR(11)—, —CH(OR(30))—, or —CR(2)R(11)—,
  where the radicals R(1), R(2), and R(6) are as defined under X1, and the radicals R(1), R(2), and R(6) in X2 are the same or different as X1;
  R(30) is hydrogen, alkyl having 1, 2, or 3 C atoms, or acyl having 1, 2, 3, or 4 C atoms,
  R(11) together with R(5) forms a bond,
Y1, Y2, Y3, and Y4 are the same or different and each is —CR(12)— or N,
  where at most 2 of the groups Y1, Y2, Y3 and Y4 are optionally simultaneously N,
  the radicals R(12) are the same or different and each is hydrogen, F, Cl, Br, I, alkyl having 1, 2, 3, 4, or 5 C atoms, cycloalkyl having 3, 4, 5, 6, 7, or 8 C atoms, CN, $CF_3$, $C_2F_5$, $C_3F_7$, $N_3$, $NO_2$, —Z—$C_mH_{2m}$—R(13), or phenyl,
    which is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl and methylsulfonylamino;
  Z is —O—, —CO—, —CO—O—, —O—CO—, —S—, —SO—, —$SO_2$—, —$SO_2$NR(14)—, —NR(14)— or —CONR(14)—, R(14) is hydrogen or alkyl having 1, 2, or 3 C atoms;
  m is zero, 1, 2, 3, 4, 5, or 6,
  R(13) is hydrogen, $CF_3$, $C_2F_5$, $C_3F_7$, cycloalkyl having 3, 4, 5, 6, 7 or 8 C atoms, —NR(15)R(16), —CONR(15)R(16), —OR(30a), phenyl, thienyl or an N-containing heterocycle having 1, 2, 3, 4, 5, 6, 7, 8 or 9 C atoms,
    where phenyl, thienyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl and methylsulfonylamino,
    R(15) and R(16) are the same or different and each is hydrogen or alkyl having 1, 2 or 3 C atoms,
    or
    R(15) and R(16) together are a chain of 4 or 5 methylene groups, one $CH_2$ group of which is optionally replaced by —O—, —S—, —NH—, —N($CH_3$)— or —N(benzyl)—,
    R(30a) is hydrogen, alkyl having 1, 2, or 3 C atoms or acyl having 1, 2, 3, or 4 C atoms,
or
Y1 and Y2 together are an S atom and Y3 and Y4 are each —CR(12)—,
  the radicals R(12) are the same or different and each is as defined under Y1, Y2, Y3, Y4,
R(3) is R(17)—$C_xH_{2x}$—NR(18)— or R(17)—$C_xH_{2x}$—,
  where one $CH_2$ group in the groups $C_xH_{2x}$ is optionally replaced by —O—, —CO—, —S—, —SO—, —$SO_2$— or —NR(19)—,
  R(19) is hydrogen, methyl or ethyl,
  R(17) is hydrogen, methyl, cycloalkyl having 3, 4, 5, 6, 7 or 8 C atoms, $CF_3$, $C_2F_5$ or $C_3F_7$,
  x is zero, 1, 2, 3, 4, 5, 6, 7, 8, 9 or 10,
  R(18) is hydrogen or alkyl having 1, 2, 3, 4, 5, 6, 7 or 8 C atoms,
  or
  R(18) and R(17) together form a bond if x is 3 or greater,
or
R(3) is phenyl,
  which is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
or
R(3) together with R(4) form an alkylene chain having 3, 4, 5, 6, 7, or 8 C atoms,
  where one $CH_2$ group of the alkylene chain is optionally replaced by —O—, —CO—, —S—, —SO, or $SO_2$,
R(4) is —$C_rH_{2r}$—R(20),
  where one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(21)—, or —CONR(21)—,
  R(21) is hydrogen or alkyl having 1, 2, or 3 C atoms;
  r is zero, 1, 2, 3, 4, 5, 6, 7, 8, 9, 10, 11, 12, 13, 14, 15, 16, 17, 18, 19, or 20,
  R(20) is hydrogen, methyl, $CF_3$, $C_2F_5$, $C_3F_7$, cycloalkyl having 3, 4, 5, 6, 7, or 8 C atoms, —NR(22)R(23), phenyl, thienyl, or an N-containing heterocycle having 1, 2, 3, 4, 5, 6, 7, 8, or 9 C atoms,
    where phenyl, thienyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
    R(22) and R(23) are the same or different and each is hydrogen or alkyl having 1, 2, or 3 C atoms,
    or
    R(22) and R(23) together form a chain of 4 or 5 methylene groups one $CH_2$ group of which is optionally replaced by —O—, —S—, —NH—, —N($CH_3$)—, or —N(benzyl)—,
  R(5) is hydrogen or together with R(11) forms a bond; and
6) a compound of the formula VI, an isomer thereof, or a physiologically acceptable salt thereof, (VI)

where
R(1) and R(2) are the same or different and each is a hydrogen, $CF_3$, $C_2F_5$, $C_3F_7$, alkyl having 1, 2, 3, 4, 5, or 6 C atoms, or phenyl,
  where any of the foregoing is unsubstituted or substituted by 1 or 2 substituents selected from F, Cl, Br, I, $CF_3$, methyl, methoxy, sulfamoyl, and methylsulfonyl,
or
R(1) and R(2) together are an alkylene chain having 2, 3, 4, 5, 6, 7, 8, 9, or 10 C atoms, where one CH$_2$ group of the alkylene chain is optionally replaced by —O—, —CO—, —S—, —SO—, —SO$_2$—, or —NR(10)—, R(10) is hydrogen or alkyl having 1, 2, or 3 C atoms, R(3) is R(12)—C$_a$H$_{2a}$[NR(13)]$_m$—,
  R(12) is hydrogen or cycloalkyl having 3, 4, 5, 6, 7, or 8 C atoms, CF$_3$, C$_2$F$_5$, or C$_3$F$_7$,
  a is zero, 1, 2, 3, 4, 5, 6, 7, 8, 9, or 10,
  m is zero or 1,
  R(13) is hydrogen or alkyl having 1, 2, 3, 4, 5, or 6 C atoms,
or
  R(12) and R(13) together form an alkylene group having 4, 5, 6, 7 or 8 C atoms,
    where one CH$_2$ group of the alkylene group is optionally replaced by —O—, —[SO$_{zero, 1 \text{ or } 2}$]—, —CO— or —NR(10)—;
    R(10) is hydrogen or alkyl having 1, 2 or 3 C atoms;
R(4) R(14)—C$_r$H$_{2r}$,
  r is zero, 1, 2, 3, 4, 5, 6, 7, 8, 9, 10, 11, 12, 13, 14, 15, 16, 17, 18, 19, or 20,
  R(14) is hydrogen, cycloalkyl having 3, 4, 5, 6, 7, or 8 C atoms, piperidyl, 1-pyrrolidinyl, N-morpholino, N-methylpiperazino, CF$_3$, C$_2$F$_5$, C$_3$F$_7$, pyridyl, thienyl, imidazolyl, or phenyl,
    where any of the foregoing is unsubstituted or substituted by 1 or 2 substituents selected from F, Cl, Br, I, CF$_3$, methyl, methoxy, sulfamoyl, methylsulfonyl and methylsulfonylamino,
  where one CH$_2$ group of the group C$_r$H$_{2r}$ is optionally replaced by —O—, —CH=CH—, —C☐C—, —CO—, —CO—O—, —CO—NR(11)—, —[SO$_{zero, 1 \text{ or } 2}$]— or —NR(11)—,
  R(11) is hydrogen or —(C$_a$H$_{2a}$)—R(10),
    where one CH$_2$ group of the group C$_a$H$_{2a}$ is optionally replaced by —O—, —CH=CH—, —C≡C—, —CO—, —CO—O—, —O—CO—, —S—, —SO—, —SO$_2$—, NR(10)—, or —CONR(10)—, R(10) is hydrogen or alkyl having 1, 2, or 3 C atoms,
or
R(3) and R(4) together are an alkylene chain having 3, 4, 5, 6, 7, or 8 C atoms,
  where one CH$_2$ group of the alkylene chain is optionally replaced by —O—, —[SO$_{zero, 1 \text{ or } 2}$]—, —CO—, or —NR(11)—,
  R(11) is hydrogen or —(C$_a$H$_{2a}$)—R(10),
    where one CH$_2$ group of the group C$_a$H$_{2a}$ is optionally replaced by —O—, —CH=CH—, —C≡C—, —CO—, —CO—O—, —O—CO—, —S—, —SO—, —SO$_2$—, NR(10)—, or —CONR(10)—,
    R(10) is hydrogen or alkyl having 1, 2 or 3 C atoms,
R(5) and R(6) are
  —CR(15)=CR(16)—CR(17)=N—,
  —CR(15)=CR(16)—N=CR(17)—,
  —CR(15)=N—CR(17)=N—,
  —CR(15)=N—N=CR(17)—,
  —N=CR(16)—CR(17)=N—, or
  —S—CR(15)=CR(16)—;
R(15), R(16) and R(17) are the same or different and each is hydrogen, F, Cl, Br, I, alkyl having 1, 2, 3, or 4 C atoms, cycloalkyl having 3, 4, 5, 6, 7, or 8 C atoms, CN, CF$_3$, C$_2$F$_5$, C$_3$F$_7$, N$_3$, NO$_2$, —CONR(19)R(21), —COOR(21), R(22)—C$_s$H$_{2s}$—Z—, or phenyl, where any of the foregoing is unsubstituted or substituted by 1 or 2 substituents selected from F, Cl, Br, I, CF$_3$, methyl, methoxy, sulfamoyl and methylsulfonyl,
R(19) is hydrogen or alkyl having 1, 2, or 3 C atoms,
R(21) is hydrogen, methyl, ethyl, phenyl, or —C$_u$H$_{2u}$—NR(19)R(20),
  where the phenyl is unsubstituted or substituted by 1 or 2 substituents selected from F, Cl, Br, I, CF$_3$, methyl, methoxy, sulfamoyl and methylsulfonyl,
  R(20) is hydrogen or alkyl having 1, 2, or 3 C atoms,
  u is 2 or 3,
R(22) is hydrogen, cycloalkyl having 3, 4, 5, 6, 7, or 8 C atoms, —COOR(21), CONR(19)R(21), thienyl, imidazolyl, pyridyl, quinolyl, isoquinolyl, piperidyl, 1-pyrrolidinyl, N-morpholino, N-methylpiperazino, CF$_3$, C$_2$F$_5$, C$_3$F$_7$, or phenyl,
  where any of the foregoing is unsubstituted or substituted by 1 or 2 substituents selected from F, Cl, Br, I, CF$_3$, methyl, methoxy, sulfamoyl, and methylsulfonyl,
s is zero, 1, 2, 3, 4, 5, or 6,
Z is —[S(O)$_{zero, 1 \text{ or } 2}$]—, —CO—, —SO$_{(0, 1 \text{ or } 2)}$—NR(11)—, —SO$_2$—O—, —O—, —NR(11)—, or —[CO—NR(11)]—,
R(7) is hydrogen, hydroxyl, alkoxy having 1, 2, 3, or 4 C atoms, acyloxy having 1, 2, 3, or 4 C atoms, Cl, Br, F, alkyl having 1, 2, 3, or 4 C atoms,
R(8) is hydrogen or alkyl having 1, 2, 3, 4, 5, or 6 C atoms; and 7) a compound of the formula VII, an isomer thereof, or a physiologically acceptable salt of any of the foregoing:

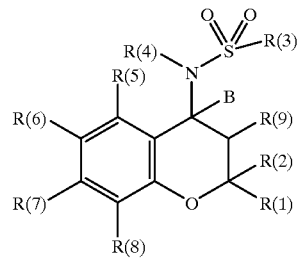

(VII)

where
R(1) and R(2) are the same or different and each is hydrogen, CF$_3$, C$_2$F$_5$, C$_3$F$_7$, alkyl having 1, 2, 3, 4, 5, or 6 C atoms, or phenyl,
  which is unsubstituted or substituted by 1 or 2 substituents selected from F, Cl, Br, I, CF$_3$, NO$_2$, CN, NH$_2$, OH, methyl, ethyl, methoxy, dimethylamino, sulfamoyl, methylsulfonyl, and methylsulfonylamino,
or
R(1) and R(2) together form an alkylene chain having 2, 3, 4, 5, 6, 7, 8, 9, or 10 C atoms,
R(3) is R(10)—C$_n$H$_{2n}$—NR(11)— or R(10)—C$_n$H$_{2n}$—,
  where one CH$_2$ group in the groups C$_n$H$_{2n}$ is optionally replaced by —O—, —CO—, —S—, —SO—, —SO$_2$—, or —NR(12a)—, R(12a) is hydrogen, methyl, or ethyl,
R(10) is hydrogen, methyl, cycloalkyl having 3, 4, 5, 6, 7, or 8 C atoms, $CF_3$, $C_2F_5$ or $C_3F_7$,
n is zero, 1, 2, 3, 4, 5, 6, 7, 8, 9, or 10,
R(11) is hydrogen or alkyl having 1, 2, 3, 4, 5, or 6 C atoms,
or
R(10) and R(11) together form a bond if n is 3 or greater,
R(4) is R(13)—$C_rH_{2r}$—Z—$C_qH_{2q}$—,
q is 0, 1, 2, 3, 4, 5, 6, 7, or 8,
r is 0, 1, 2, 3, 4, 5, 6, 7, or 8,
Z is —CO—NR(14)—,
—OCO—NR(14)—,
—O—$C_xH_{2x}$—O—,
—O—$C_xH_{2x}$—NR(14)—,
—O—$C_xH_{2x}$—CO—O,
—CO—O—$C_xH_{2x}$—O— or
—CO—O—$C_xH_{2x}$—NR(14)—,
where in each case either end of the groups defined by Z is attached to $C_qH_{2q}$—;
x is 2, 3, or 4,
R(14) is hydrogen, alkyl having 1, 2, or 3 C atoms, —$C_yH_{2y}$—OR(12b), —$C_yH_{2y}$—NR(12b)$_2$,
R(12b) is hydrogen, methyl or ethyl,
y is 2 or 3,
R(13) is H, $CF_3$, $C_2F_5$, $C_3F_7$, cycloalkyl having 3, 4, 5, 6, 7, or 8 C atoms, —NR(15)R(16), —CONR(15)R(16), —C(=NR(17))NR(15)R(16), —OR(17), —COOR(17), phenyl, or an N-containing heterocycle having 1, 2, 3, 4, 5, 6, 7, 8, or 9 C atoms,
where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, aminosulfonyl, and methylsulfonylamino,
R(15) and R(16) are the same or different, and each is hydrogen, alkyl having 1, 2, 3, or 4 C atoms, or —$C_zH_{2z}$-phenyl,
where phenyl is unsubstituted or substituted by 1 or 2 substituents selected from F, Cl, Br, $CF_3$, $NO_2$, CN, OH, methyl, ethyl, methoxy, dimethylamino, sulfamoyl, methylsulfonyl, aminosulfonyl, and methylsulfonylamino;
or
R(15) and R(16) together are a chain of 4 or 5 methylene groups, one $CH_2$ group of which is optionally replaced by —O—, —S—, —NH—, —N($CH_3$)— or —N(benzyl)—,
R(17) is hydrogen or alkyl having 1, 2, or 3 C atoms,
R(5), R(6), R(7) and R(8) are the same or different and each is hydrogen, F, Cl, Br, I, alkyl having 1, 2, 3, 4, or 5 C atoms, cycloalkyl having 3, 4, 5, 6, 7, or 8 C atoms, —CN, —$CF_3$, —$C_2F_5$, —$C_3F_7$, —$N_3$, —$NO_2$, —Y—$C_sH_{2s}$—R(18), or phenyl,
where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
Y is —O—, —CO—, —CO—O—, —O—CO—, —S—, —SO—, —$SO_2$—, —$SO_2$—O—, —$SO_2$NR(10c), —NR(10c)—, or —CONR(10c)—, R(10c) is hydrogen or alkyl having 1, 2, or 3 C atoms,
s is zero, 1, 2, 3, 4, 5, or 6;
R(18) is hydrogen, $CF_3$, $C_2F_5$, $C_3F_7$, cycloalkyl having 3, 4, 5, 6, 7, or 8 C atoms, —COOR(21), 1-piperidyl, 1-pyrrolidinyl, 4-morpholinyl, 4-methylpiperazin-1-yl, pyridyl, thienyl, imidazolyl, quinolyl, isoquinolyl, or phenyl,
where pyridyl, thienyl, imidazolyl, quinolyl, isoquinolyl and phenyl are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
R(21) is hydrogen or alkyl having 1, 2, or 3 C atoms,
R(9) is hydrogen, OR(10d), or OCOR(10d),
R(10d) is hydrogen or alkyl having 1, 2, or 3 C atoms,
B is hydrogen,
or
R(9) and B together form a bond, and
8) a compound of the formula VIII, an isomer thereof, or a physiologically acceptable salt thereof:

(VIII)

[Chemical structure showing chroman with R(4)-N(R(5))-S(=O)(=O)-R(3) at position 4, R(9) and B at position 4, R(2) at position 3, R(1) at position 2, and R(6), R(7), R(8) on the benzene ring]

where
R(1) and R(2) are the same or different and each is hydrogen, $CF_3$, $C_2F_5$, $C_3F_7$, alkyl having 1, 2, 3, 4, 5, or 6 C atoms, or phenyl,
where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
or
R(1) and R(2) together form an alkylene chain having 2, 3, 4, 5, 6, 7, 8, 9, or 10 C atoms,
R(3) is R(10)—$C_nH_{2n}$—NR(11)— or R(10)—$C_nH_{2n}$—,
where one $CH_2$ group in the groups $C_nH_{2n}$ is optionally replaced by —O—, —CO—, —S—, —SO—, —$SO_2$—, or —NR(12a)—,
R(12a) is hydrogen, methyl, or ethyl,
R(10) is hydrogen, methyl, cycloalkyl having 3, 4, 5, 6, 7, or 8 C atoms, $CF_3$, $C_2F_5$, or $C_3F_7$,
n is zero, 1, 2, 3, 4, 5, 6, 7, 8, 9, or 10,
R(11) is hydrogen or alkyl having 1, 2, 3, 4, 5, or 6 C atoms,
or
R(10) and R(11) together form a bond if n is 3 or greater,
or
R(3) together with R(4) is an alkylene chain having 3, 4, 5, 6, 7 or 8 C atoms,
where one $CH_2$ group of the alkylene chain is optionally replaced by —O—, —CO—, —S—, —SO—, —$SO_2$—, or —NR(12a)—, R(12a) is hydrogen, methyl or ethyl, R(4) is R(13)—$C_rH_{2r}$, where one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(14)—, or —CONR(14)—, R(14) is hydrogen, alkyl having 1, 2, or 3 C atoms, —$C_yH_{2y}$—OR(12b), or —$C_yH_{2y}$—NR(12b)$_2$, R(12b) is hydrogen, methyl, or ethyl, y is 2 or 3, R(13) is H, $CF_3$, $C_2F_5$, $C_3F_7$, cycloalkyl having 3, 4, 5, 6, 7, or 8 C atoms, —NR(15)R(16), —CONR(15)R(16), —OR(17), —COOR(17), phenyl, or an N-containing heterocycle having 1, 2, 3, 4, 5, 6, 7, 8, or 9 C atoms, where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(15) and R(16) are the same or different and each is hydrogen or alkyl having 1, 2, 3, or 4 C atoms, or R(15) and R(16) together form a chain of 4 or 5 methylene groups, one $CH_2$ group of which is optionally replaced by —O—, —S—, —NH—, —N($CH_3$)—, or —N(benzyl)—, R(17) is hydrogen, alkyl having 1, 2, or 3 C atoms, —$C_xH_{2x}$OR(12c), R(12c) is hydrogen, methyl, or ethyl, x is 2 or 3, r is zero, 1, 2, 3, 4, 5, 6, 7, 8, 9, 10, 11, 12, 13, 14, 15, 16, 17, 18, 19, or 20, at least one of the substituents R(5), R(6), R(7), and R(8) is —Y—$C_sH_{2s}$—R(18), thienyl, furyl or an N-containing heterocycle having 1, 2, 3, 4, 5, 6, 7, 8 or 9 C atoms, where thienyl, furyl, and the N-containing heterocycle are unsubstituted or substituted by 1 or 2 substituents selected from F, Cl, Br, I, $CF_3$, $NO_2$, CN, $NH_2$, OH, methyl, ethyl, methoxy, methylamino, dimethylamino, ethylamino, diethylamino, sulfamoyl, methylsulfonyl, and methylsulfonylamino, Y is —O—, —CO—, —O—CO—, —S—, —SO—, —$SO_2$—, —$SO_2$—O—, —$SO_2$NR(12d)—, —NR(12d)—, or —CONR(12d)—, where the attachment to the benzene ring is in each case effected through the atom depicted on the left of each of the above groups;

R(12d) is hydrogen, methyl, or ethyl;

s is 1, 2, 3, 4, 5 or 6;

R(18) is substituted phenyl having one or two substituents selected from $NO_2$, CN, $NH_2$, N(methyl)$_2$, OH, ethyl, —COOH, —COOmethyl, —COOethyl, —$CONH_2$, and —CON(methyl)$_2$, or R(18) is a substituted N-containing heterocycle having 1, 2, 3, 4, 5, 6, 7, 8, or 9 C atoms and carrying 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(18) is —OR(19), —$SO_2$R(19), —NR(19)R(20), —CONR(19)R(20), R(19) and R(20) are the same or different and each is $C_tH_{2t}$—R(21), t is zero, 1, 2, 3, 4, 5, or 6, R(21) is hydrogen, $CF_3$, $C_2F_5$, $C_3F_7$, cycloalkyl having 3, 4, 5, 6, 7, or 8 C atoms, NR(22)R(23), —OR(24), phenyl, thienyl, or an N-containing heterocycle having 1, 2, 3, 4, 5, 6, 7, 8, or 9 C atoms, where phenyl, thienyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino;

R(22) and R(23) are the same or different and each is hydrogen, alkyl having 1, 2, or 3 C atoms, or R(22) and R(23) together form a chain of 4 or 5 methylene groups, one $CH_2$ group of which is optionally replaced by —O—, —S—, —NH—, —N($CH_3$)—, or —N(benzyl)—, R(24) is hydrogen, alkyl having 1, 2, or 3 C atoms, and the in each case the other substituents R(5), R(6), R(7) and R(8) which are not defined above are the same or different and each is hydrogen, F, Cl, Br, I, alkyl having 1, 2, 3, 4 or 5 C atoms, cycloalkyl having 3, 4, 5, 6, 7 or 8 C atoms, CN, $CF_3$, $NO_2$, OR(12e), or NR(12e)R(12f), R(12e) and R(12f) are the same or different and each is hydrogen or alkyl having 1, 2, 3, or 4 C atoms, R(9) is hydrogen, OR(12g), or OCOR(12g), R(12g) is hydrogen or alkyl having 1, 2, or 3 C atoms, B is hydrogen, or R(9) and B together form a bond; and 9) a compound of the formula IX, an isomer thereof, or a physiologically acceptable salt of any of the foregoing:

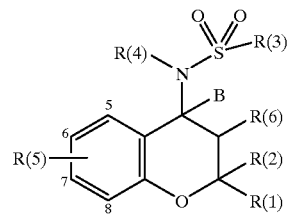

(IX)

where R(5) is attached to one of the positions labeled 5, 6, 7, and 8, and where R(1) and R(2) are the same or different and each is hydrogen, $CF_3$, $C_2F_5$, $C_3F_7$, alkyl having 1, 2, 3, 4, 5, or 6 C atoms, or phenyl, where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, or R(1) and R(2) together form an alkylene chain having 2, 3, 4, 5, 6, 7, 8, 9, or 10 C atoms, R(3) is R(10)—$C_nH_{2n}$—NR(11)— or R(10)—$C_nH_{2n}$—,
  where one $CH_2$ group in the groups $C_nH_{2n}$ is optionally replaced by —O—, —CO—, —S—, —SO—, —$SO_2$—, or —NR(12a)—,
  R(12a) is hydrogen, methyl, or ethyl,
  R(10) is hydrogen, methyl, cycloalkyl having 3, 4, 5, 6, 7, or 8 C atoms, $CF_3$, $C_2F_5$, or $C_3F_7$,
  n is zero, 1, 2, 3, 4, 5, 6, 7, 8, 9, or 10,
  R(11) is hydrogen or alkyl having 1, 2, 3, 4, 5, or 6 C atoms,
  or
  R(10) and R(11) together form a bond if n is 3 or greater,
or
R(3) together with R(4) form an alkylene chain having 3, 4, 5, 6, 7, or 8 C atoms,
  where one $CH_2$ group of the alkylene chain is optionally replaced by —O—, —CO—, —S—, —SO—, —$SO_2$—, or —NR(12a)—,
  R(12a) is hydrogen, methyl, or ethyl,
R(4) is R(13)—$C_rH_{2r}$,
  where one $CH_2$ group of the group $C_rH_{2r}$ is optionally replaced by —O—, —CH=CH—, —C≡C—, —CO—, —CO—O—, —O—CO—, —S—, —SO—, —$SO_2$—, or —NR(14)—,
  R(14) is hydrogen or alkyl having 1, 2, or 3 C atoms,
  R(13) is $CH_3$, $CF_3$, $C_2F_5$, $C_3F_7$, cycloalkyl having 3, 4, 5, 6, 7, or 8 C atoms, NR(15)R(16), phenyl, or an N-containing heterocycle having 1, 2, 3, 4, 5, 6, 7, 8 or 9 C atoms,
    where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl and methylsulfonylamino,
    R(15) and R(16) together form a chain of 4 or 5 methylene groups, one $CH_2$ group of which is optionally replaced by —O—, —S—, —NH—, —N(methyl)— or —N(benzyl)—,
  r is zero, 1, 2, 3, 4, 5, 6, 7, 8, 9, 10, 11, 12, 13, 14, 15, 16, 17, 18, 19, or 20,
R(5) is —Y—$C_sH_{2s}$—R(18) or phenyl,
  where the phenyl is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino,
  Y is —O—, —S—, or —NR(10c)—, R(10c) is hydrogen or alkyl having 1, 2, or 3 C atoms,
  s is 1, 2, 3, 4, 5, 6, 7, or 8,
  R(18) is hydrogen, $CF_3$, $C_2F_5$, $C_3F_7$, cycloalkyl having 3, 4, 5, 6, 7 or 8 C atoms, —COOR(21), NR(15a)R(16a), an unsubstituted N-containing heterocycle having 1, 2, 3, 4, 5, 6, 7, 8, or 9 C atoms, phenyl, or thienyl,
    where phenyl and thienyl are unsubstituted or substituted by 1 or 2 substituents selected from F, Cl, Br, I, $CF_3$, methyl, methoxy, sulfamoyl, methylsulfonyl and methylsulfonylamino,
    R(15a) and R(16a) together form a chain of 4 or 5 methylene groups, one $CH_2$ group of which is optionally replaced by —O—, —S—, —NH—, —N(methyl)—, or —N(benzyl)—,
    R(21) is hydrogen or alkyl having 1, 2, or 3 C atoms, R(6) is OR(10d) or OCOR(10d),
  where R(10d) is hydrogen or alkyl having 1, 2, or 3 C atoms,
B is hydrogen,
or
R(6) and B together form a bond; and
10) a compound of the formula X, an isomer thereof, or a physiologically acceptable salt of any of the foregoing:

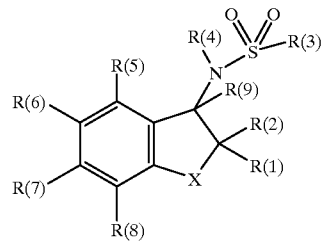

(X)

where
R(1) and R(2) are the same or different and each is hydrogen, $CF_3$, alkyl having 1, 2, 3, 4, 5, or 6 C atoms,
or
R(2) and R(9) together form a bond,
or R(2) is —OR(10a),
  where R(10a) is hydrogen, acetyl or alkyl having 1, 2, or 3 C atoms,
R(3) is R(10b)—$C_nH_{2n}$—NR(11)—, or R(10b)—$C_nH_{2n}$—,
  where one $CH_2$ group in the groups $C_nH_{2n}$ is optionally replaced by —O—, —CO—, —S—, —SO—, —$SO_2$—, or —NR(12a)—,
  where R(12a) is hydrogen, methyl, or ethyl,
  R(10b) is methyl, cycloalkyl having 3, 4, 5, 6, 7, or 8 C atoms, $CF_3$, $C_2F_5$, or $C_3F_7$,
  n is zero, 1, 2, 3, 4, 5, 6, 7, 8, 9, or 10,
  R(11) is hydrogen or alkyl having 1, 2, 3, 4, 5, or 6 C atoms,
  or
  R(10b) and R(11) together form a bond if n is 2 or greater,
or
R(3) together with R(4) is an alkylene chain having 3, 4, 5, 6, 7, or 8 C atoms,
  where one $CH_2$ group of the alkylene chain is optionally replaced by —O—, —CO—, —S—, —SO—, —$SO_2$—, or —NR(12a)—,
  R(12a) is hydrogen, methyl or ethyl,
R(4) is R(13)—$C_rH_{2r}$,
  where one $CH_2$ group of the group $C_rH_{2r}$ is optionally replaced by —O—, —CH=CH—, —C≡C—, —CO—, —CO—O—, —O—CO—, —S—, —SO—, —$SO_2$—, —NR(14)— or —CONR(14)—,
  R(14) is hydrogen, alkyl having 1, 2, or 3 C atoms, —$C_yH_{2y}$—OR(12b), —$C_yH_{2y}$—NR(12b)$_2$,
  R(12b) is hydrogen, methyl, or ethyl,
  y is 2 or 3,
  R(13) is $CH_3$, $CF_3$, $C_2F_5$, $C_3F_7$, cycloalkyl having 3, 4, 5, 6, 7, or 8 C atoms, —NR(15)R(16), —CONR(15)R(16), —OR(17), —COOR(17), phenyl, or an N-containing heterocycle having 1, 2, 3, 4, 5, 6, 7, 8, or 9 C atoms, where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(15) and R(16) are the same or different and each is hydrogen or alkyl having 1, 2, 3, or 4 C atoms, or R(15) and R(16) together form a chain of 4 or 5 methylene groups, one $CH_2$ group of which is optionally replaced by —O—, —S—, —NH—, —N($CH_3$)— or —N(benzyl)—, R(17) is hydrogen, alkyl having 1, 2, or 3 C atoms, —$C_zH_{2z}$OR(12c), R(12c) is hydrogen, methyl, or ethyl, z is 2 or 3, r is zero, 1, 2, 3, 4, 5, 6, 7, 8, 9, 10, 11, 12, 13, 14, 15, 16, 17, 18, 19, or 20, R(5), R(6), R(7) and R(8) are the same or different and each is hydrogen, F, Cl, Br, I, alkyl having 1, 2, 3, 4, or 5 C atoms, cycloalkyl having 3, 4, 5, 6, 7 or 8 C atoms, —CN, —$CF_3$, —$C_2F_5$, —$C_3F_7$, —$N_3$, —$NO_2$, —Y—$C_sH_{2s}$—R(18), phenyl, thienyl, furyl, or an N-containing heterocycle having 1, 2, 3, 4, 5, 6, 7, 8, or 9 C atoms, where phenyl, thienyl, furyl, and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, Y is —O—, —CO—, —CO—O—, —O—CO—, —S—, —SO—, —$SO_2$—, —O—$SO_2$—, —$SO_2$NR(10c), or —CONR(10c)—, where the attachment to the benzene ring is, in each case, effected through the atom depicted on the left of each of the above groups, where R(10c) is hydrogen or alkyl having 1, 2, or 3 C atoms, s is zero, 1, 2, 3, 4, 5, or 6, R(18) is hydrogen, methyl, $CF_3$, $C_2F_5$, $C_3F_7$, cycloalkyl having 3, 4, 5, 6, 7, or 8 C atoms, —OR(21), —COOR(21), —NR(15a)R(16a), —CONR(15a)R(16a), phenyl, or an N-containing heterocycle having 1, 2, 3, 4, 5, 6, 7, 8, or 9 C atoms, where phenyl and the N-containing heterocycle are unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl, and methylsulfonylamino, R(15a) and R(16a) are the same or different and each is hydrogen or alkyl having 1, 2, 3, or 4 C atoms, or R(15a) and R(16a) together form a chain of 4 or 5 methylene groups, one $CH_2$ group of which is optionally replaced by —O—, —S—, —NH—, —N($CH_3$)—, or —N(benzyl)—, R(21) is hydrogen or alkyl having 1, 2, or 3 C atoms, R(9) is hydrogen or, together with R(2), forms a bond, X is —CR(22)R(23)—, —O—, —NR(24)—, —S—, —SO—, —$SO_2$—, R(22) and R(23) are the same or different and each is hydrogen, $CF_3$, alkyl having 1, 2, 3, 4, 5, or 6 C atoms, R(24) is hydrogen, alkyl having 1, 2, 3, 4, 5, or 6 C atoms, or phenyl, where any of the foregoing is unsubstituted or substituted by 1 or 2 substituents selected from F, Cl, Br, I, $CF_3$, $NO_2$, CN, $NH_2$, OH, methyl, ethyl, methoxy, dimethylamino, sulfamoyl, methylsulfonyl and methylsulfonylamino.

6. A method according to claim 1, wherein the KQT1 channel blocker comprises at least one compound selected from:

a) 6-cyano-4-trans-(N-ethylsulfonyl-N-methylamino)-3-hydroxy-2,2-dimethylchromane b) N-ethylsulfonyl-N-methylamino-8-fluorobenzocycloheptane c) 4-N-ethylsulfonyl-N-methylamino-6,7-dimethoxy-2,2-dimethylchromane d) 7-chloro-4-N-ethylsulfamoyl-N-methylamino-6-fluoro-2,2-dimethylchromane, e) 6,7-dichloro-4-[N-ethylsulfonyl-N-(4,4,4-trifluorobutyl)amino]-2,2-dimethylchromane, f) 2-[ethanesulfonyl-(6-fluoro-2,2-dimethyl-chroman-4-yl)-amino]-N-pyridin-4-yl-acetamide, g) N-(2-dimethylaminoethyl)-2-[ethanesulfonyl-(6-fluoro-2,2-dimethyl-chroman-4-yl)amino]-acetamide, h) N-[2-benzyl-methyl-amino)-ethyl]-2-[ethanesulfonyl-(6-fluoro-2,2-dimethyl-chroman-4-yl)-amino]-acetamide, i) (3R,4S)-(+)-N-[3-hydroxy-2,2-dimethyl-6-(4,4,4-trifluorobutoxy)-chroman-4-yl]-N-methyl-methanesulfonamide, j) (3S,4R)-(−)-N-[3-hydroxy-2,2-dimethyl-6-(4,4,4-trifluorobutoxy)-chroman-4-yl]-N-methyl-methanesulfonamide, k) N-[2,2-dimethyl-6-(4,4,4-trifluorobutoxy)-2H-chromen-4-yl]-N-methylmethanesulfonamide.

* * * * *

UNITED STATES PATENT AND TRADEMARK OFFICE
CERTIFICATE OF CORRECTION

PATENT NO.    : 6,335,363 B1  
DATED         : January 1, 2002  
INVENTOR(S)   : Uwe Gerlach et al.

Page 1 of 1

It is certified that error appears in the above-identified patent and that said Letters Patent is hereby corrected as shown below:

<u>Column 59,</u>  
Line 62, "iszero" should read -- is zero --.

<u>Column 92,</u>  
Line 28, "or." should read -- or --.

Signed and Sealed this

Twenty-eighth Day of May, 2002

Attest:

Attesting Officer

JAMES E. ROGAN  
*Director of the United States Patent and Trademark Office*